United States Patent
Konakanchi et al.

(10) Patent No.: US 8,349,847 B2
(45) Date of Patent: Jan. 8, 2013

(54) PYRAZOLO [3,4-D] PYRIMIDINE DERIVATIVES AS ANTI-CANCER AGENTS

(76) Inventors: Durga Prasad Konakanchi, Hyderabad (IN); Subba Rao Pula, Hyderabad (IN); Lakshmi Ananthaneni, Hyderabad (IN); Ramakrishna Pilli, Hyderabad (IN); Muddasani Pulla Reddy, Hyderabad (IN); Bhujanga rao Adibhatla Satya, Hyderabad (IN); Nannapaneni Venkaiah Chowdary, Hyderabad (IN)

( * ) Notice: Subject to any disclaimer, the term of this patent is extended or adjusted under 35 U.S.C. 154(b) by 107 days.

(21) Appl. No.: 12/812,405

(22) PCT Filed: Jan. 12, 2009

(86) PCT No.: PCT/IN2009/000037
§ 371 (c)(1),
(2), (4) Date: Jul. 9, 2010

(87) PCT Pub. No.: WO2009/098715
PCT Pub. Date: Aug. 13, 2009

(65) Prior Publication Data
US 2010/0298351 A1    Nov. 25, 2010

(30) Foreign Application Priority Data
Jan. 11, 2008 (IN) .............................. 109/CHE/2008

(51) Int. Cl.
*A01N 43/90* (2006.01)
*A61K 31/519* (2006.01)
*C07D 487/00* (2006.01)

(52) U.S. Cl. ..................................... 514/262.1; 544/262
(58) Field of Classification Search ........................ None
See application file for complete search history.

(56) References Cited

U.S. PATENT DOCUMENTS
5,593,997 A    1/1997    Dow et al.

FOREIGN PATENT DOCUMENTS
WO    WO 02/45716    6/2002

OTHER PUBLICATIONS

Schmidt, et. al. Helvetica Chimica Acta (1956), 39(3), 986-91.*
Peat et al. "Novel pyrazolopyrimidine derivaties as GSK-3 inhibitors." *Bioorganic & Medicinal Chem. Letters.* vol. 14. 2004. pp. 2121-2125.
Cavasotto et al. "In silico identificationi of novel EGFR inhibitors with antiproliferative activity against cancer cells." *Bioorganic & Medicinal Chem. Letters.* vol. 16. 2006. pp. 1969-1974.
Daniels et al. "Microwave-assisted protocols for the expedited synthesis of pyrazolo[1-5-a] and [3,4-d]pyrimidines." *Tetrahedron Letters.* vol. 49. 2008. pp. 305-310.
Maduskuie, Jr. et al. "Design, Synthesis, and Structure—Activity Relationship studies for a new imidazole series of J774 Macrophage Specific Acyl-CoA:Cholesterol Acyltransferase (ACAT) Inhibitors." *J. Med. Chem.* vol. 38. 1995. pp. 1067-1083.

* cited by examiner

*Primary Examiner* — Jeffrey Murray
(74) *Attorney, Agent, or Firm* — Merchant & Gould P.C.

(57) ABSTRACT

The invention relates to substituted pyrazolo[3,4-d]pyrimidine derivatives of the Formula-(I), or pharmaceutically-acceptable salts thereof, which possess anti-proliferative activity such as anti-cancer activity and are accordingly useful in methods of treatment of the human or animal body. The invention also relates to processes for the manufacture of substituted pyrazolo[3,4-d]pyrimidine derivatives, to pharmaceutical compositions containing the compound and to its use in the manufacture of medicaments for the production of an anti-proliferative effect in a warm-blooded animal such as man.

33 Claims, No Drawings

PYRAZOLO [3,4-D] PYRIMIDINE DERIVATIVES AS ANTI-CANCER AGENTS

This application is a National Stage Application of PCT/IN2009/000037, filed 12 Jan. 2009, which claims benefit of Serial No. 109/CHE/2008, filed 11 Jan. 2008 in India and which applications are incorporated herein by reference. To the extent appropriate, a claim of priority is made to each of the above disclosed applications.

FIELD OF INVENTION

The invention relates to substituted pyrazolo[3,4-d]pyrimidine derivatives of the formula-I,

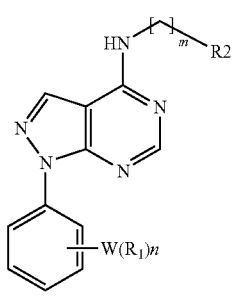

Formula-I or pharmaceutically-acceptable salts thereof, which possess anti-proliferative activity such as anti-cancer activity and are accordingly useful in methods of treatment of the human or animal body. The invention also relates to processes for the manufacture of substituted pyrazolo[3,4-d]pyrimidine derivatives, to pharmaceutical compositions containing the compound and to its use in the manufacture of medicaments for the production of an anti-proliferative effect in a warm-blooded animal such as man.

Aberrant signal transduction is a hallmark of carcinogenesis. Cell surface receptors, their ligands and protein tyrosine kinases are key components of growth signaling pathways and are mutated or upregulated in a wide variety of human tumors. In particular, the epidermal growth factor receptor (EGFR) pathway has been implicated in tumor-promoting events such as cell division, cell adhesion and migration, angiogenesis, and anti-apoptosis. EGFR overexpression, found in one-third of epithelial cancers overall, can vary from 20 to 80% depending on histologic type and is associated with resistance to hormonal therapy, cytotoxic agents and radiation.

EGFR belongs to the erbB family of structurally related receptors, comprising EGFR (HER-1, erbB1), HER-2/neu (erbB2), HER-3 (erbB3), and HER-4 (erbB4). These transmembrane glycoproteins possess an external ligand-binding domain, a cytoplasmic tyrosine kinase (TK) domain, and a Src homology 2 (SH2) domain for substrate binding. EGF, transforming growth factor-a and amphiregulin bind exclusively to EGFR, while heparin-binding EGF, beta-cellulin and epiregulin bind EGFR and HER-4, and heregulins and neuregulins bind HER-3 and HER-4.

The central role of EGFR in cancer has engendered strenuous efforts to develop EGFR antagonists. The two strategies that are furthest along in clinical trials are receptor monoclonal antibodies, which block ligand binding and receptor activation, and small-molecule inhibitors of EGFR TK. The first-generation small-molecule inhibitors act as ATP analogs competing reversibly for the TK catalytic site. Newer inhibitors that are under development produce irreversible antagonism and/or target multiple erbB receptors Receptor tyrosine kinases are important in the transmission of biochemical signals, which initiate cell replication. They are large enzymes which span the cell membrane and possess an extracellular binding domain for growth factors such as epidermal growth factor (EGF) and an intracellular portion which functions as a Kinase to phosphorylate tyrosine amino acids in proteins and hence to influence cell proliferation. Various classes of receptor tyrosine kinases are known (Wilks, Advances in Cancer Research, 1993, 60, 43-73) based on families of growth factors, which bind to different receptor tyrosine kinases. The classification includes Class I receptor tyrosine kinases comprising the EGF family of receptor tyrosine kinases such as the EGF, TGFα, NEU, erbB, Xmrk, HER and let23 receptors, Class II receptor tyrosine kinases comprising the insulin family of receptor tyrosine kinases such as the insulin, IGFI and insulin-related receptor (IRR) receptors and Class III receptor tyrosine kinases comprising the platelet-derived growth factor (PDGF) family of receptor tyrosine kinases such as the PDGFα, PDGFβ. and colony stimulating factor 1 (CDF1) receptors.

It is known that Class I kinases such as the EGF family of receptor tyrosine kinases are frequently present in common human cancers such as breast cancer (Sainsbury et. al., Brit J. Cancer, 1988, 58, 458; Guerin et al, Oncogene Res., 1988, 3, 21 and Klijn et al., Breast Cancer Res. Treat., 1994, 29, 73), non-small cell lung cancers (NSCLCs) including adenocarcinomas (Cerny et., Brit. J. Cancer, 1986, 54, 265; Reubi et al., Int. J. Cancer, 1990, 45, 269; and Rusch et al., Cancer Research, 1993, 53, 2379) and squamous cell cancer of the lung (Hendler et al., Cancer Cells, 1989, 7, 347), bladder cancer (Neal et al., Lancet, 1985, 366), oesophageal cancer (Mukaida et al., Cancer, 1991, 68, 142), gastrointestinal cancer such as colon, rectal or stomach cancer (Bolen et al., Oncogene Res., 1987, 1, 149), cancer of the prostate (Visakorpi et al., Histochem. J., 1992, 24, 481), leukemia (Konaka et al., Cell, 1984, 31, 1035) and ovarian, bronchial or pancreatic cancer (European Patent Specification No. 0400586). As further human tumour tissues are tested for the EGF family of receptor tyrosine kinases it is expected that their widespread prevalence will be established in further cancers such as thyroid and uterine cancer. It is also known that EGF type tyrosine Kinase activity is rarely detected in normal cells whereas it is more frequently detectable in malignant cells (Hunter, Cell., 1987, 50, 823). It has been shown more recently (W J Gullick, Brit. Med. Bull., 1991, 47, 87) that EGF receptors which possess tyrosine kinase activity are over expressed in many human cancers such as brain, lung squamous cell, bladder, gastric, breast, head and neck, esophageal, gynecological and thyroid tumors.

Accordingly it has been recognized that an inhibitor of receptor tyrosine kinases should be of value as a selective inhibitor of the growth of mammalian cancer cells (Yaish et al. Science, 1988, 242, 933). Support for this view is provided by the demonstration that erbstatin, an EGF receptor tyrosine kinase inhibitor, specifically attenuates the growth in athymic nude mice of a transplanted human mammary carcinoma which expresses EGF receptor tyrosine kinase but is without effect on the growth of another carcinoma which does not express EGF receptor tyrosine kinase (Toi et al., Eur. J. Cancer Clin. Oncol., 1990, 26, 722.) Various derivatives of styrene are also stated to possess tyrosine kinase inhibitory properties (European Patent Application Nos. 0211363, 0304493 and 0322738) and to be of use as anti-tumour agents. The in vivo inhibitory effect of two such styrene derivatives which are EGF receptor tyrosine kinase inhibitors has been demonstrated against the growth of human squamous cell carcinoma inoculated into nude mice (Yoneda et al., Cancer Research, 1991, 51, 4430). Various known tyrosine kinase inhibitors are disclosed in a more recent review by T R Burke Jr. (Drugs of the Future, 1992, 17, 119). Examples of signal transduction inhibitors include agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA). EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.). VEGF inhibitors, for example SU-5416 and SU-6668 (Sugen Inc. of South San Francisco, Calif., USA), can also be combined or co-administered with the composition. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); anti-VEGF monoclonal antibody bevacizumab (Genentech, Inc. of South San Francisco, Calif.); and angiozyme, a synthetic ribozyme from Ribozyme (Boulder, Colo.) and Chiron (Emeryville, Calif.). ErbB2 receptor inhibitors, such as GW-282974 (Glaxo Wellcome pic), and the monoclonal antibodies AR-209 (Aronex Pharmaceuticals Inc. of The Woodlands, Tex., USA) and 2B-1 (Chiron), may be administered in combination with the composition. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety. Other antiproliferative agents that may be used include inhibitors of the enzyme famesyl protein transferase and inhibitors of the receptor tyrosine kinase PDGFr, including the compounds disclosed and claimed in the following U.S. patent application Ser. Nos. 09/221,946 (filed Dec. 28, 1998); 09/454,058 (filed Dec. 2, 1999); 09/501,163 (filed Feb. 9, 2000); 09/539, 930 (filed Mar. 31, 2000); 09/202,796 (filed May 22, 1997); 09/384,339 (filed Aug. 26, 1999); and 09/383,755 (filed Aug. 26, 1999); and the compounds disclosed and claimed in the following U.S. provisional patent applications: 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety. Compositions of the invention can also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors. Specific CTLA4 antibodies that can be used in the present invention include those described in U.S. Provisional Application 60/113,647 (filed Dec. 23, 1998) which is herein incorporated by reference in its entirety.

The receptor tyrosine kinases are of particular importance in the transmission of mitogenic signals that initiate cellular replication. These large glycoproteins, which span the plasma membrane of the cell, possess an extracellular binding domain for their specific ligands (such as Epidermal Growth Factor (EGF) for the EGF Receptor). Binding of ligand results in the activation of the receptor's kinase enzymatic activity that resides in the intracellular portion of the receptor. This activity phosphorylates key tyrosine amino acids in target proteins, resulting in the transduction of proliferative signals across the plasma membrane of the cell.

It is known that the erbB family of receptor tyrosine kinases, which include EGFR, erbB2, erbB3 and erbB4, are frequently involved in driving the proliferation and survival of tumour cells (reviewed in Olayioye et al., EMBO J., 2000, 19, 3159). One mechanism in which this can be accomplished is by overexpression of the receptor at the protein level, generally as a result of gene amplification. This has been observed in many common human cancers (reviewed in Klapper et al., Adv. Cancer Res., 2000, 77, 25) such as breast cancer (Sainsbury et al., Brit. J. Cancer. 1988, 58, 458; Guerin et al., Oncogene Res. 1988, 3, 21; Slamon et al. Science. 1989, 244, 707; Kliin et al., Breast Cancer Res. Treat. 1994, 29, 73 and reviewed in Salomon et al., Crit. Rev. Oncol. Hematol. 1995, 19, 183), non-small cell lung cancers (NSCLCs) including adenocarcinomas (Cerny et al., Brit. J. Cancer. 1986, 54, 265; Reubi et al., Int. J. Cancer. 1990, 45, 269; Rusch et al., Cancer Research. 1993, 53, 2379; Brabender et al, Clin. Cancer Res. 2001, 7, 1850) as well as other cancers of the lung (Hendler et al., Cancer Cells. 1989, 7, 347; Ohsaki et al, Oncol. Rep. 2000, 7, 603), bladder cancer (Neal et al., Lancet. 1985, 366; Chow et al., Clin. Cancer Res. 2001, 7, 1957, Zhau et al., Mol Carcinog., 3, 254), oesophageal cancer (Mukaida et al., Cancer. 1991, 68, 142), gastrointestinal cancer such as colon, rectal or stomach cancer (Bolen et al., Oncogene Res. 5 1987, 1, 149; Kapitanovic et al., Gastroenterology. 2000, 112, 1103; Ross et al., Cancer Invest. 2001, 19, 554), cancer of the prostate (Visakorpi et al., Histochem. J. 1992, 24, 481; Kumar et al. 2000, 32, 73; Scher et al. J. Natl. Cancer Inst. 2000, 92, 1866), leukaemia (Konaka et al., CeU, 1984, 37, 1035, Martin-Subero et al. Cancer Genet Cytogenet. 2001, 127-174), ovarian (Hellstrom eLal., Cancer Res. 2001, 6_1, 2420), head and neck (Shiga et al., 0 Head Neck. 2000, 22, 599) or pancreatic cancer (Ovotny et al., Neoplasma. 2001, 48, 188). As more human tumour tissues are tested for expression of the erbB family of receptor tyrosine kinases it is expected that their widespread prevalence and importance will be further enhanced in the future.

It is also expected that inhibitors of EGF type receptor tyrosine kinases will be useful in the treatment of other diseases of excessive cellular proliferation such as psoriasis. AstraZeneca has developed and launched Gefitinib (U.S. Pat. No. 5,770,599), of the formula II,

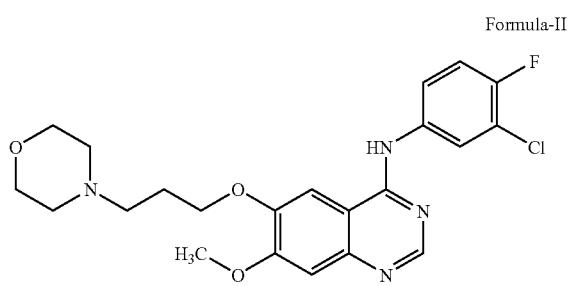 [SMILES: COc1cc2ncnc(Nc3ccc(F)c(Cl)c3)c2cc1OCCCN1CCOCC1]

Formula-II an orally active, selective epidermal growth factor receptor-tyrosine kinase inhibitor (EGFR-TK1). It is indicated as monotherapy for the continued treatment of patients with locally advanced or metastatic non-small cell lung cancer after failure of both platinum-based and docetaxel chemotherapies that are benefiting or have benefited from gefitinib. The brand name is Iressa.

OSI Pharmaceuticals has developed and launched Erlotinib (U.S. Pat. No. 5,747,498) of formula-III,

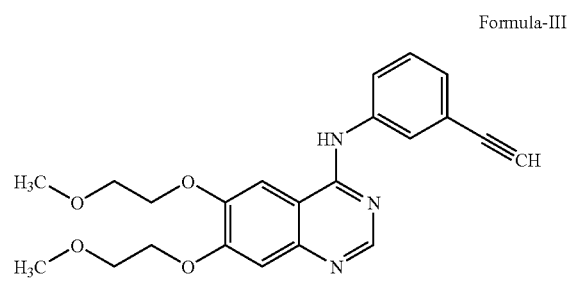 [SMILES: C#Cc1cccc(Nc2ncnc3cc(OCCOC)c(OCCOC)cc23)c1]

Formula-III an orally active, ATP-competitive small-molecule inhibitor of EGFR TK. It is presently being used as a standard treatment for non-small cell lung cancer (NSCLC) and pancreatic cancer diseases. Its activity is expected to be enhanced when combined with standard cytotoxic antibiotic anti-cancer drugs. The brand name is Tarceva.

Furthermore, inhibitory antibodies against EGFR and erbB2 (Erbitux® (c-225/cetuximab) and Herceptin® (trastuzumab) respectively) have proven to be beneficial in the clinic for the treatment of selected solid tumours (reviewed in Mendelsohn et al, 2000, 5 Oncogene, 19, 6550-6565).

There are number of patents published with compounds containing pyrazolo[3,4-d]pyrimidine neuclus as anti cancer drug.

WO-96/31510 and WO-98/14449 each discloses 4-amino-1H-pyrazolo[3,4-d]ipyrimidine derivatives and their use as anti-tumour agents.

WO-98/14451 discloses 3-(3-aminobenzylamino)-4-(3-chlorophenylamino)-1H-pyrazolo[3,4-d]pyrimidine, its use as an anti-tumour agent and its use in cases of epidermal hyperproliferation.

WO-98/14450 discloses 4-amino-1H-pyrazolo[3,4-d]ipyrimidine derivatives that carry a nitrogen-linked substituent at the 3-position on the pyrazolo[3,4-d]pyrimidine ring, and their use as anti-tumour agents.

WO-95/19774 discloses bicyclic pyrimidine derivatives and their use as inhibitors of the EGF, erbB2 and erbB4 receptor tyrosine kinases. A pyrazolo[3,4-d]pyrimidine derivative is disclosed that includes an amino-aryl group at the 4-position on the pyrazolo[3,4-d]ipyrimidine ring but no substituent at the 3-position.

Makarov et al. (Chemistry of Heterocyclic Compounds, 2003, 39(2), 238-243) discloses the reaction of 3,5-di-(N,N-dimethylaminomethylene)amino-4-methoxycarbonylpyrazole and 3,5-di-(N,N-dimethylaminomethylene)amino-4-cyanopyrazole compounds with certain amines to form pyrazolo[3,4-d]pyrimidine compounds.

International Patent Publication No. WO 03/000187 describes novel pyrazolo- and pyrrolo-pyrimidines. International Patent Publication No. WO 02/057267, U.S. Pat. Nos. 6,686,366, 6,680,324, and 6,673,802 describe compounds specific to adenosine A1, A2A, and A3 receptors. International Patent Publication No. WO 01/47507 describes combinations of a receptor tyrosine kinase inhibitor with an organic compound capable of binding to α1-acidic glycoprotein. International Patent Publication No. WO 04/013141 describes condensed pyridines and pyrimidines with TIE2 (TEK) activity. International Patent Publication No. WO 04/014850 describes substituted aminopyrimidines as neurokinin antagonists.

International Patent Publication No. WO 03/000695 describes pyrrolopyrimidines as protein kinase inhibitors. U.S. Pat. No. 6,187,778 describes 4-aminopyrrol[3,4-d]pyrimidines as neuropeptide Y receptor antagonists. U.S. Pat. Nos. 6,140,317, 6,140,332, and 6,180,636 describe pyrrolopyrimidines. U.S. Pat. Nos. 6,696,455, 6,537,999 and 5,877,178 describe pyrrolo?? pyrimidine derivatives. U.S. Pat. No. 5,958,930 describes pyrrolopyrimidine and furopyrimidine derivatives. [29] International Patent Publication No. 03/000688 describes the preparation of azaindoles as protein kinase inhibitors. International Patent Publication Nos. WO 03/018021 and WO 03/018022 describe pyrimidines for treating IGF-IR related disorders, International Patent Publication No. WO 02/092599 describes pyrrolopyrimidines for the treatment of a disease that responds to an inhibition of the IGF-IR tyrosine kinase, International Patent Publication No. WO 01/72751 describes pyrrolopyrimidines as tyrosine kinase inhibitors. International Patent Publication No. WO 00/71129 describes pyrrolotriazine inhibitors of kinases. International Patent Publication No. WO 97/28161 describes pyrrolo[2,3-d]pyrimidines and their use as tyrosine kinase inhibitors.

Further literature references of pyrazolo[3,4-d]pyrimidine derivatives as anti-cancer agents J. Heterocycl. Chem., 27, 647-660, J. Med. Chem., 1976, 19, 555-558, J. Heterocycl. Chem., 1990, 27, 1245-1248, Journal of the Chinese Chemical Society, 2000, 47, 347-350, U.S. Pat. No. 5,917,039, U.S. Pat. No. 6,423,871, J. Org. Chem. 1956 21(11) 1240-1256, J. Med. Chem. 1991, 34, 2892-2898, Helvetica Chimica Acta (1956)-No. 119, 987-991, J. Med. Chem. 1997, 40, 3601-3616, U.S. Pat. No. 3,600,389, U.S. Pat. No. 4,182,878

Although the anticancer compounds described above have made a significant contribution to the art, there is a continuing need to improve anticancer pharmaceuticals with better selectivity or potency, reduced toxicity, or fewer side effects.

PRESENT INVENTION

Surprisingly, we have now found that a select group of substituted pyrazolo[3,4-d]pyrimidine derivatives of the present invention, or a pharmaceutically acceptable salt thereof, possess potent anti-tumour activity. None of the prior art discloses pyrazolo[3,4-d]pyrimidine compounds that are substituted at the 1-position with a substituent containing an ethynyl group or 3,5-disubstituted groups and at 4 position substituted benzyl amines. Without wishing to imply that the compounds disclosed in the present invention possess pharmacological activity only by virtue of an effect on a single biological process, it is believed that the compounds provide an anti-tumour effect by way of inhibition of one or more of the erbB family of receptor tyrosine kinases that are involved in the signal transduction steps which lead to the proliferation of tumour cells. In particular, it is believed that the compounds of the present invention provide an anti-tumour effect by way of inhibition of EGF and/or erbB2 receptor tyrosine kinases.

Such processes, when used to prepare the substituted pyrazolo[3,4-d]pyrimidine derivative of the invention, or a pharmaceutically-acceptable salt thereof, are provided as a further feature of the invention and are illustrated by the following representative Examples. Necessary starting materials may be obtained by standard procedures of organic chemistry. The preparation of such starting materials is described within the accompanying non-limiting Examples. Alternatively necessary starting materials are obtainable by analogous procedures to those illustrated, which are within the ordinary skill of an organic chemist.

The invention relates to Substituted pyrazolo[3,4-d]pyrimidine derivatives of formula-I,

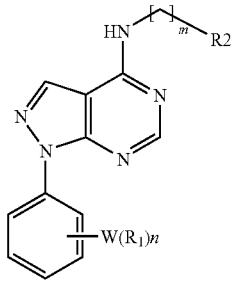

Formula-I and pharmaceutically acceptable salts thereof,
wherein n and m are 1, 2, or 3;

W is single bond, $C_1$-$C_6$ alkyl, alkenyl, alkynyl, NH, S, SO, SO2, O, C=O or an amide group, each $R_1$ is independently selected from hydrogen, halo, hydroxy, amino, hydroxyamino, carboxy, nitro, guanidino, ureido, carbamoyl, cyano, trifluoromethyl, or each $R_1$ is independently selected from the group consisting of $C_1$-$C_6$ alkyl, $C_3$-$C_6$ cycloalkyl, $C_1$-$C_6$ alkoxy, $C_3$-$C_6$ cycloalkoxy, ($C_1$-$C_6$)alkoxycarbonyl, aryloxy, heteroaryloxy, $C_1$-$C_6$ thioalkoxy, $C_3$-$C_6$ thiocycloalkoxy, thioaryloxy, thioheteroaryloxy, nitro, amino, N-mono($C_1$-$C_6$)alkylamino, N,N-di($C_1$-$C_6$)alkylamino, formamido, amido, acetamido, hydroxylamino, $C_1$-$C_6$ alkoxyamino, hydrazino, trifluoromethyl, trifluoromethoxy, $C_2$-$C_6$ alkenyl, $C_2$-$C_6$ alkynyl, aryl, heterocyclyl, fused aryl, fused heteroaryl and fused heterocyclyl;

each $R_1$ is independently selected from $R_3$-sulfonylamino, phthalimido-($C_1$-$C_4$)-alkylsulfonylamino, benzamido, benzenesulfonylamino, 3-phenylureido, 2-oxopyrrolidin-1-yl, 2,5-dioxopyrrolidin-1-yl, and $C_2$-$C_4$ alkanoylamino and wherein said benzenesulfonylamino or phenyl or phenoxy or anilino or phenylsulfanyl substituent in $R^1$ may optionally bear one or two halogens, ($C_1$-$C_4$)alkyl, cyano, methansulfonyl or ($C_1$-$C_4$)alkoxy substituents; or any two $R_1$ taken together with the carbons to which they are attached comprise a 5-8 membered ring comprising at least one or two heteroatoms selected from oxygen, sulfur or nitrogen; and wherein the alkyl groups and alkyl portions of the alkoxy or alkylamino groups may be straight chained or if comprised of at least three carbons may be branched or cyclic;

where $R_3$ is selected from $C_1$-$C_6$-alkyl, $C_3$-$C_6$ cycloalkyl $R_2$ is selected from the group consisting of hydrogen, $C_1$-$C_6$ alkyl, $C_3$-$C_6$ cycloalkyl, $C_1$-$C_6$ alkoxycarbonyl, aryl, heteroaryl, $C_1$-$C_6$ thioalkyl, trifluoromethyl, trifluoromethoxy, heterocyclyl, fused aryl, fused heteroaryl and fused heterocyclyl, such as 1,3-benzodioxol, 1,4-benzodioxin, And $R_2$ is selected from the group consisting of phenyl or benzyl and substituted with 1, 2, 3 or 4 groups and the substitutents are independently selected from R4, where R4 is selected from hydrogen, halo, hydroxy, amino, hydroxyamino, carboxy, nitro, guanidino, ureido, carbamoyl, cyano, trifluoromethyl, $C^1$-$C^6$-alkyl, $C_3$-$C_6$ cycloalkyl, hydroxy, $C_1$-$C_6$ alkoxy, $C_3$-$C_6$ cycloalkoxy, $C_1$-$C_6$ alkoxycarbonyl, aryloxy, heteroaryloxy, $C_1$-$C_6$ thioalkoxy, $C_3$-$C_6$ thiocycloalkoxy, thioaryloxy, thioheteroaryloxy, nitro, amino, N-mono($C_1$-$C_6$)alkylamino, N,N-di($C_1$-$C_6$)alkylamino, formamido, amido, acetamido, hydroxylamino, $C_1$-$C_6$ alkoxyamino, hydrazino, trifluoromethyl, trifluoromethoxy, alkenyl, alkynyl, aryl, heterocyclyl, fused aryl, fused heteroaryl and fused heterocyclyl;

DETAILED DESCRIPTION OF THE INVENTION

Formula-I compounds and pharmaceutically acceptable salts thereof may be prepared by any process known to be applicable to the chemically related compounds. The active compounds of present invention can be prepared by the following synthetic Scheme-I.

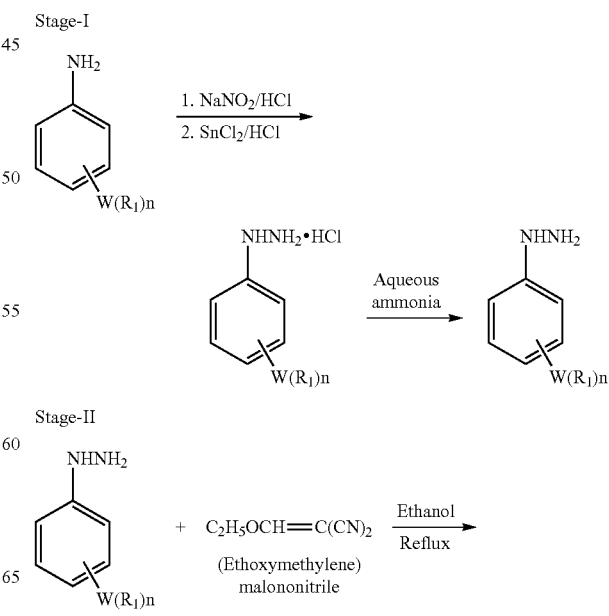

Stage-III

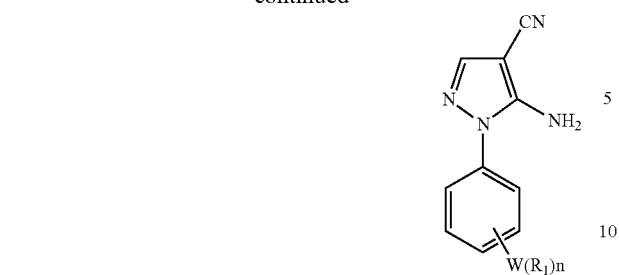

Stage-IV

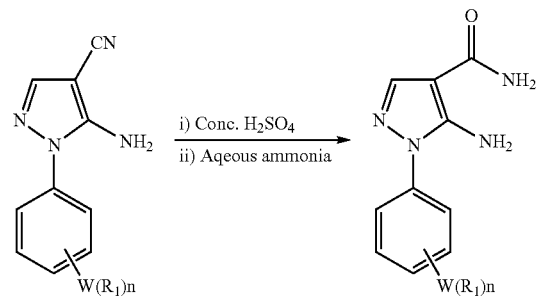

Stage-V

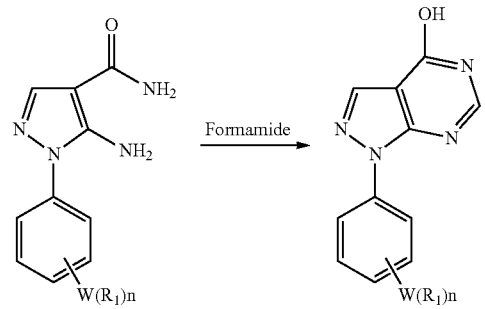

Stage-VI

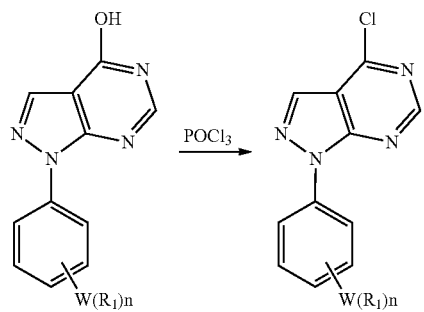

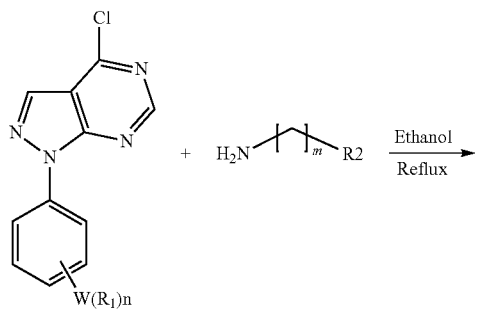

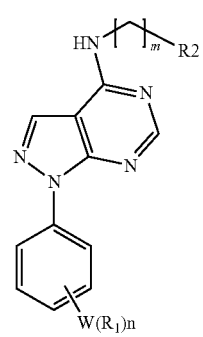

$R_1$, R2, and W are defined as above.

SCHEME-I

Various compounds of formula-I are can also be prepared by following routes:

(a)

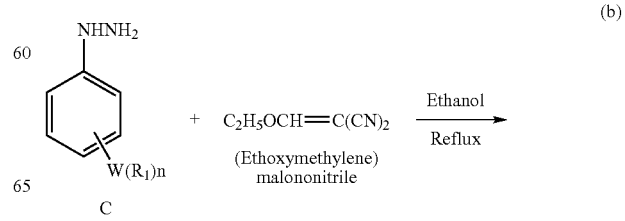

By known methods given in the literature, diazotising a compound of formula A with mineral acid such as hydrochloric acid and with sodium nitrite solution at temperatures −10° C. to 5° C. to obtain substituted phenyl hydrazine hydrochloride of formula-B. The other mineral acids can be used are sulphuric acid, etc. The formula-B compound is neutralised with a suitable base such as ammonia, mono-, di- or trialkyl amines, sodium hydroxide, potassium hydroxide, sodium carbonate, potassium carbonate, ammonium carbonate and bicarbonates of alkali metals to get the novel substituted phenyl hydrazines of formula-C.

(b)

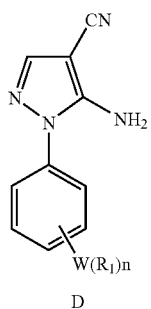

D

The compound of formula C is reacted with ethoxy methelenemalononitrile in protic solvents such as methanol, ethanol, isopropanol n-butanol, dimethyl formamide or mixtures of these solvents at temperatures 60° C. to obtain novel N-substituted phenyl-5-amino-1H-pyrazole-4-carbonitriles of formula-D. In another way of preparation, the compounds of formula-C are reacted in-situ generated ethoxy methylenemalononitrile by reacting triethyl orthoformate and maolononitrile to obtain novel N-substituted phenyl-5-amino-1H-pyrazole-4-carbonitriles of formula-D. The temperature conditions range from 40° C. to 100° C.

C. to obtain novel N-substituted phenyl-5-amino-1H-pyrazole-4-carboxamide of formula F. The temperature conditions range from 150° C. to 220° C.

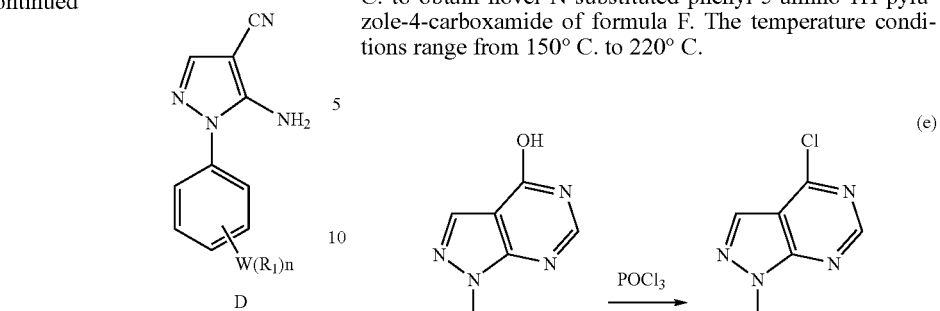

The compound of formula F is reacted with phosphorus oxychloride in an aprotic solvent such as methylene chloride, ethylene chloride, chloroform or a mixture of these solvents at reflux temperature conditions to obtain novel N-substituted 4-chloro-pyrazolo[3,4-d]pyrimidines of formula-G. In another way of preparation, compounds of formula-F are reacted with thionyl chloride, phosphorous trichloride or phosphorous pentachloride in aprotic solvents such as methylene chloride, ethylene chloride, chloroform or mixture of these solvents at 25° C. to solvent reflux temperature to obtain novel N-substituted 4-chloro-pyrazolo[3,4-d]pyrimidines of formula-G.

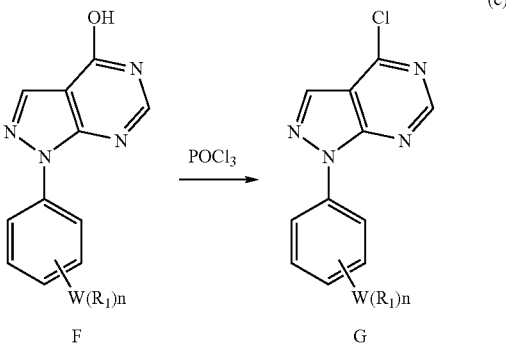

The nitrile group of compound of formula D is hydrolysed with a mineral acid such as sulphuric acid in aqueous medium and upon basification with a suitable base such as ammonia or bicarbonates, carbonates or hydroxides of alkali metals at temperatures 10° C. to 40° C. to obtain novel N-substituted phenyl-5-amino-1H-pyrazole-4-carboxamides of formula-E.

The compound of formula E is reacted with formamide in neat conditions or in solvent such as sulfolane at about 200°

The compound of formula G is refluxed with substituted alkyl amine of formula-H in a protic solvent such as methanol, ethanol, isopropyl alcohol or mixture of these solvents at reflux temperature to obtain novel 1-substituted 4-amino substituted-pyrazolo[3,4-d]pyrimidines of formula-1.

Further, the compounds of Formula-I with an ethynyl substitution on the N-phenyl ring and their pharmaceutically acceptable salts thereof may be prepared by any process known to be applicable to the chemically related compounds. The active compounds of present invention with an ethynyl substitution on the N-phenyl ring can be synthesized as per the process given in the Scheme-II below.

Stage-I

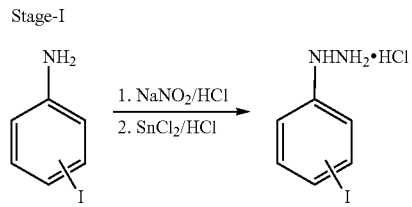

Stage-II

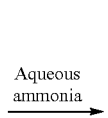

Stage-III

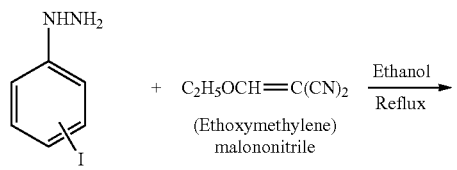

Stage-IV

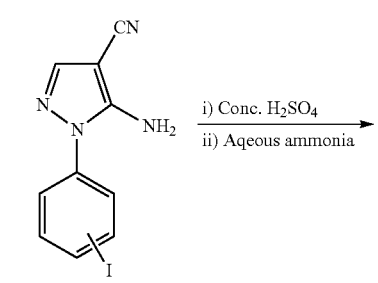

Stage-V

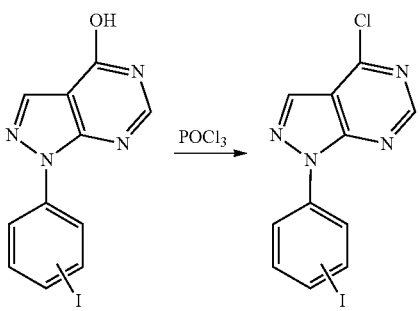

Stage-VI

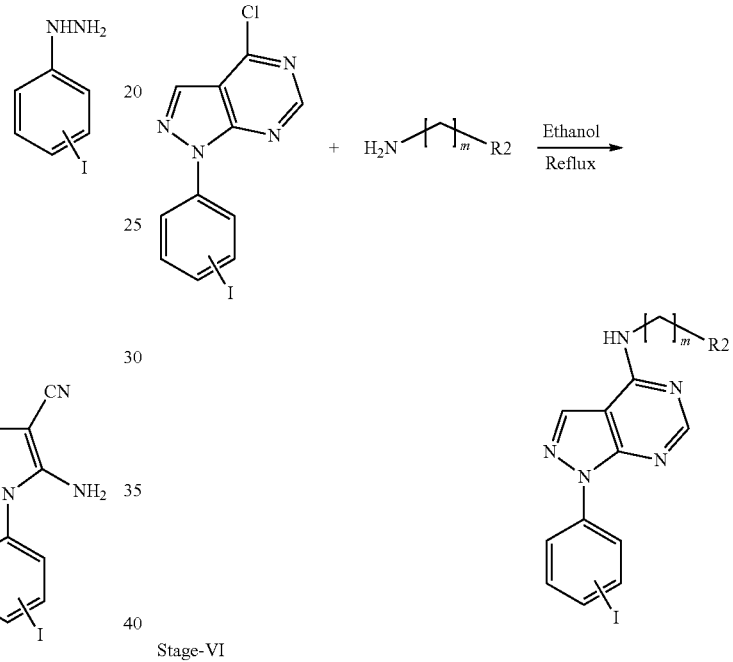

Stage-VI

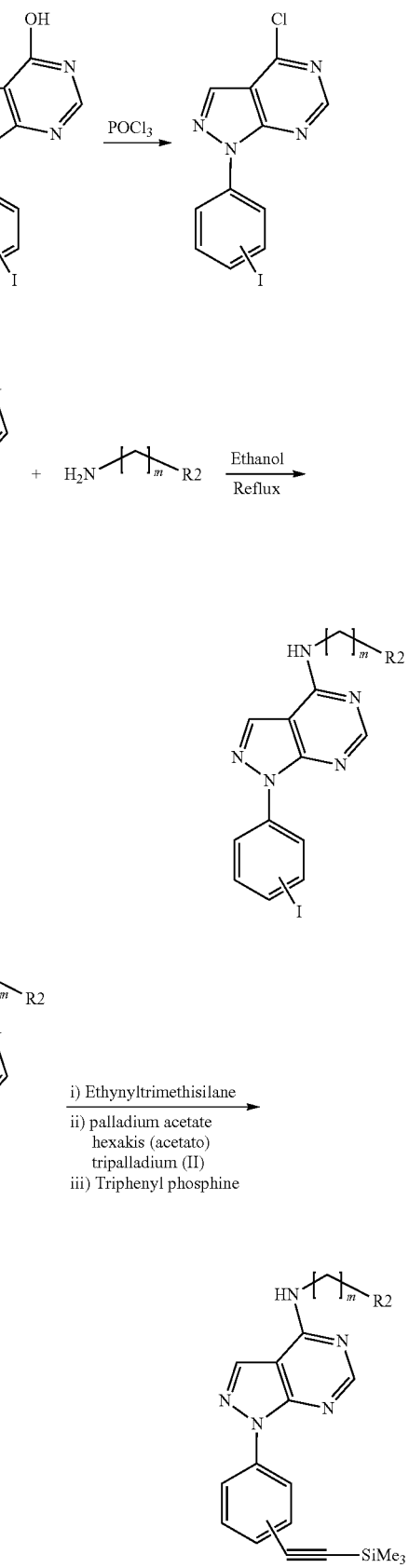

Stage-VIII

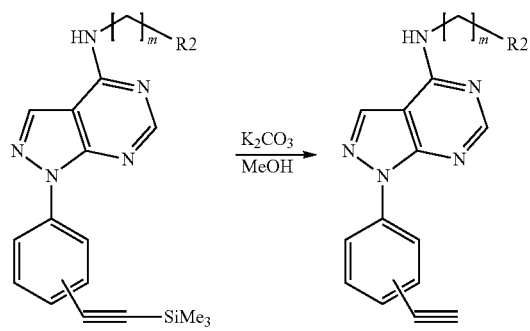

SCHEME-II

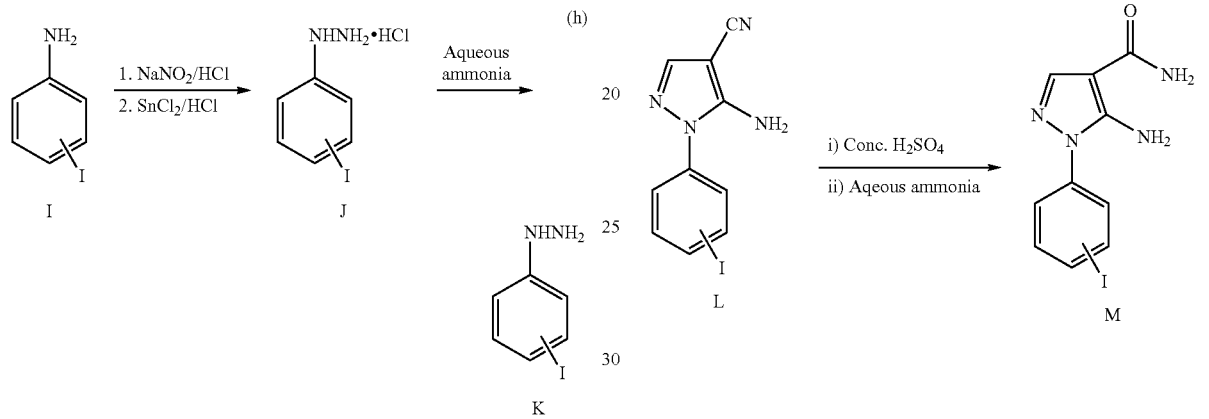

By known methods given in the literature, diazotising a compound of formula I with mineral acid such as hydrochloric acid and with sodium nitrite solution at temperatures −10° C. to 5° C. one can obtain iodo substituted phenyl hydrazine hydrochloride solid of formula-J. The other mineral acids which can be used are sulphuric acid, etc. The compound of formula-J is neutralized with a suitable base such as sodium hydroxide, potassium hydroxide, sodium carbonate, potassium carbonate ammonium carbonate and bicarbonates of alkali metals to get the iodo substituted phenyl hydrazine of formula-K.

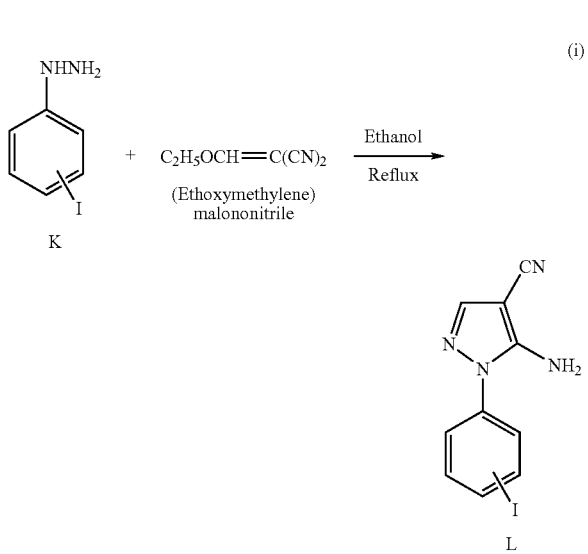

The compound of formula K is reacted with ethoxy methelenemalononitrile in protic solvents such as methanol, ethanol, isopropanol n-butanol, dimethyl formamide or mixtures of these solvents at temperatures 60° C. to obtain novel N-(iodo substituted) phenyl-5-amino-1H-pyrazole-4-carbonitriles of formula-L In another way of preparation the compounds of formula-K are reacted in-situ generated ethoxymethylenemalononitrile by reacting triethyl orthoformate and malononitrile to obtain novel N-(iodo substituted)phenyl-5-amino-1H-pyrazole-4-carbonitriles of formula-L the temperature conditions range from 40° C. To 100° C.

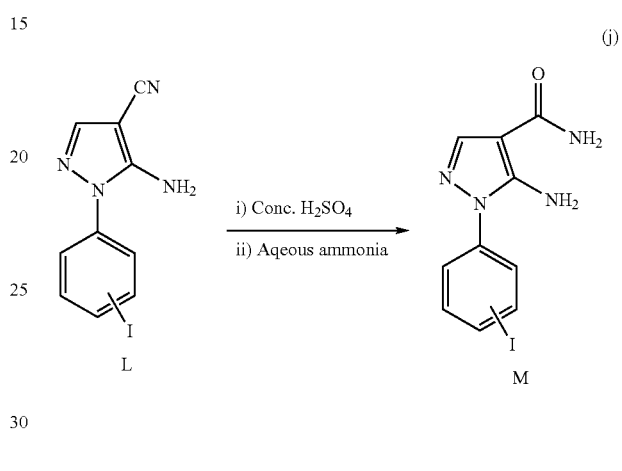

The nitrile group of compounds of formula L is hydrolysed with a mineral acid such as sulphuric acid in aqueous medium and upon basification with a suitable base such as ammonia or bicarbonates, carbonates or hydroxides of alkali metals at temperatures 10° C. to 40° C. to obtain novel N-(iodo substituted) phenyl-5-amino-1H-pyrazole-4-carboxamides of formula-M.

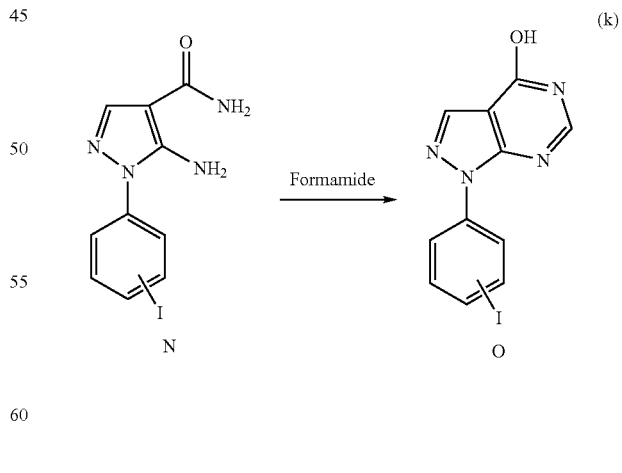

The compound of formula-N is reacted with formamide in neat conditions or in solvent such as sulfolane at temperatures 200° C. to obtain novel N-(iodo substituted) phenyl-5-amino-1H-pyrazole-4-carboxamide of formula-O. The temperature conditions range from 150° C. to 220° C.

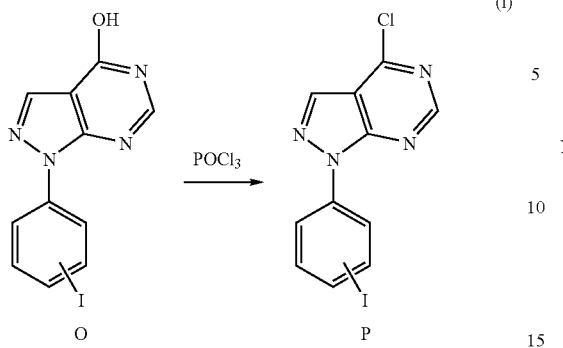

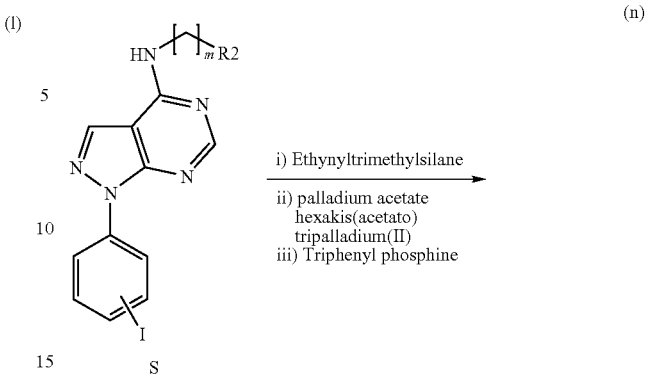

The compounds of formula O are reacted with phosphorus oxychloride in neat conditions or in aprotic solvents such as methylene chloride, ethylene chloride, chloroform or mixtures of these solvents at reflux temperature conditions to obtain novel N-(iodo substituted) 4-chloro-pyrazolo[3,4-d]pyrimidines of formula-P. In another way of preparation of the compounds of formula-O are reacted with thionyl chloride, phosphorous trichloride or phosphorous pentachloride in aprotic solvents such as methylene chloride, ethylene chloride, chloroform or mixtures of these solvents at temperatures 25° C. to obtain novel N-substituted 4-chloro-pyrazolo[3,4-d]pyrimidines of formula-P.

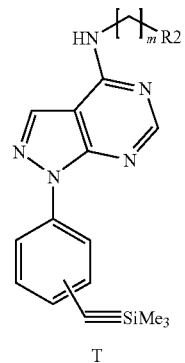

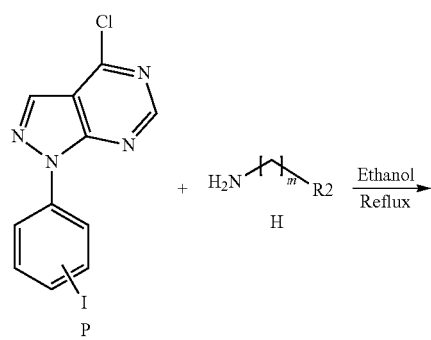

The compound of formula S is refluxed with substituted trimethylsilyl acetylene in protic solvents such as methanol, ethanol, isopropyl alcohol or mixtures of these solvents at reflux temperature conditions to obtain novel N-(trimethyl silyl protected ethynyl substituted) phenyl-4-amino substituted-pyrazolo[3,4-d]pyrimidines of formula-T.

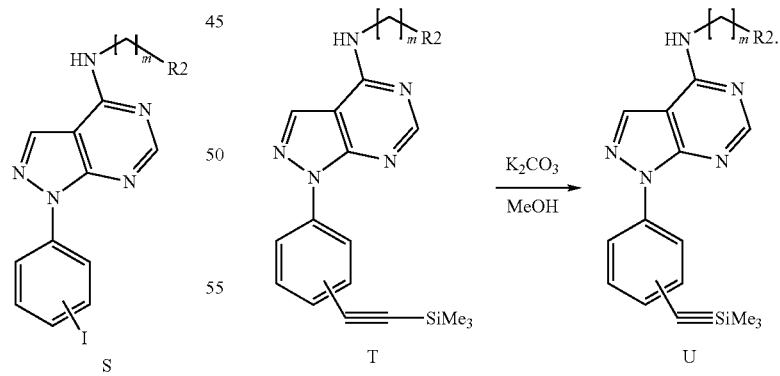

(Formula-I compounds with acetylene group)

By known methods given in the literature, the compound of formula Q is refluxed with substituted alkyl amine of formula-H in protic solvents such as methanol, ethanol, isopropyl alcohol or mixtures of these solvents at reflux temperature conditions to obtain novel 1-(iodo substituted) substituted 4-amino substituted-pyrazolo[3,4-d]pyrimidines of formula-S.

The compounds of formula T are deprotected with a suitable base such as ammonia, mono, di or trialkylamines, sodium hydroxide, potassium hydroxide, sodium carbonate, potassium carbonate ammonium carbonate and bicarbonates of alkali metals to get the novel acetylene substituted compounds of formula-1.

The active compounds of present invention with a cyano substitution on the N-phenyl ring can be synthesized as per the process given in the Scheme-III below.

Scheme-III

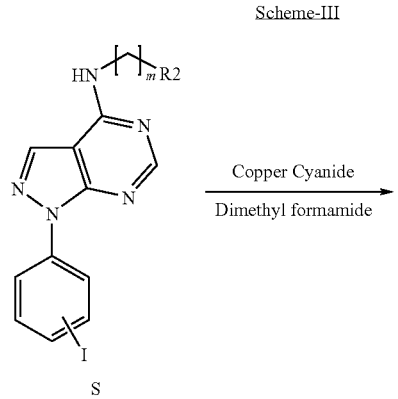

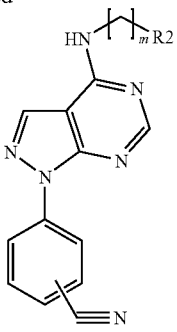

(Formula-I compounds with cyano group)

The compound of formula S is heated with copper cyanide and copper iodide in dimethyl formamide or dimethyl sulfoxide at temperatures ranging from 120° C. to 145° C. to obtain novel compounds N-(cyano substituted) phenyl-4-amino substituted-pyrazolo[3,4-d]pyrimidines of formula-V.

The invention most particularly relates to compounds of the formula I selected from the group consisting of

[1-(3-ethynyl-phenyl)-1H-pyrazolo[3,4-d]pyrimidine Derivatives of Formula-U

| Compound Number | Structure | Chemical name |
|---|---|---|
| 01 | 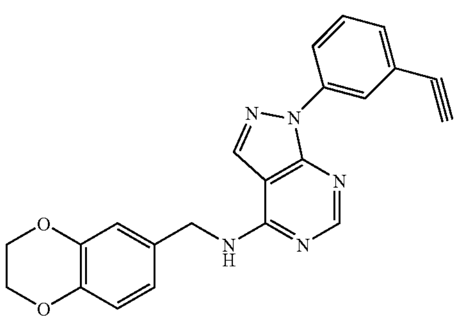 [SMILES: C#Cc1cccc(-n2ncc3c(NCc4ccc5c(c4)OCCO5)ncnc32)c1] | N-((2,3-dihydrobenzo[b][1,4]dioxin-6-yl)methyl)-[1-(3-ethynyl-phenyl)-1H-pyrazolo[3,4-d]pyrimidin-4-yl-amine |
| 02 | 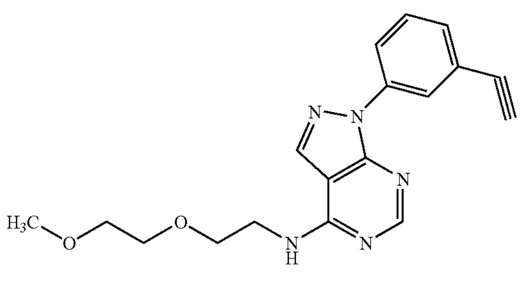 [SMILES: C#Cc1cccc(-n2ncc3c(NCCOCCOC)ncnc32)c1] | [2-(2-methoxy-ethoxy)-ethyl]-[1-(3-ethynyl-phenyl)-1H-pyrazolo[3,4-d]pyrimidin-4-yl)-amine |
| 03 | 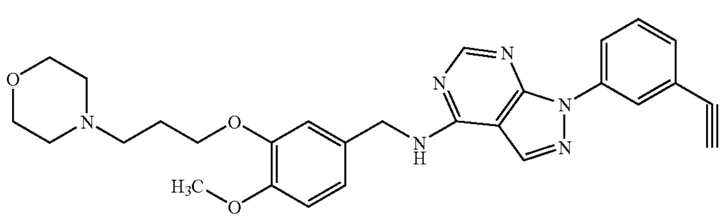 [SMILES: C#Cc1cccc(-n2ncc3c(NCc4ccc(OC)c(OCCCN5CCOCC5)c4)ncnc32)c1] | [4-Methoxy-3-(3-morpholine-4-yl-propoxy)-benzyl]-[1-(3-ethynyl-phenyl)-1H-pyrazolo[3,4-d]pyrimidine-4-yl)-amine |

| Compound Number | Structure | Chemical name |
|---|---|---|
| 04 | 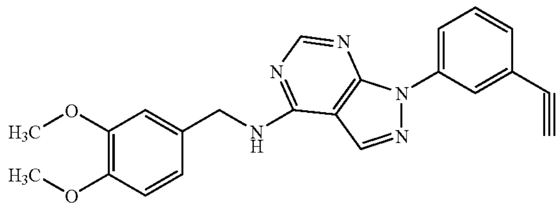 [SMILES: C#Cc1cccc(-n2ncc3c(NCc4ccc(OC)c(OC)c4)ncnc32)c1] | (3,4-Dimethoxy-benzyl)-[1-(3-ethynyl-phenyl)1H-pyrazolo[3,4-d]pyrimidine-4-yl)-amine |
| 05 | 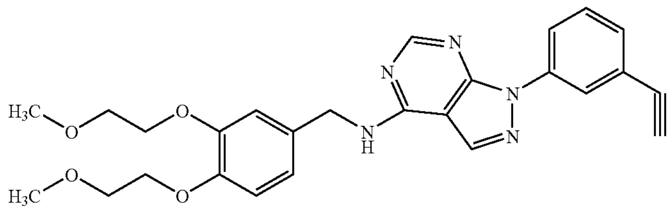 [SMILES: C#Cc1cccc(-n2ncc3c(NCc4ccc(OCCOC)c(OCCOC)c4)ncnc32)c1] | [3,4-Bis-(2-methoxy-ethoxy)-benzyl[1-(3-ethynyl-phenyl)-1H-pyrazolo[3,4-d]pyrimidine-4-yl)-amine |
| 06 | 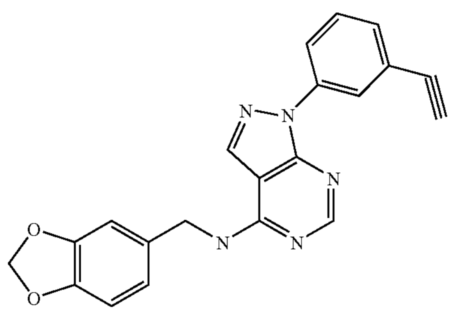 [SMILES: C#Cc1cccc(-n2ncc3c(NCc4ccc5c(c4)OCO5)ncnc32)c1] | Benzo[1,3]dioxol-5-yl methyl-[1-(3-ethynyl-phenyl)-1-H-pyrazolo[3,4-d]pyrimidine-4-yl]-amine |
| 07 | 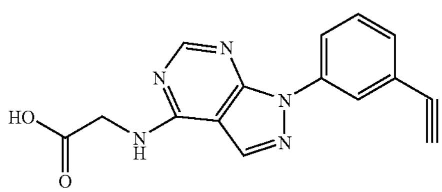 | [1-(3-ethynyl-phenyl)-1H-pyrazolo[3,4-d]pyrimidine-4-ylamino)-acetic acid |
| 08 | 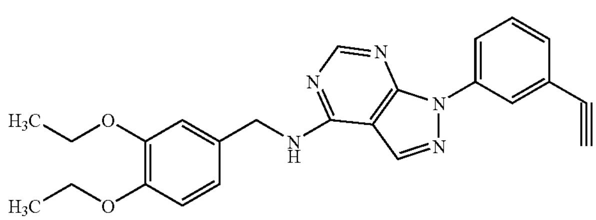 [SMILES: C#Cc1cccc(-n2ncc3c(NCc4ccc(OCC)c(OCC)c4)ncnc32)c1] | 3,4-Diethoxy-benzyl-[1-(3-ethynyl-phenyl)-1H-pyrazolo[3,4-d]pyrimidine-4-yl)-amine |
| 09 | 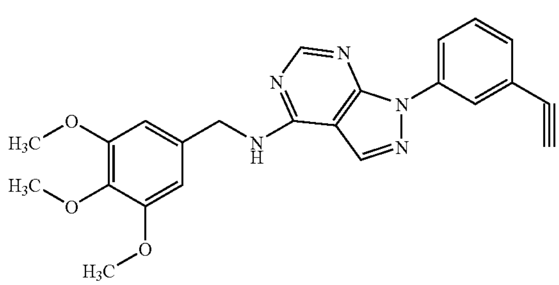 [SMILES: C#Cc1cccc(-n2ncc3c(NCc4cc(OC)c(OC)c(OC)c4)ncnc32)c1] | [1-(3-ethynyl-phenyl)-1H-pyrazolo[3,4-d]pyrimidine-4yl)-(3,4,5-trimethoxy-benzyl)-amine |

-continued

| Compound Number | Structure | Chemical name |
|---|---|---|
| 10 | 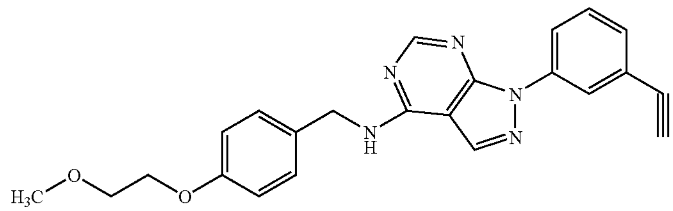 [SMILES: C#Cc1cccc(-n2ncc3c(NCc4ccc(OCCOC)cc4)ncnc32)c1] | [4-(2-methoxy-ethoxy)-benzyl]-[1-(3-ethynyl-phenyl)-1H-pyrazolo[3,4-d]pyrimidine-4-yl]-amine |
| 11 | 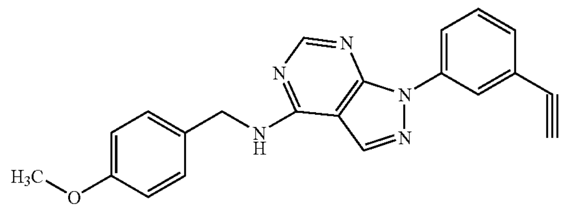 [SMILES: C#Cc1cccc(-n2ncc3c(NCc4ccc(OC)cc4)ncnc32)c1] | (4-methoxy-benzyl-[1-(3-ethynyl-phenyl)1H-pyrazolo[3,4-d]pyrimidine-4-yl)-amine |
| 12 | 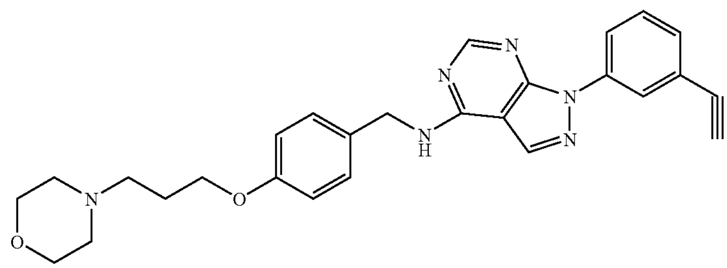 [SMILES: C#Cc1cccc(-n2ncc3c(NCc4ccc(OCCCN5CCOCC5)cc4)ncnc32)c1] | [4-(3-morpholin-4-yl-propoxy)-benzyl]-[1-(3-ethynyl-phenyl)-1H-pyrazolo[3,4-d]pyrimidine-4-yl)-amine |

[1-(3-trimethylsilanyl ethynyl-phenyl)-1H-pyrazolo[3,4-d]pyrimidine Derivatives of Formula-T

| Compound Number | Structure | Chemical name |
|---|---|---|
| 13 | 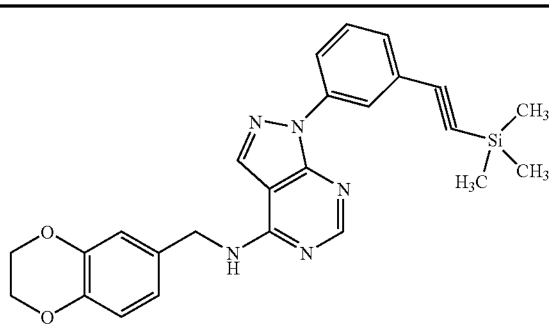 | N-((2,3-dihydrobenzo[b][1,4]dioxin-6-yl)methyl)-[1-(3-trimethylsilanyl ethynyl-phenyl)-1H-pyrazolo[3,4-d]pyrimidin-4-yl-amine |
| 14 | 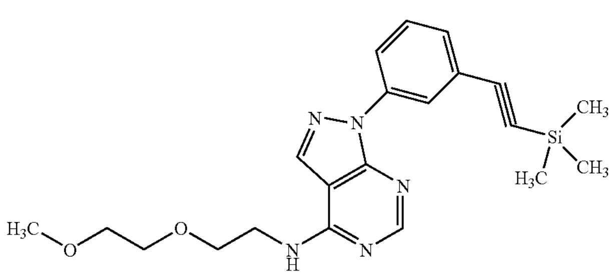 | [2-(2-methoxy-ethoxy)-ethyl]-[1-(3-trimethylsilanyl ethynyl-phenyl)-1H-pyrazolo[3,4-d]pyrimidin-4-yl)-amine |

-continued

| Compound Number | Structure | Chemical name |
|---|---|---|
| 15 | 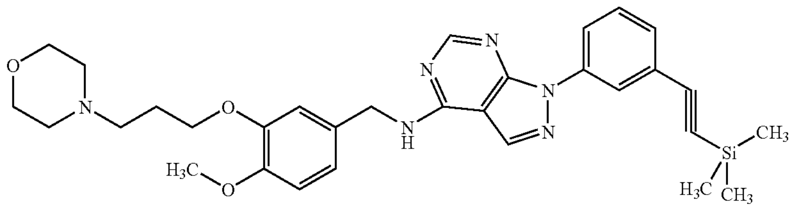 [SMILES: COc1ccc(CNc2ncnc3c2cnn3-c2cccc(C#C[Si](C)(C)C)c2)cc1OCCCN1CCOCC1] | [4-Methoxy-3-(3-morpholine-4-yl-propoxy)-benzyl]-[1-(3-trimethylsilanyl ethynyl-phenyl)1H-pyrazolo[3,4-d]pyrimidine-4-yl)-amine |
| 16 | 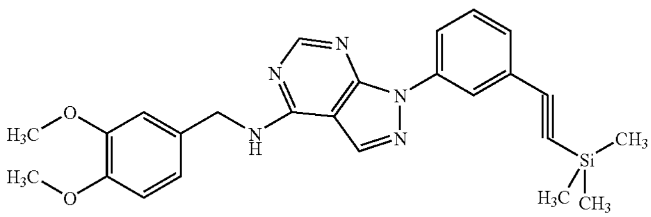 | (3,4-Dimethoxy-benzyl)-[1-(3-trimethylsilanyl ethynyl-phenyl)-1H-pyrazolo[3,4-d]pyrimidine-4-yl)-amine |
| 17 | 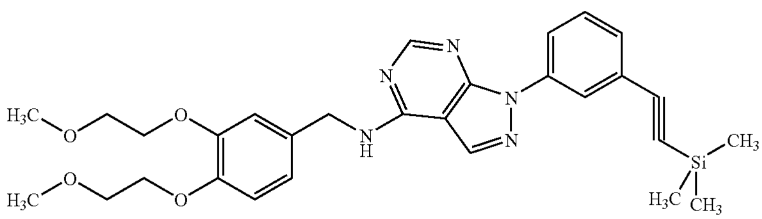 | [3,4-Bis-(2-methoxy-ethoxy)-benzyl[1-(3-trimethylsilanyl ethynyl-phenyl)-1H-pyrazolo[3,4-d]pyrimidine-4-yl)-amine |
| 18 | 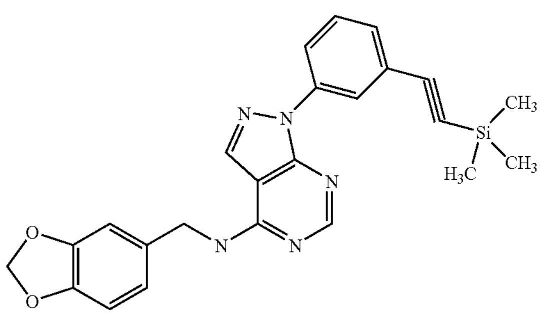 [SMILES: C[Si](C)(C)C#Cc1cccc(-n2ncc3c(NCc4ccc5c(c4)OCO5)ncnc32)c1] | Benzo[1,3]dioxol-5-yl methyl-[1-(3-trimethylsilany ethynyl-phenyl)-1-H-pyrazolo[3,4-d]pyrimidine-4-yl]-amine |
| 19 | 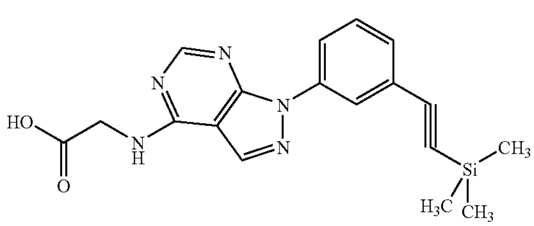 [SMILES: C[Si](C)(C)C#Cc1cccc(-n2ncc3c(NCC(=O)O)ncnc32)c1] | [1-(3-trimethylsilanyl ethynyl-phenyl)-1H-pyrazolo[3,4-d]pyrimidine-4-ylamino)-acetic acid |
| 20 | 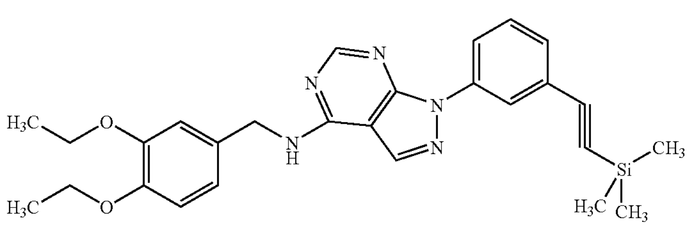 [SMILES: CCOc1ccc(CNc2ncnc3c2cnn3-c2cccc(C#C[Si](C)(C)C)c2)cc1OCC] | 3,4-Diethoxy-benzyl-[1-(3-trimethylsilanyl ethynyl-phenyl)-1H-pyrazolo[3,4-d]pyrimidine-4-yl)-amine |

-continued

| Compound Number | Structure | Chemical name |
|---|---|---|
| 21 | 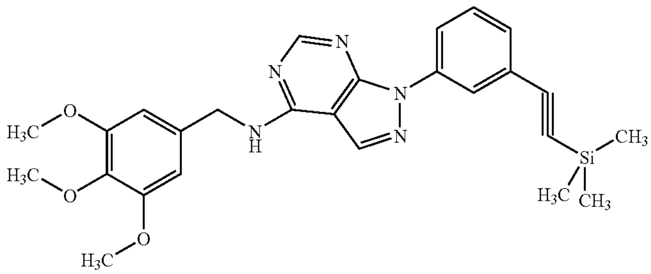 | [1-(3-trimethylsilanyl ethynyl-phenyl)-1H-pyrazolo[3,4-d]pyrimidine-4-yl)-(3,4,5-trimethoxy-benzyl)-amine |
| 22 | 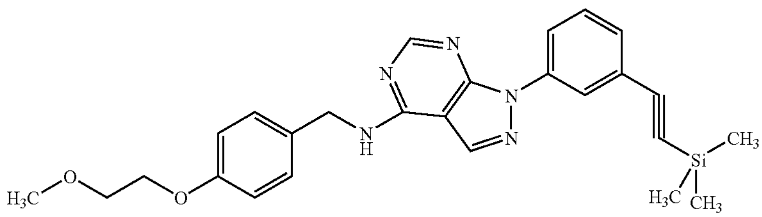 | [4-(2-methoxy-ethoxy)-benzyl]-[1-(3-trimethylsilanyl ethynyl-phenyl)-1H-pyrazolo[3,4-d]pyrimidine-4-yl)-amine |
| 23 | 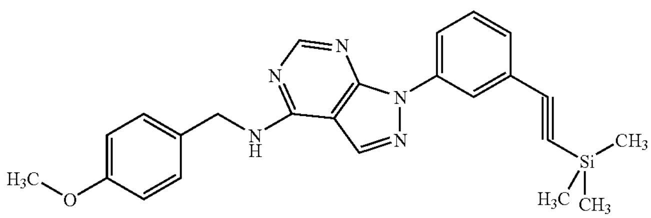 | (4-methoxy-benzyl-[1-(3-trimethylsilanyl ethynyl-phenyl)-1H-pyrazolo[3,4-d]pyrimidine-4-yl)-amine |
| 24 | 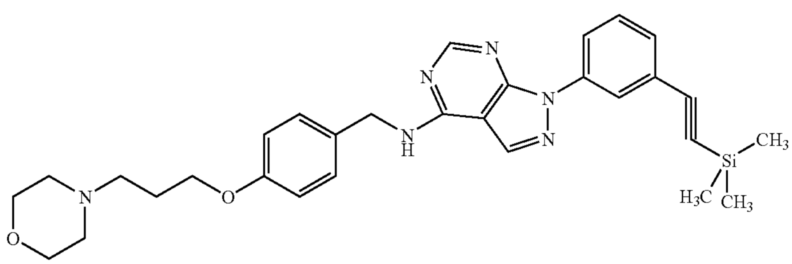 [SMILES: C[Si](C)(C)C#Cc1cccc(-n2ncc3c(NCc4ccc(OCCCN5CCOCC5)cc4)ncnc32)c1] | [4-(3-morpholin-4-yl-propoxy)-benzyl]-[1-(3-trimethylsilanyl ethynyl-phenyl)-1H-pyrazolo[3,4-d]pyrimidine-4-yl)-amine |

3-iodophenyl-1H-pyrazolo[3,4-d]pyrimidine
Derivatives of Formula-S

| Compound Number | Structure | Chemical name |
|---|---|---|
| 25 | 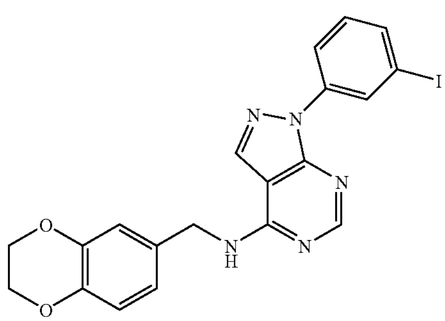 [SMILES: Ic1cccc(-n2ncc3c(NCc4ccc5c(c4)OCCO5)ncnc32)c1] | N-((2,3-dihydrobenzo[b][1,4]dioxin-6-yl)methyl)-[1-(3-iodo-phenyl)-1H-pyrazolo[3,4-d]pyrimidin-4-yl-amine |

-continued

| Compound Number | Structure | Chemical name |
|---|---|---|
| 26 | 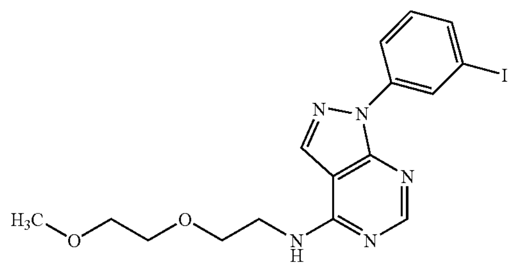 [SMILES: COCCOCCNc1ncnc2c1cnn2-c1cccc(I)c1] | [2-(2-methoxy-ethoxy)-ethyl]-[1-(3-iodo-phenyl)-1H-pyrazolo[3,4-d]pyrimidin-4-yl)-amine |
| 27 | 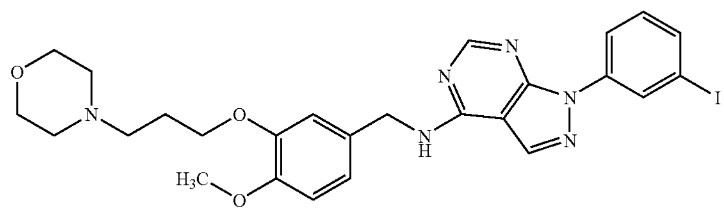 [SMILES: COc1ccc(CNc2ncnc3c2cnn3-c2cccc(I)c2)cc1OCCCN1CCOCC1] | [4-Methoxy-3-(3-morpholine-4-yl-propoxy)-benzyl]-[1-(3-iodo-phenyl)-1H-pyrazolo[3,4-d]pyrimidine-4-yl)-amine |
| 28 | 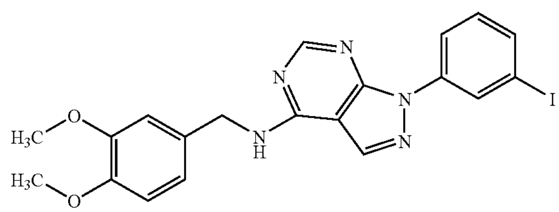 [SMILES: COc1ccc(CNc2ncnc3c2cnn3-c2cccc(I)c2)cc1OC] | (3,4-Dimethoxy-benzyl)-[1-(3-iodo-phenyl)1H-pyrazolo[3,4-d]pyrimidine-4-yl)-amine |
| 29 | 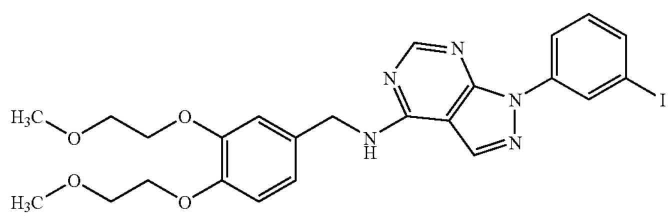 [SMILES: COCCOc1ccc(CNc2ncnc3c2cnn3-c2cccc(I)c2)cc1OCCOC] | [3,4-Bis-(2-methoxy-ethoxy)-benzyl]-[1-(3-iodo-phenyl)-1H-pyrazolo[3,4-d]pyrimidine-4-yl)-amine |
| 30 | 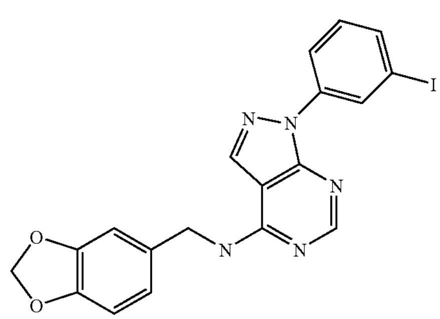 [SMILES: Ic1cccc(-n2ncc3c(NCc4ccc5c(c4)OCO5)ncnc32)c1] | Benzo[1,3]dioxol-5-yl methyl-[1-(3-iodo-phenyl)-1-H-pyrazolo[3,4-d]pyrimidine-4-yl]-amine |
| 31 | 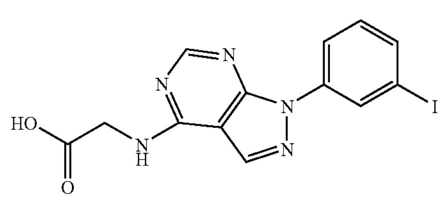 [SMILES: O=C(O)CNc1ncnc2c1cnn2-c1cccc(I)c1] | [1-(3-iodo-phenyl)-1H-pyrazolo[3,4-d]pyrimidine-4-ylamino)-acetic acid |

-continued

| Compound Number | Structure | Chemical name |
|---|---|---|
| 32 | 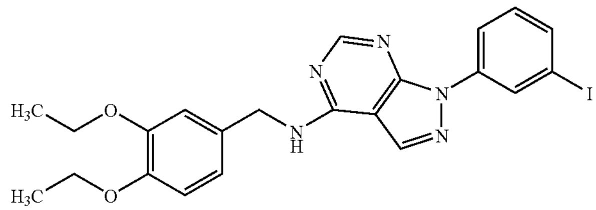 [SMILES: CCOc1ccc(CNc2ncnc3c2cnn3-c2cccc(I)c2)cc1OCC] | 3,4-Diethoxy-benzyl)-)-[1-(3-iodo-phenyl)-1H-pyrazolo[3,4-d]pyrimidine-4-yl)-amine |
| 33 | 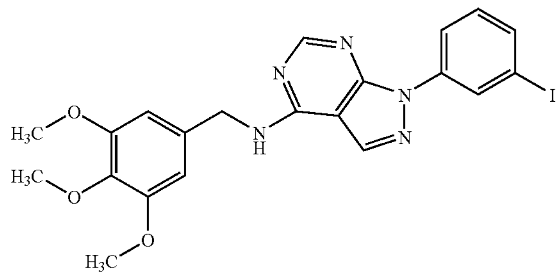 [SMILES: COc1cc(CNc2ncnc3c2cnn3-c2cccc(I)c2)cc(OC)c1OC] | [1-(3-iodo-phenyl)-1H-pyrazolo[3,4-d]pyrimidine-4-yl)-(3,4,5-trimethoxy-benzyl)-amine |
| 34 | 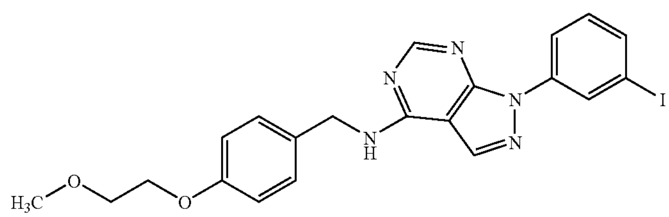 [SMILES: COCCOc1ccc(CNc2ncnc3c2cnn3-c2cccc(I)c2)cc1] | [4-(2-methoxy-ethoxy)-benzyl]-[1-(3-iodo-phenyl)-1H-pyrazolo[3,4-d]pyrimidine-4-yl]-amine |
| 35 | 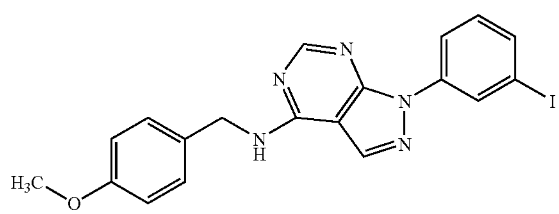 [SMILES: COc1ccc(CNc2ncnc3c2cnn3-c2cccc(I)c2)cc1] | (4-methoxy-benzyl-[1-(3-iodo-phenyl)1H-pyrazolo[3,4-d]pyrimidine-4-yl)-amine |
| 36 | 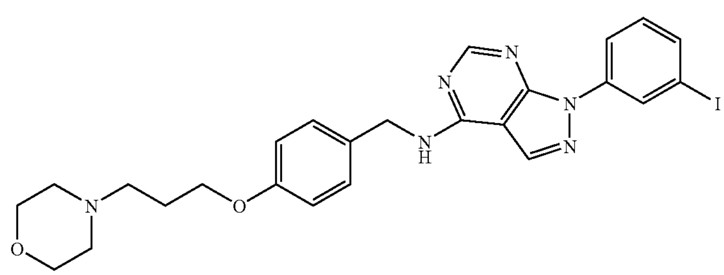 [SMILES: Ic1cccc(-n2ncc3c(NCc4ccc(OCCCN5CCOCC5)cc4)ncnc32)c1] | [4-(3-morpholin-4-yl-propoxy)-benzyl]-[1-(3-iodo-phenyl)-1H-pyrazolo[3,4-d]pyrimidine-4-yl)-amine |

3-Cyano phenyl-1H-pyrazolo[3,4-d]pyrimidine
Derivatives of Formula-V

| Compound Number | Structure | Chemical name |
|---|---|---|
| 37 | 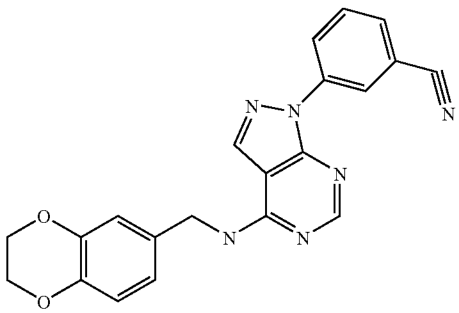 [SMILES: N#Cc1cccc(-n2ncc3c(NCc4ccc5c(c4)OCCO5)ncnc32)c1] | 3-{4-[(2,3-Dihydro-benzo[1,4]dioxin-6-ylmethyl)-amino]-pyrazolo[3,4-d]pyrimidin-1-yl}-benzonitrile |
| 38 | 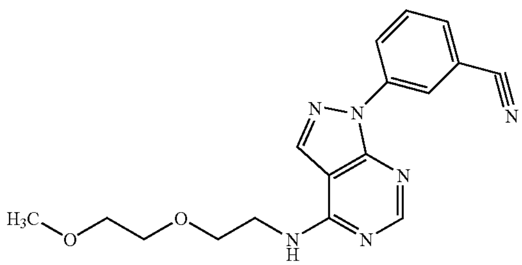 [SMILES: COCCOCCNc1ncnc2c1cnn2-c1cccc(C#N)c1] | 3-{4-[2-(2-methoxy-ethoxy)-ethylamino]-pyrazolo[3,4-d]-1-yl}-benzonitrile |
| 39 | 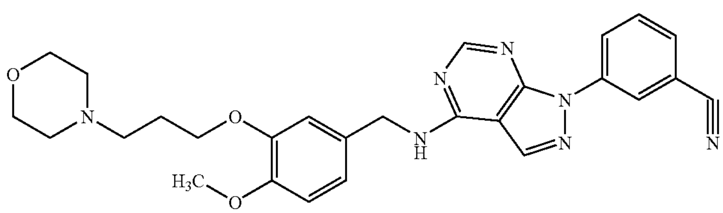 [SMILES: COc1ccc(CNc2ncnc3c2cnn3-c2cccc(C#N)c2)cc1OCCCN1CCOCC1] | 3-{4-[4-methoxy-3-(3-morpholin-4-yl-propoxy)-benzyl amino]-pyrazolo[3,4-d]pyrimidin-1yl-}-benzonitrile |
| 40 | 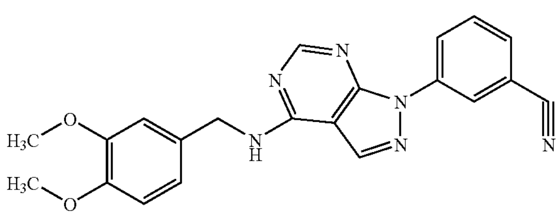 [SMILES: COc1ccc(CNc2ncnc3c2cnn3-c2cccc(C#N)c2)cc1OC] | 3-[4-(3,4-dimethoxy-benzyl amino]-pyrazolo[3,4-d]pyrimidin-1-yl-}-benzonitrile |
| 41 | 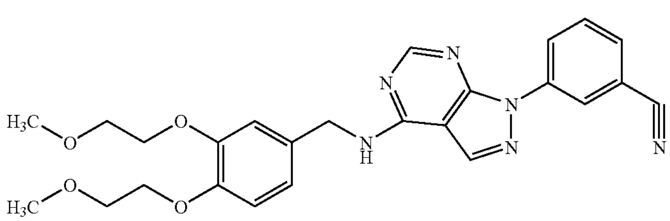 | 3-{4-[3,4-bis-(2-methoxy-ethoxy)-benzyl amino]-pyrazolo[3,4-d]pyrimidin-1-yl-}-benzonitrile |

-continued

| Compound Number | Structure | Chemical name |
|---|---|---|
| 42 | 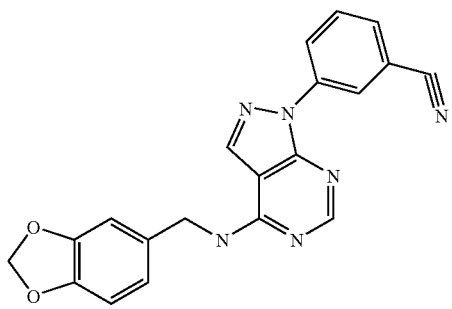 [SMILES: N#Cc1cccc(-n2ncc3c(NCc4ccc5c(c4)OCO5)ncnc32)c1] | 3-{4-[(Benzo[1,3]dioxol-5-yl methyl)-amino-pyrazolo[3,4-d] pyrimidin-1-yl-}-benzonitrile |
| 43 | 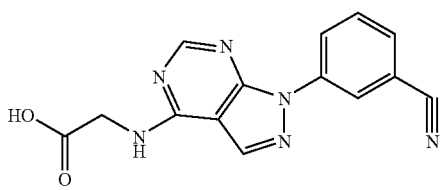 [SMILES: N#Cc1cccc(-n2ncc3c(NCC(=O)O)ncnc32)c1] | [1-(3-cyano-phenyl)-1H-pyrazolo[3,4-d]pyrimidin-4-ylamino]-acetic acid |
| 44 | 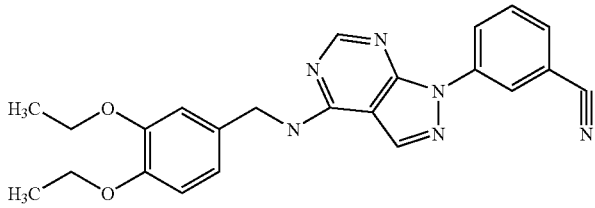 [SMILES: CCOc1ccc(CNc2ncnc3c2cnn3-c2cccc(C#N)c2)cc1OCC] | 3-[4-(3,4-Diethoxy-benzyl amino)-pyrazolo[3,4-d]pyrimidin-1-yl]-benzonitrile |
| 45 | 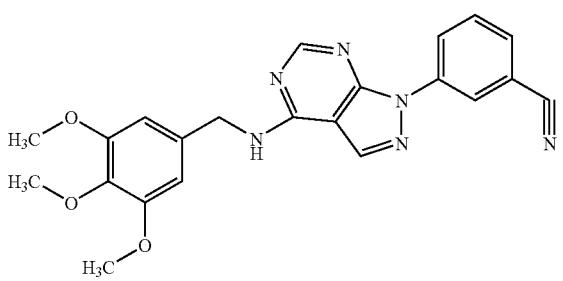 [SMILES: COc1cc(CNc2ncnc3c2cnn3-c2cccc(C#N)c2)cc(OC)c1OC] | 3-[4-(3,4,5-trimethoxy-benzylamino)-pyrazolo[3,4-d]pyrimidin-1-yl]-benzonitrile |
| 46 | 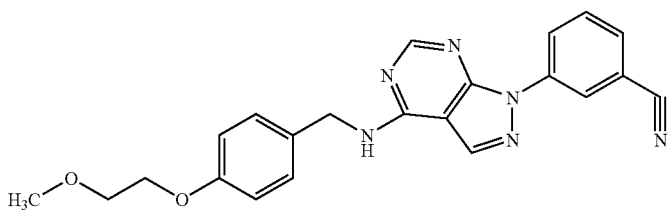 [SMILES: COCCOc1ccc(CNc2ncnc3c2cnn3-c2cccc(C#N)c2)cc1] | 3-{4-[4-(2-methoxy-ethoxy)-benzyl amino]-pyrazolo[3,4-d]pyrimidin-1-yl}-benzonitrile |
| 47 | 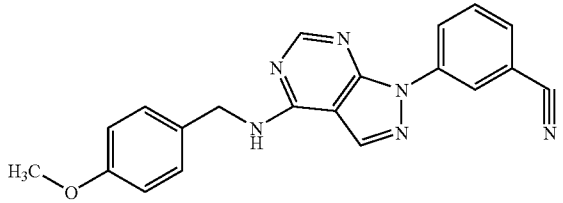 [SMILES: COc1ccc(CNc2ncnc3c2cnn3-c2cccc(C#N)c2)cc1] | 3-[4-(4-methoxy-benzylamino)-pyrazolo[3,4-d]pyrimidin-1-yl]-benzonitrile |

| Compound Number | Structure | Chemical name |
|---|---|---|
| 48 | 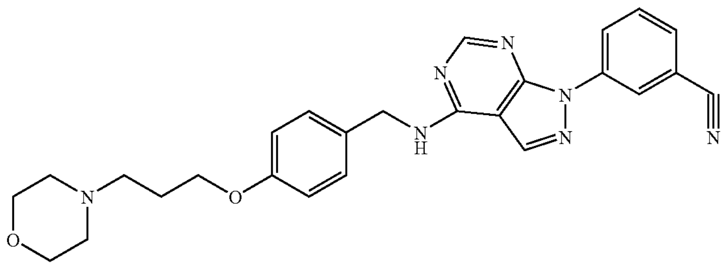 [SMILES: N#Cc1cccc(-n2ncc3c(NCc4ccc(OCCCN5CCOCC5)cc4)ncnc32)c1] | 3-{4-[4-(3-morpholin-4-yl-propoxy)benzyl amino]-pyrazolo[3,4-d]pyrimidin-1-yl}-benzonitrile |

3,5-dimethyl pyrazolo[3,4-d]pyrimidine Derivatives of Formula-I

| Compound Number | Structure | Chemical name |
|---|---|---|
| 49 | 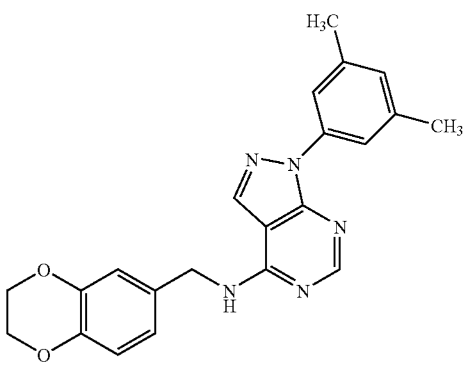 [SMILES: Cc1cc(C)cc(-n2ncc3c(NCc4ccc5c(c4)OCCO5)ncnc32)c1] | N-((2,3-dihydrobenzo[b][1,4]dioxin-6-yl)methyl)-1-(3,5-dimethylphenyl)-1H-pyrazolo[3,4-d]pyrimidin-4-amine |
| 50 | 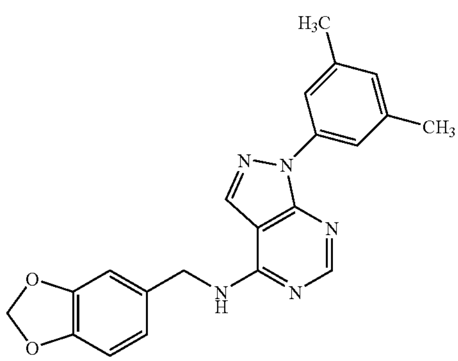 [SMILES: Cc1cc(C)cc(-n2ncc3c(NCc4ccc5c(c4)OCO5)ncnc32)c1] | N-(benzo[d][1,3]dioxol-5-ylmethyl)-1-(3,5-dimethylphenyl)-1H-pyrazolo[3,4-d]pyrimidin-4-amine |
| 51 | 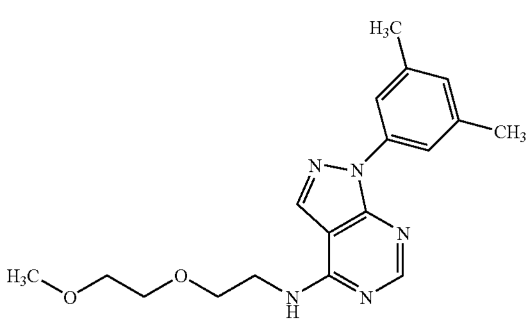 | 1-(3,5-dimethylphenyl)-N-(2-(2-methoxyethoxy)ethyl)-1H-pyrazolo[3,4-d]pyrimidin-4-amine |

-continued

| Compound Number | Structure | Chemical name |
|---|---|---|
| 52 | 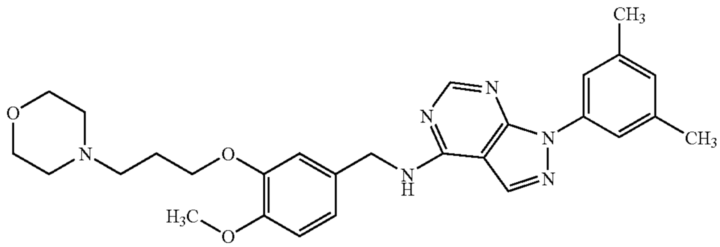 [SMILES: COc1ccc(CNc2ncnc3c2cnn3-c2cc(C)cc(C)c2)cc1OCCCN1CCOCC1] | [1(3,5-dimethyl-phenyl)-1H-pyrazolo[3,4-d]pyrimidine-4-yl]-[4-methoxy-3-(3-morpholin-4-yl-propoxy)-benzyl]-amine |
| 53 | 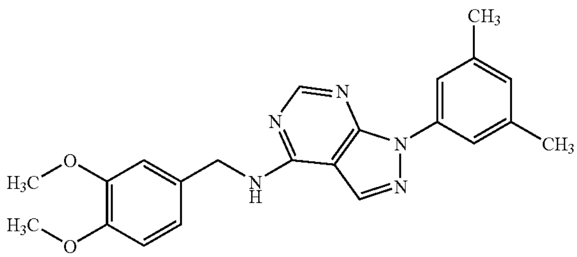 | (3,4-dimethoxy-benzyl)-[1-(3,5-dimethyl-phenyl)-1H-pyrazolo[3,4-d]pyrimidine-4-yl]-amine |
| 54 | 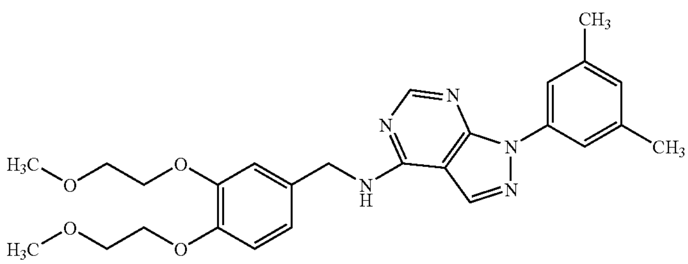 | [3,4-bis-(2-methoxy-ethoxy)-benzyl]-[1-(3,5-dimethyl-phenyl)-1H-pyrazolo[3,4-d]pyrimidin-4-yl]-amine |
| 55 | 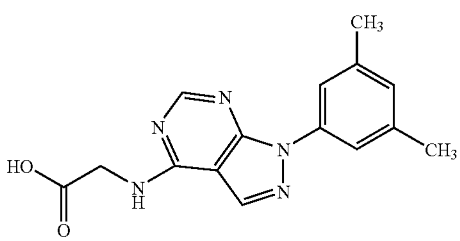 [SMILES: Cc1cc(C)cc(-n2ncc3c(NCC(=O)O)ncnc32)c1] | [1(3,5-dimethyl-phenyl)-1H-pyrazolo[3,4-d]pyrimidin-4-ylamino]acetic acid |
| 56 | 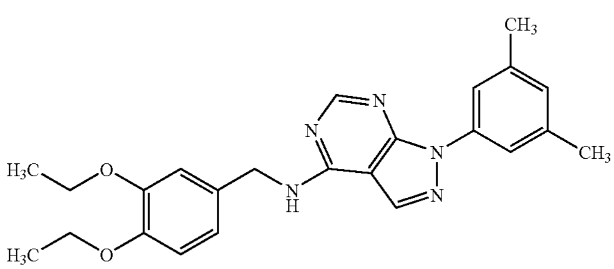 [SMILES: CCOc1ccc(CNc2ncnc3c2cnn3-c2cc(C)cc(C)c2)cc1OCC] | 3,4-diethoxy-benzyl)-[1-(3,5-dimethyl-phenyl)-1H-pyrazolo[3,4-d]pyrimidine-4-yl]-amine |

| Compound Number | Structure | Chemical name |
|---|---|---|
| 57 | 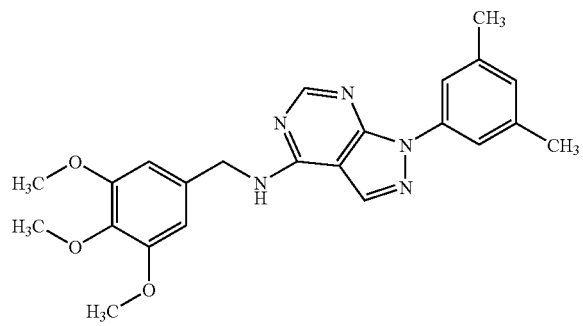 | [1(3,5-dimethyl-phenyl)-1H-pyrazolo[3,4-d]pyrimidin-4-yl]-(3,4,5-trimethoxy-benzyl)-amine |
| 58 | 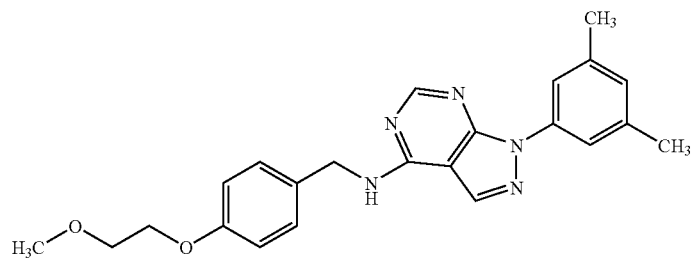 | [1(3,5-dimethyl-phenyl)-1H-pyrazolo[3,4-d]pyrimidin-4-yl]-[4-(2-methoxy-ethoxy)benzyl amine |
| 59 | 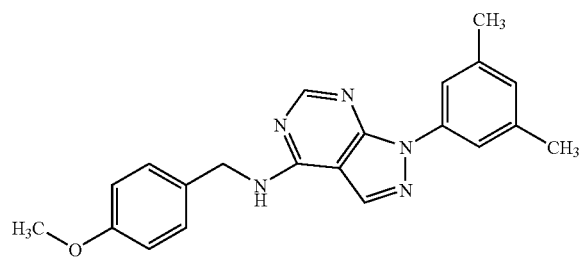 | [1(3,5-dimethyl-phenyl)-1H-pyrazolo[3,4-d]pyrimidin-4-yl]-[4-(methoxy)benzyl amine |
| 60 | 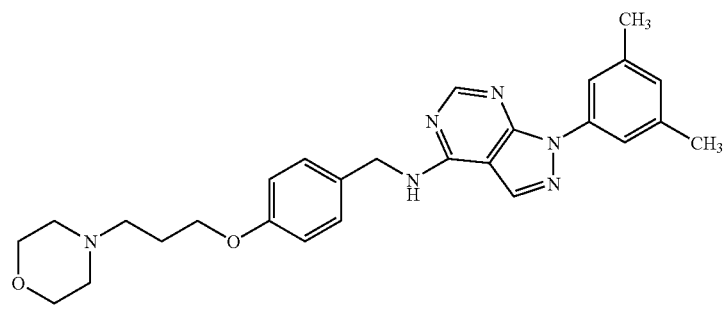 [SMILES: Cc1cc(C)cc(-n2ncc3c(NCc4ccc(OCCCN5CCOCC5)cc4)ncnc32)c1] | [1(3,5-dimethyl-phenyl)-1H-pyrazolo[3,4-d]pyrimidin-4-yl]-[4-(3-morpholine-4-yl-propoxy)benzyl amine | m-tolyl-1H-pyrazolo[3,4-d]pyrimidine Derivatives of Formula-I

| Compound Number | Structure | Chemical name |
|---|---|---|
| 61 | 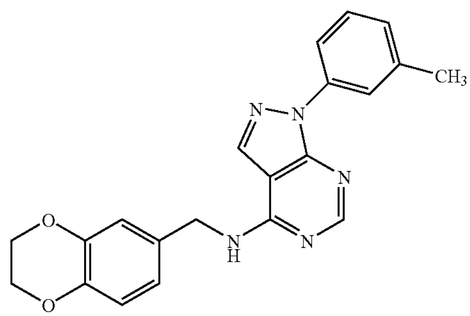 [SMILES: Cc1cccc(-n2ncc3c(NCc4ccc5c(c4)OCCO5)ncnc32)c1] | N-((2,3-dihydrobenzo[b][1,4]dioxin-6-yl)methyl)-1-m-tolyl-1H-pyrazolo[3,4-d]pyrimidin-4-amine |
| 62 | 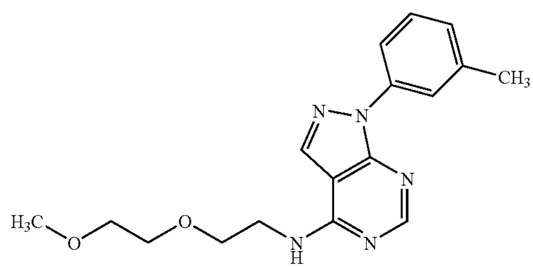 | [2-(2-methoxy-ethoxy)-ethyl]-(1-m-tolyl-1H-pyrazolo[3,4-d]pyrimidine-4-yl)-amine |
| 63 | 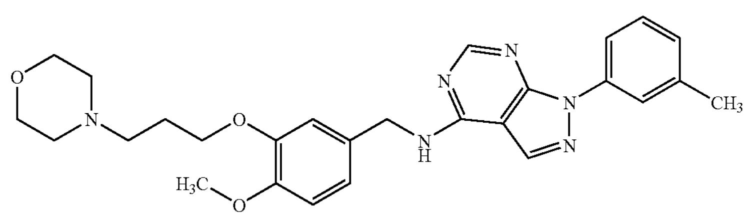 [SMILES: COc1ccc(CNc2ncnc3c2cnn3-c2cccc(C)c2)cc1OCCCN1CCOCC1] | [4-Methoxy-3-(3-morpholine-4-yl-propoxy)-benzyl]-(1-m-tolyl-1H-pyrazolo[3,4-d]pyrimidine-4-yl)-amine |
| 64 | 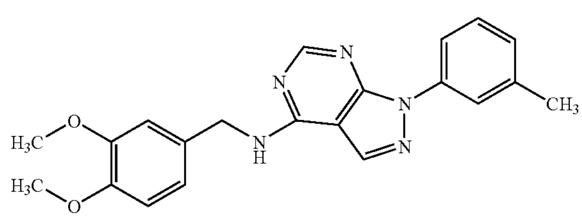 | (3,4-Dimethoxy-benzyl)-(1-m-tolyl-1H-pyrazolo[3,4-d]pyrimidine-4yl)-amine |
| 65 | 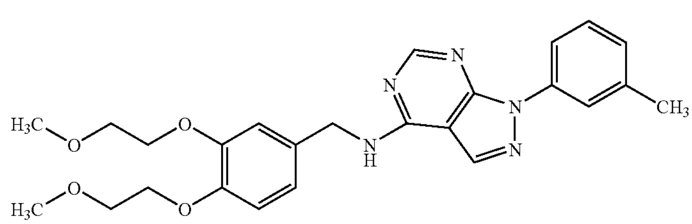 | [3,4-Bis-(2-methoxy-ethoxy)-benzyl]-(1-m-tolyl-1H-pyrazolo[3,4-d]pyrimidine-4-yl)-amine |
| 66 | 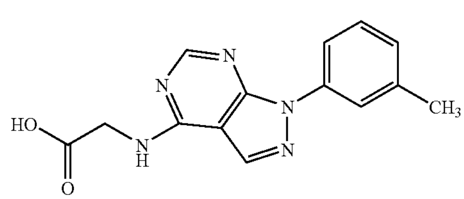 [SMILES: Cc1cccc(-n2ncc3c(NCC(=O)O)ncnc32)c1] | (1-m-tolyl-1H-pyrazolo[3,4-d]pyrimidine-4-ylamino)-acetic acid |

-continued

| Compound Number | Structure | Chemical name |
|---|---|---|
| 67 | 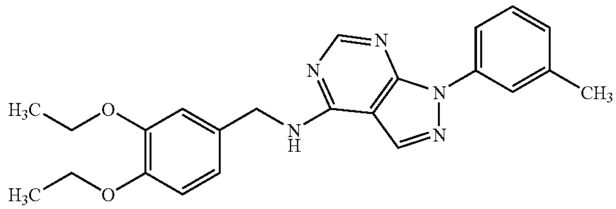 [SMILES: CCOc1ccc(CNc2ncnc3c2cnn3-c2cccc(C)c2)cc1OCC] | 3,4-Diethoxy-benzyl)-(1-m-tolyl-1H-pyrazolo[3,4-d]pyrimidine-4-yl)-amine |
| 68 | 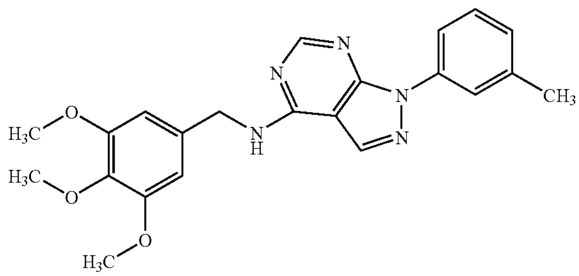 | (1-m-tolyl-1H-pyrazolo[3,4-d]pyrimidine-4-yl)-(3,4,5-trimethoxy-benzyl)-amine |
| 69 | 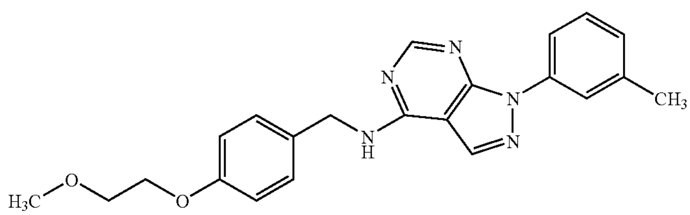 | [4-(2-methoxy-ethoxy)-benzyl]-(1-m-tolyl-1H-pyrazolo[3,4-d]pyrimidine-4-yl)-amine |
| 70 | 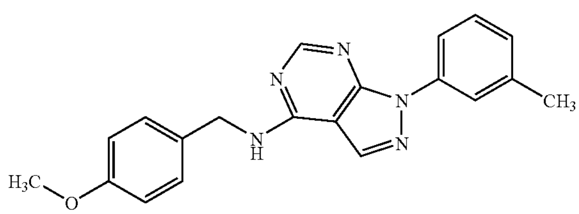 | (4-methoxy-benzyl)-(1-m-tolyl-1H-pyrazolo[3,4-d]pyrimidine-4-yl)-amine |
| 71 | | [4-(3-morpholin-4-yl-propoxy)-benzyl]-(1-m-tolyl-1H-pyrazolo[3,4-d]pyrimidine-4-yl)-amine | i) (1-3-iodo phenyl)-pyrazolo[3,4-d]pyrimidine Derivatives of Formula-J to P

| Compound Number | Structure | Chemical name |
|---|---|---|
| 72 | 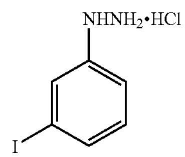 | 1-(3-iodophenyl)-hydrazine hydrochloride |
| 73 | 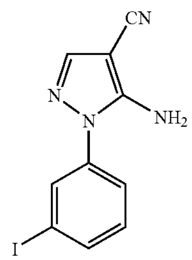 [SMILES: N#Cc1cnn(-c2cccc(I)c2)c1N] | 5-Amino-1-(3-iodophenyl)-1H-pyrazolo-4-carbonitrile |
| 74 | 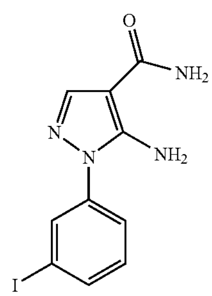 [SMILES: NC(=O)c1cnn(-c2cccc(I)c2)c1N] | 5-Amino-1-(3-iodophenyl)-1H-pyrazolo-4-carboxylic acid amide |
| 75 | 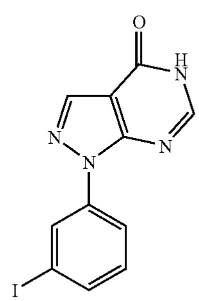 [SMILES: O=c1[nH]cnc2c1cnn2-c1cccc(I)c1] | 1-(3-iodophenyl)-1,5-dihydro-pyrazolo[3,4-d]pyrimidine-4-one |
| 76 | | 4-chloro-1-(3-iodophenyl)-1H-pyrazolo[3,4-d]pyrimidine | ii) 3,5-dimethyl pyrazolo[3,4-d]pyrimidine Derivatives of Formula-E to G

| Compound Number | Structure | Chemical name |
|---|---|---|
| 77 | 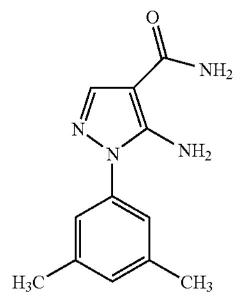 [SMILES: Cc1cc(C)cc(-n2ncc(C(N)=O)c2N)c1] | 5-Amino-1-(3,5-dimethylphenyl)-1H-pyrazole-4-carboxylic acid amide |
| 78 | 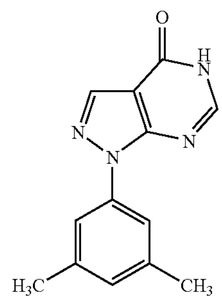 [SMILES: Cc1cc(C)cc(-n2ncc3c(=O)[nH]cnc32)c1] | 1-(3,5-Dimethylphenyl)-1,5-dihydro-pyrazolo[3,4-d]pyrimidine-4-one |
| 79 | | 4-chloro-1-(3,5-dimethyl-phenyl)-1H-pyrazolo[3,4-d]pyrimidine | iii) (1-m-tolyl)-pyrazolo[3,4-d]pyrimidine Derivatives of Formula-E to G

| Compound Number | Structure | Chemical name |
|---|---|---|
| 80 | 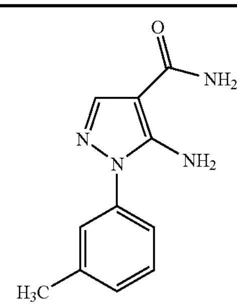 | 5-Amino-1-m-tolyl-1H-pyrazolo-4-carboxylic acid amide |

-continued

| Compound Number | Structure | Chemical name |
|---|---|---|
| 81 | 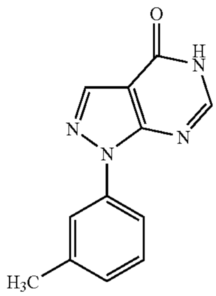 [SMILES: Cc1cccc(-n2ncc3c(=O)[nH]cnc32)c1] | 1-m-Tolyl-1,5-dihydro-pyrazolo[3,4-d]pyrimidine-4-one |
| 82 | 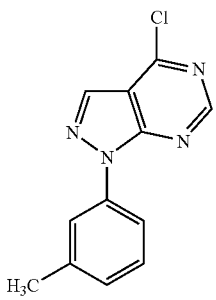 [SMILES: Cc1cccc(-n2ncc3c(Cl)ncnc32)c1] | 4-chloro-1-m-tolyl-1H-pyrazolo[3,4-d]pyrimidine |

In Vitro Studies

MTT Proliferation Assay

MTT [3-(4,5-dimethylthiazol-2-yl)-2,5-diphenyltetrazolium bromide] assay, first described by Mosmann in 1983, is based on the ability of a mitochondrial dehydrogenase enzyme from viable cells to cleave the tetrazolium rings of the pale yellow MTT and form dark blue formazan crystals largely impermeable to cell membranes, thus resulting in its accumulation within healthy cells. Solubilization of the cells by the addition of a detergent results in the liberation of the crystals, which are solubilized. The number of surviving cells is directly proportional to the level of the formazan product created. The color can then be quantified using a simple colorimetric assay. This assay was done using 0-1000 ng/ml concentrations of Erlotinib and its derivatives in A549 and H1299 cells. The protocol was based on ATCC and as per manufacturers instructions (Catalog Number 30-1010K).

Western Blot Analysis

Ideal drug concentrations determined from the MTT proliferation assay were used to treat $1 \times 10^6$ A549 or H1299 cells in appropriate media for 72 h following which cell lysates were extracted and fractionated on a 10% SDS PAGE gel under reducing conditions. The gels were blotted onto treated nylon membranes (Bio-Rad) and immunoprobed for EGFR, PI3K and AKT.

Matrigel Invasion Assay

The in vitro invasiveness of H1299 or A549 cells in the presence of various concentrations of compounds of this invention (as determined by MTT assay) was assessed using a modified Boyden chamber assay. Cells were treated with these compounds for 48 h. $1 \times 10^6$ cells were suspended in 600 µl of serum-free medium supplemented with 0.2% BSA and placed in the upper compartment of the transwell chambers (Corning Costar Fischer Scientific Cat #07-200-158, Pittsburgh Pa.) coated with Matrigel (0.7 mg/ml). The lower compartment of the chamber was filled with 200 µl of serum-medium and the cells were allowed to migrate for 24 h. After incubation, the cells were fixed and stained with Hema-3 and quantified as previously described (Mohanam, et al. 1993). The migrated cells were quantified as percent invasion.

In Vitro Angiogenic Assay

To determine the anti-angiogenic properties of Erlotinib and its derivatives, ideal concentration of drugs were used to treat A549 cells for 72 h as described earlier, after which, complete media was replaced with serum-free media for 12 h. This serum-free media was termed as conditioned media and used for angiogenic induction on HMEC cells grown to 80% confluency as per standard protocols.

In Vivo Studies:

Effect of the Above Mentioned Compounds on Subcutaneous Lung Tumors in Nude Mice Method Nude mice were implanted with $2 \times 10^6$ A549 cells in the right hind limb flank. Upon the observance of a tumor (>2 mm), mice were given oral or ip treatments of Erlotinib, and above-mentioned compounds at $\frac{1}{10}^{th}$ of dose of Erlotinib. From a literature search, 100 mg/kg of Erlotinib had been identified as the base line dose. The select compounds of the present invention caused retardation of tumor growth similar to Erlotinib at $\frac{1}{10}_{th}$ concentration (10-80 ng/ml).

Advantages of Present Invention

1. The above-mentioned novel compounds are superior to the existing standard therapies of non-small cell lung cancers such as Gefitinib and Erlotinib and are potentially useful in lung cancer therapy.

2. The above-mentioned novel compounds are also working on other areas of cancer such as pancreatic cancer and are potentially useful in pancreatic-cancer therapy.

3. The above-mentioned novel compounds are also working on other area such as throat and oral cancer and are potentially useful in throat and oral cancer therapy.

The invention will be more fully described in conjunction with the following specific examples, which are not to be construed as limiting the scope of the invention.

EXPERIMENTAL PROCEDURE

Example—1

Preparation of (2,3-Dihydro-benzo[1,4]dioxin-6-ylmethyl)-[1-(3-ethynyl-phenyl)-1H-pyrazolo[3,4-d]pyrimidine-4-yl]-amine (Compound No. 01)

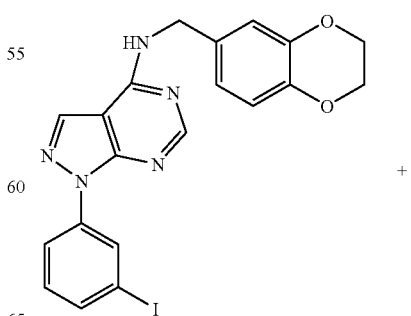

Compound No: 25

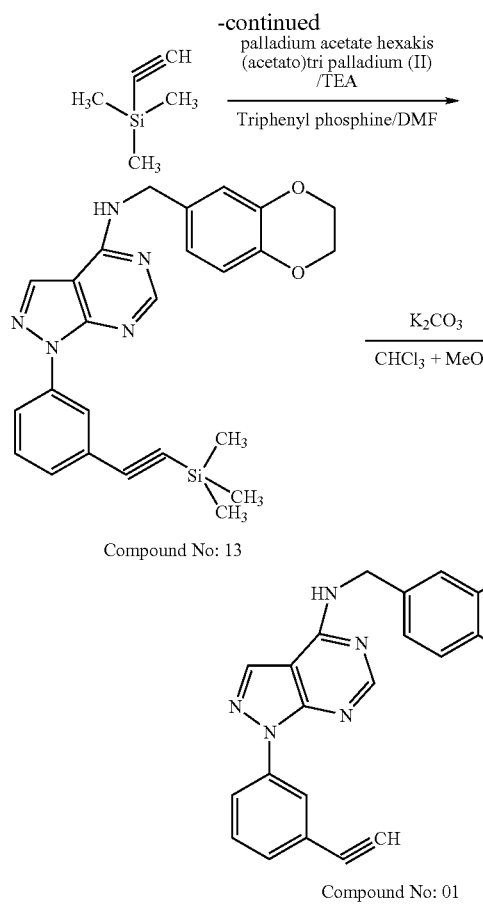

Compound No: 13

Compound No: 01

50 ml of dimethylformamide was charged into a 250 ml 4 necked round bottom flask, connected to a mechanical stirrer, thermometer socket, condenser, addition funnel and nitrogen gas bubbler. 10.0 g (20.60 mmol) of (2,3-Dihydro-benzo[1,4]dioxin-6-yl methyl)-[1-(3-iodo-phenyl)-1H-pyrazolo[3,4-d]pyrimidin-4-yl)amine (Compound No. 25), 14.50 g (0.146 mol) of ethynyl trimethyl silane, 46.0 mg of palladium acetate hexakis(acetato)tri palladium (II) 108.0 mg of triphenyl phosphine and 20.6 ml of triethyl amine were charged. Maintained the mass temperature at 25-35° C. for 30-45 min. Reaction mass temperature was raised to 80-85° C. Maintained the mass temperature at 80-85° C. for 4 hours. Reaction mass temperature was cooled to 50-55° C. and maintained for 2 hours. Reaction mass temperature was cooled to 25-30° C. and maintained for overnight under stirring. Solvent was completely distilled off under vacuum. The crude oil present was dissolved in 160 ml of water and compound was extracted with 300 ml of chloroform. Organic layer was dried with sodium sulphate. Sodium sulphate was filtered and washed the sodium sulphate with 50 ml of chloroform. Distilled off chloroform completely under vacuum. 9.50 g Of crude oil (Compound No. 13) was obtained. Compound was characterized by Mass spectrum [455 (M$^{+1}$)]. 9.0 g of crude oil was dissolved in 85 ml of methanol and 85 ml of chloroform mixture. 11.30 g of potassium carbonate was added. Maintained the mass temperature at 25-35° C. for 14 hours. Distilled of the solvent completely under vacuum. 7.50 g Of crude oil was obtained. Crude oil was purified by the column chromatography with hexane and ethyl acetate mixture as mobile phase. Obtained 3.60 g (yield; 45.70% by theory) of product.

Melting point: 161.0° C.

Spectral Data:

FT-IR (KBr) (cm$^{-1}$); 3365, 3270, 3209, 3085, 3002, 2937, 2872, 2099, 1591, 1575, 1534, 1506, 1491, 1428, 1347, 1232, 1204, 1100, 1064, 788, 724.

400 MHz $^1$H NMR (DMSO-d$_6$) δ value (ppm): 4.19 (s) C≡CH (1H), 4.30 (s) 2 (CH2) (4H) 4.63-4.64 (d) (CH2) (2H), 6.79-6.86 (m) Ar-3H, 7.42-7.55 (d&t) Ar-4H, 8.22-8.24 (d), CH (1H), 8.38-8.43 (t) CH (1H), 8.89 (broad) (NH) (1H).

$^{13}$C NMR: δ value (ppm): 42.78 (1C), 63.97 (1C), 64.03 (1C), 81.35 (1C), 82.87 (1C), 101.86 (1C), 116.29 (1C), 116.89 (1C), 120.45 (1C), 120.73 (1C), 122.43 (1C), 123.02 (1C), 129.05 (1C), 131.83 (1C), 134.14 (1C), 139.11 (2C), 142.45 (1C), 143.16 (1C), 153.8 (1C), 156.30 (1C), 156.63 (1C).

MS: 383.2 [M], 382.2 [M−1]

Example—2

Preparation of 3-{4-[(Benzo[1,3]dioxol-5-yl methyl)-amino]-pyrazolo[3,4-d]pyrimidin-1-yl}-benzonitrile (Compound No. 42)

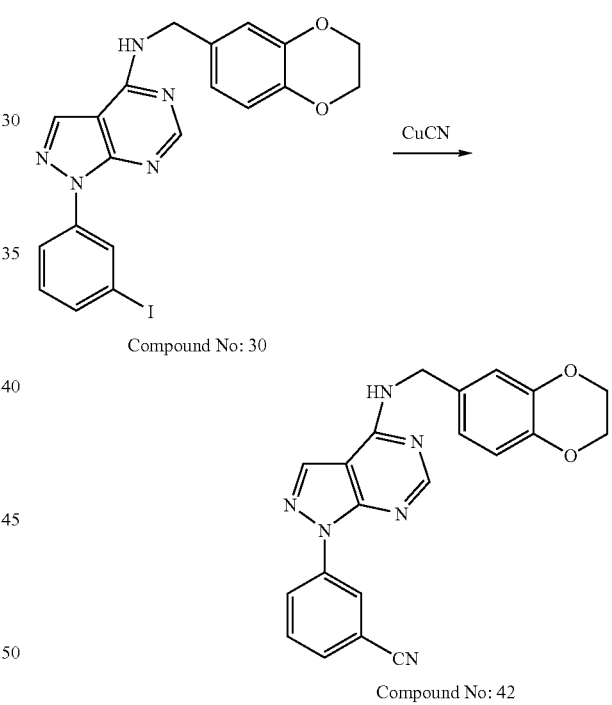

Compound No: 30

Compound No: 42

10 ml of dimethylformamide and 1.0 g (2.12 mmol) of benzo[1,3]dioxol-5-yl methyl-[1-(3-iodo-phenyl)-1H-pyrazolo[3,4-d]pyrimidine-4-yl]-amine (Compound No. 30) were charged into a 100 ml 4-necked round bottom flask, connected to a mechanical stirrer, thermometer socket, condenser, addition funnel and nitrogen gas bubbler. 0.57 g (6.40 mmol) of copper cyanide was charged. Reaction mass was heated to reflux temperature. Maintained the mass at reflux temperature for 4 hours. Reaction mass temperature was cooled to 25-30° C. 1.0 ml of aqueous ammonia was added. Stirred the mass for 15 min. 100.0 ml of Water was added. Stirred the mass for 15 min. The product was extracted with 50 ml of ethyl acetate and dried the organic layer over sodium sulphate. Ethyl acetate was distilled off completely under vacuum. Crude oil was crystallized on addition of 5 ml of isopropyl ether. Obtained 500.0 mg of the compound. (Yield—50% by theory).

Spectral Data:

FT-IR (K Br) (cm$^{-1}$): 3383, 3361, 3091, 2912, 2226, 1619, 1594, 1579, 1492, 1435, 1318, 1037, 985, 784, 672

MS: 372.3[M+2], 371.2 [M+1]

Example—3

Preparation of (2,3-Dihydro-benzo[1,4]dioxin-6-yl methyl)-1-(3-iodo-phenyl)-1H-pyrazolo[3,4-d]pyrimidin-4-yl)amine (Compound No. 25)

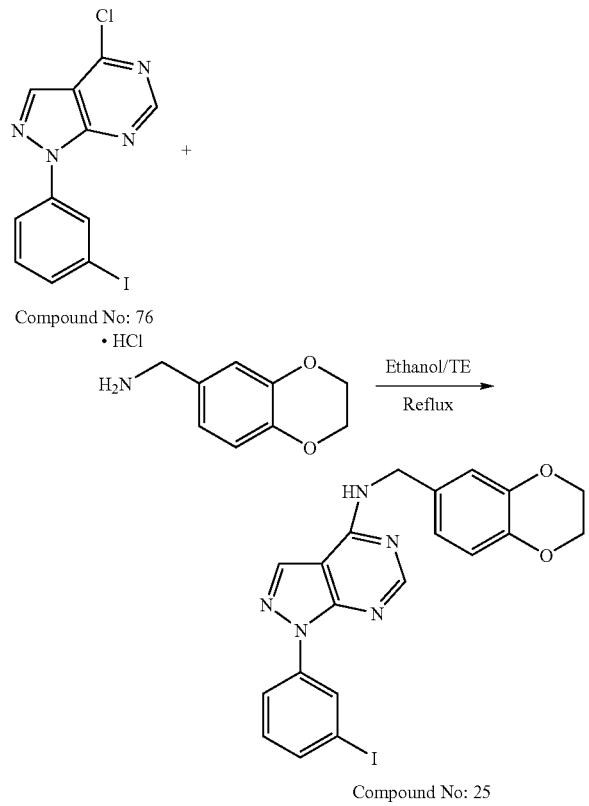

31.0 ml of ethanol and 3.0 g (8.41 mmol) of 4-chloro-1-(3-iodo-phenyl)-1H-pyrazolo[3,4-d]pyrimidine (Compound No. 76) were charged into a 100 ml of 4 necked round bottom flask connected to a mechanical stirrer, thermometer socket, condenser and addition funnel. 2.90 g (14.40 mmol) of 2,3-dihydro-benzo[1,4]dioxin-6-yl-methylamine hydrochloride was charged at 25-30° C. under stirring. Stirred the mass at 25-30° C. for 15-20 min. 30.0 g (0.20 mol) of triethyl amine was added slowly at maintaining the mass temperature 25-30° C. during 30-45 min. Maintained the mass temperature at 25-30° C. for 30-45 min. Reaction mass temperature was raised to reflux. Maintained the mass temperature at reflux for 5 hours. Reaction mass temperature was cooled to 25-30° C. Maintained the mass temperature at 25-30° C. for 60-90 min. Reaction mass temperature was cooled to 0-5° C. Maintained the mass temperature at 0-5° C. for 90-120 min. Solid was filtered and solid was washed with 10.0 ml of chilled ethanol. Compound was dried under vacuum at 60-65° C. 2.80 g of dry weight is obtained (yield—68.62% by theory).

Purity by HPLC—99.85%.

Melting point: 197.9° C.

Spectra Data:

FT-IR (K Br) (cm$^{-1}$): 3426, 3193, 3099, 2969, 2926, 1602, 1578, 1509, 1472, 1102, 1067, 938, 676, 633

400 MHz $^1$H NMR (DMSO-d$_6$) δ value (ppm): 4.20 (s) 2-CH2 (4H), 4.63-4.65 (d) CH2 (2H), 6.79-6.86 (m) Ar-Ha, Hb, Hc (3H), 7.31-7.35 (t) Ar-Hd (1H), 7.67-7.69 (d) Ar—He, Hf, Hg (3H), 8.24-8.26 (d) Ar-Hh (1H), 8.41-8.47 (d) Ar-Hi (1H), 8.85 (s) NH (1H) $^{13}$C NMR: δ value (ppm): 42.74 (1C), 63.98 (2C), 94.44 (1C), 101.81 (1C), 116.23 (1C) 116.81 (1C), 119.41 (1C), 120.39 (1C), 128.28 (1C) 130.99 (1C), 131.74 (1C), 134.19 (1C), 134.40 (1C), 139.93 (1C), 142.41 (1C), 143.11 (2C), 153.04 (1C), 156.24 (1C), 156.60 (1C).

MS: 486.4[M+1]

Example—4

Preparation of (2,3-Dihydro-Benzo[1,4]dioxin-6-yl methyl)-[1-(3,5-dimethyl-phenyl)-1H-pyrazolo[3,4-d]pyrimidin-4-yl]-amine (Compound No. 49)

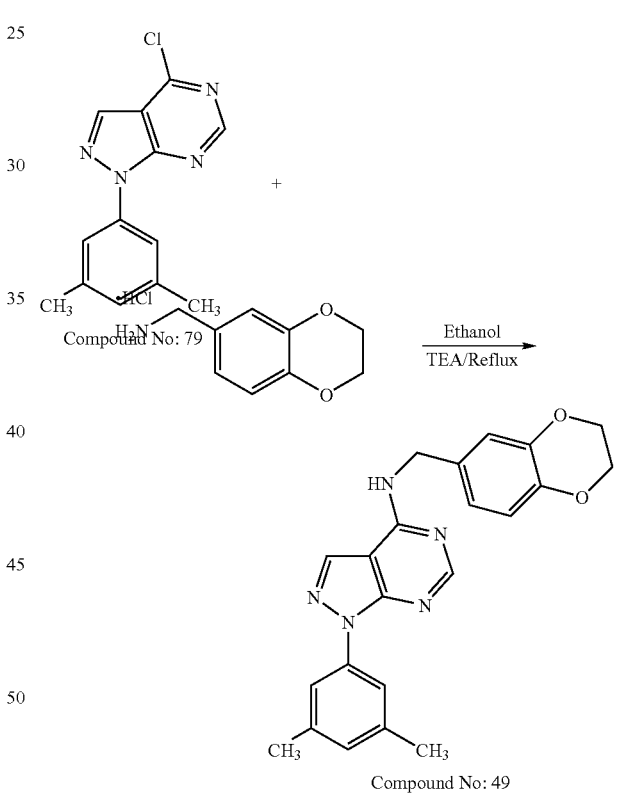

350.0 ml of ethanol and 25.0 g (0.096 mol) of 4-chloro-1-(3,5-dimethyl-phenyl)-1H-pyrazolo[3,4-d]pyrimidine (Compound No. 79) were charged into a 1.0 L 4 necked round bottom flask connected to a mechanical stirrer, thermometer socket, condenser and addition funnel. Stirred the mass at 25-30° C. for 15-20 min. 32.0 g of 2,3-dihydro-benzo[1,4] dioxin-6-yl-methylamine hydrochloride was charged at 25-30° C. under stirring. Stirred the mass at 25-30° C. for 15-20 min. 30.0 g of triethyl amine was added slowly at maintaining the mass temperature 25-30° C. during 30-45 min. Maintained the mass temperature at 25-30° C. for 30-45 min. Temperature of the reaction mass was raised to refluxing. Maintained the mass at reflux temperature for 10-11 hours. Reaction mass was cooled to 25-30° C. Maintained the mass temperature at 25-30° C. for 60-90 min. Reaction mass was cooled to 0-5° C. Maintained the mass temperature at 0-5° C. for 90-120 min. Solid was filtered and washed with 50.0 ml of chilled ethanol. Compound was dried under vacuum at 60-65° C. till constant weight is obtained. Dry weight of the compound is 35.50 g. 175.0 ml of dimethyl sulphoxide and 35.50 g of dry crude compound were charged into a 1.0 L 4-necked round bottom flask, connected to a mechanical stirrer, thermometer socket and condenser. Mass temperature was raised to 55-60° C. Maintained the mass temperature at 55-60° C. for 30-45 min. Insoluble solid was filtered through hyflow bed, washed the flask with 20.00 ml of hot dimethyl sulphoxide. Clear aerate was collected into flask. 1000.0 ml of Water is charged into a 3.0 L 4 necked round bottom flask, connected to a mechanical stirrer, thermo meter socket and addition funnel. Dimethyl sulphoxide solution was added slowly to water at maintaining the mass temperature at 25-35° C. over a period of 30-45 min. Maintained the mass temperature at 25-35° C. for 60-90 min. Temperature of the mass was cooled to 5-10° C. Maintained the mass temperature at 5-10° C. for 90-120 min. Solid was filtered and solid was washed with 150 ml of water. Compound was dried under vacuum at 60-65° C. 32.0 g Of dried compound is obtained (yield—85.5% by theory). Product purity by HPLC is 99.48%.

Melting range is 183.4° C.-183.6° C.

Spectra Data:

FT-IR (K Br) (cm$^{-1}$):

3423, 3236, 3158, 3097, 2991, 2919, 1593, 1546, 1506, 1485, 1457, 1437, 1426, 1371, 1344, 1326, 1306, 1280, 1262, 1252, 1234, 1217, 1205, 1150, 1122, 1097, 1065, 1048, 962, 933, 911, 885, 851, 829, 792, 765, 732, 703, 683, 653, 634, 581, 538, 467, 434.

400 MHz $_1$H NMR (DMSO-d$_6$) δ value (ppm): 2.34 s (2CH3), 4.19 s (2CH2), 4.64 d (CH2), Ar Ha, Hb, Hc m (3H), Ar Hd, He, Hf s (3H), Hg s (1H), Hh s (1H), NH t (1H)

$^{13}$C NMR: δ value (ppm): 21.05 (2C), 42.76 (1C), 64.04 (2C), 101.72 (1C), 116.3 (1C), 118.32 (1C), 120.45 (1C), 127.47 (1C), 131.97 (1C), 133.39 (1C), 138.22 (2C), 138.89 (1C), 142.45 (1C), 143.17 (1C), 152.78 (1C), 156.31 (1C), 156.42 (1C).

MS: 388.0[M+1]

Example—4a

Preparation of (2,3-Dihydro-Benzo[1,4]dioxin-6-yl methyl)-[1-(3,5-dimethyl-phenyl)-1H-pyrazolo[3,4-d]pyrimidin-4-yl]-amine hydrochloride (Compound No. 49-A)

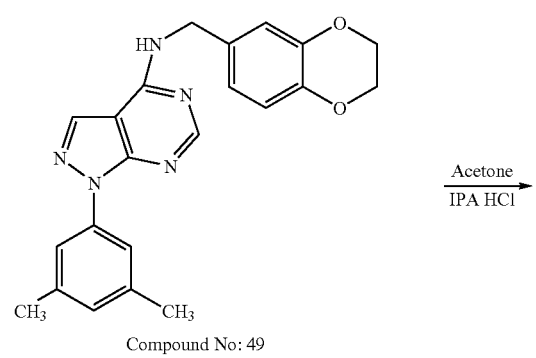

Compound No: 49

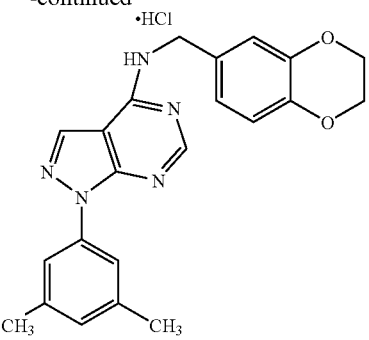

Compound No: 49-A 450 ml of acetone was charged into a 1.0 L 4-necked round bottom flask connected to a mechanical stirrer, thermometer socket, condenser and addition funnel. 30.0 g (0.078 mol) of 2,3-Dihydro-benzo[1,4]dioxin-6-yl methyl)-[1-(3,5-dimethyl-phenyl)-1H-pyrazolo[3,4-d]pyrimidin-4-yl]-amine (Compound No. 49) was charged. Stirred the mass at 25-30° C. for 15-20 min. 21.0 g of IPA HCl was charged at 25-30° C. under stirring. Maintained the mass temperature at 25-30° C. for 30-45 min. Solid was filtered and washed with 150.0 ml of acetone. Compound was dried under high vacuum at 65-70° C. 30.0 g Of dried compound was obtained (yield—91.46%)

Purity by HPLC—99.80%.

Melting point 244.1° C.-244.3° C.

Spectral Data:

FT-IR (K Br) (cm$^{-1}$): 3424, 3227, 3094, 3052, 2978, 2878, 2746, 1665, 1596, 1561, 1508, 1471, 1435, 1352, 1260, 1239, 1150, 985, 917, 885, 827, 778, 684, 646

400 MHz $^1$H NMR (DMSO-d$_6$) δ value (ppm: 2.49 s (2CH3), 4.20 s (2CH2), 4.65 d (CH2), 6.80-6.84Ar Ha, Hb, He m (3H), 6.85-6.89Ar Hd, He, Hf s (3H), 6.99Hg s (1H), 7.77Hh s (1H), 8.44 NH t (1H), 9.10 broad (HCl)

$^{13}$C NMR: δ value (ppm): 20.98 (2C), 44.25 (1C), 64.05 (2C), 101.46 (1C), 116.78 (1C), 117.01 (1C), 119.28 (2C), 120.89 (1C), 128.60 (1C), 129.72 (1C), 135.30 (1C), 137.84 (2C), 138.51 (1C), 142.90 (1C), 143.24 (1C), 150.74 (1C).

MS: 425.3 [M+2], 424.3 [M+1], 422.3 [M−1], 387.4 [M-HCl]

Example—5

Preparation of Benzo[1,3]dioxol-5-yl methyl-[1-(3,5-dimethyl-phenyl)-1H-pyrazolo[3,4-d]pyrimidine-4-yl)-amine (Compound No. 50)

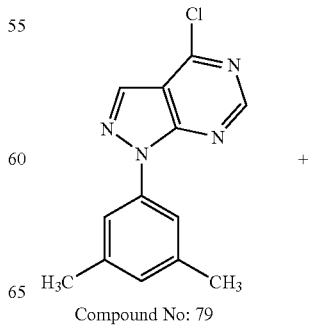

Compound No: 79

+

Acetone / IPA HCl

57
-continued

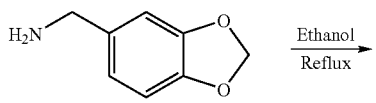

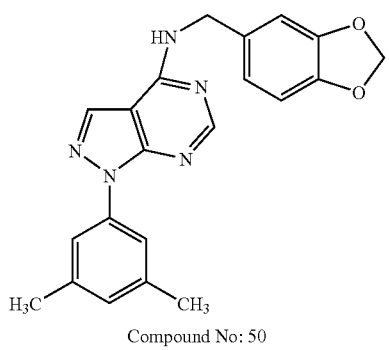
Compound No: 50

40.0 ml of ethanol and 2.0 g (7.74 mmol) of 4-chloro-1-(3, 5-dimethyl-phenyl)-1H-pyrazolo[3,4-d]pyrimidine (Compound No. 79) were charged into a 250 ml of 4-necked round bottom flask connected to a mechanical stirrer, thermometer socket, condenser and addition funnel. 2.33 g (15.40 mmol) of (3,5-methylenedioxy)benzyl amine was charged at 25-30° C. under stirring. Mass temperature was raised to reflux. Maintained the mass temperature at reflux for 6 hours. Mass temperature was cooled to 25-30° C. Maintained the mass temperature at 25-30° C. for 60 min. Reaction mass temperature was cooled to 0-5° C. Maintained the mass temperature at 0-5° C. for 60 min. Solid was filtered and washed with 10.0 ml of chilled ethanol. Compound was dried under vacuum at 60-65° C. Dry weight of the compound: 2.20 g (yield—76.38%).

Melting point: 150.2° C.

Purity by HPLC—99.79%.

Spectral Data:

FT-IR (K Br) (cm-$^1$): 3423, 3233, 3149, 3101, 3006, 2891, 1593, 1542, 501, 1485, 1437, 1364, 1340, 1316, 1278, 1238, 1128, 1096, 1072, 1041, 946, 929, 846, 829, 809, 791, 703, 687, 635, 434

400 MHz $^1$H NMR (DMSO-d$_6$) δ value (ppm): 2.35 s (2CH3), 4.64 d (CH2), 5.79 s (CH2) 6.86 sAr Ha, Hb (2H), 6.94-6.97 d He d (1H), 7.81sAr Hd, He, Hf s (3H), 8.38-8.39 (d) Hg, Hh (2H), NH t (1H)

$^{13}$C NMR: δ value (ppm): 21.02 (1C), 43.09 (1C), 64.04 (1C), 100.82 (1C), 101.72 (1C), 108.05 (1C), 108.12 (2C), 118.31 (1C), 120.74 (1C), 127.44 (2C), 132.78 (1C), 133.36 (1C), 138.19 (1C), 138.86 (1C), 146.24 (1C), 147.28 (1C), 152.77 (1C), 156.30 (1C), 156.37 (1C)

MS: 374.0 [M+1]

58
Example—6

Preparation of [1-(3,5-Dimethyl-phenyl)-1H-pyrazolo[3,4-d]pyrimidine-4-yl]-[2-(2-methoxy-ethoxy)-ethyl]-amine (Compound No. 51)

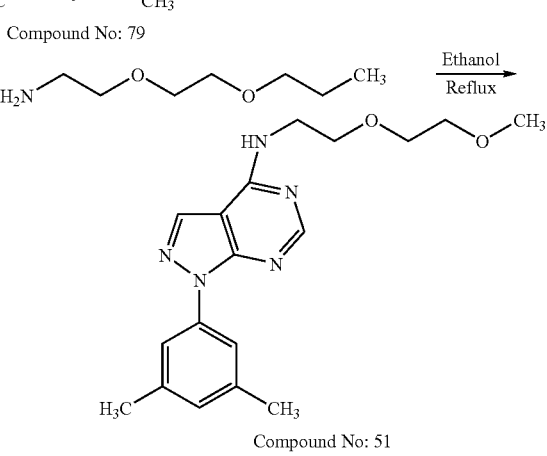
Compound No: 51

60.0 ml of ethanol and 10.0 g (0.038 mol) of 4-chloro-1-(3,5-dimethyl-phenyl)-1H-pyrazolo[3,4-d]pyrimidine (Compound No. 79) were charged into a 250 ml of 4 necked round bottom flask connected to a mechanical stirrer, thermometer socket, condenser and addition funnel. 22.40 g (0.18 mol) of 2-(2-Methoxy-ethoxy)-ethyl amine was charged at 25-30° C. under stirring. Reaction mass temperature was raised to reflux. Maintained the mass temperature at reflux for 5 hours. Reaction mass temperature was cooled to 25-30° C. Maintained the mass temperature at 25-30° C. for 60 min. Reaction mass temperature cooled to 0-5° C. Maintained the mass temperature at 0-5° C. for 60 min. Solid does not formed. Distilled off Ethanol completely under vacuum. Crude oily mass was obtained. Oily mass was dissolved in 45 ml of acetonitrile. 300.0 ml of isopropyl ether was added. Solid was formed. Solid was filtered and solid was washed with 50.0 ml of isopropyl ether. Compound was dried under vacuum at 60-65° C. Dry weight of the compound: 7.50 g (yield—56.80%). Melting point: 90.4° C.

Purity by HPLC is 99.76%.

Spectral Data:

FT-IR (K Br) (cm-$^1$): 3537, 3362, 3265, 3132, 3050, 3012, 2915, 2883, 2872, 1627, 1602, 1568, 1528, 1479, 1389, 1201, 1166, 1134, 980, 929, 886, 684

400 MHz NMR (DMSO-d$_6$) δ value (ppm): 2.35 s (2CH3), 3.22 s (O—CH3), 3.31 d (O—CH2-CH2), 3.43-3.56 t (NH—CH2), 3.61-3.69 t (O—CH2), 6.96 s (Ar-Ha, Hb), 7.80 s (Ar-Hc), 8.37 s (Hd), 8.38 t (NH), 8.54 d (He).

$^{13}$C NMR: δ value (ppm): 21.03 (2C), 40.01 (1C), 57.99 (1C) 68.79 (1C), 69.48 (1C), 71.21 (1C), 101.76 (1C), 118.29 (2C), 127.44 (1C), 133.40 (1C), 138.21 (2C), 138.87 (1C), 152.72 (1C), 156.33 (1C), 156.54 (1C).

MS: 342[M+1]

Example—7a

Preparation of 3,5-Dimethyl phenyl hydrazine hydrochloride

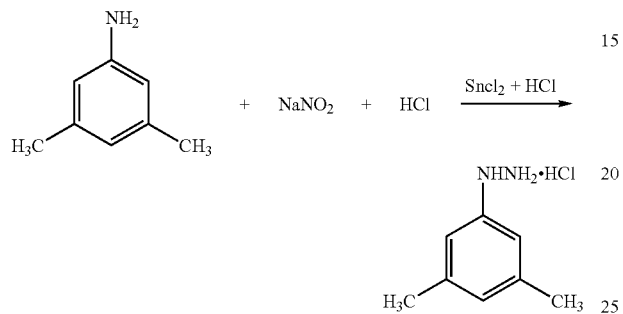

2220.0 ml hydrochloric acid was charged into a 5.0 L 4 necked round bottom flask connected to a mechanical stirrer, thermo meter socket, and condenser. 200.0 g (1.65 mol) of 3,5-Dimethyl aniline was charged at 25-35° C. Reaction mass was stirred for 20 min. Reaction mass was cooled to −5 to 0° C. Sodium nitrite solution [120.0 g (1.74 mol) of Sodium nitrite was dissolved in 1060.0 ml of DM Water and cooled to 0-5° C.) was added to dimethyl aniline mass at −5 to 0° C. for 60-90 min. Maintained the mass temperature at −5 to 0° C. for 60-75 min. 740.0 ml of hydrochloric acid was charged into a 10.0 L 4 necked round bottom flask connected to a mechanical stirrer, thermo meter socket, and condenser. 746.0 g of stannous chloride .2H$_2$O (3.30 mol) was charged. Stirred the mass for 30-45 min at 25-35° C. Reaction mass was cooled to −5 to 0° C. The diazotized solution was added slowly to stannous chloride solution at −5 to 0° C. for 150-180 min. Maintained the mass temperature at −5 to 0° C. for 30-45 min. Reaction mass temperature was raised to 25-35° C. Maintained the mass temperature at 25-35° C. for 90-120 min. Solid was filtered and solid was washed with 200.0 ml of water. Compound was dried under vacuum at 55-60° C. 1000.0 ml of ethanol and crude compound were charged into a 2.0 L 4 necked round bottom flask connected to a mechanical stirrer, thermo meter socket, and condenser. Raised the mass temperature to reflux temperature. Maintained the mass temperature at reflux for 30-45 min. 20.0 g of carbon was charged and maintained the mass temperature at reflux for 30-45 min. Carbon was filtered and carbon was washed with 200.0 ml of ethanol. Collected the filtrate into a flask. Distilled off ethanol completely under vacuum at mass temperature not crossing 60° C. Mass temperature was cooled to 25-35° C. and release the vacuum. 800.0 ml of isopropyl ether was charged. Maintained the mass temperature at 25-35° C. for 45-60 min and mass temperature was cooled to 0 to 5° C. Maintained the mass temperature at 0 to 5° C. for 45-60 min. Solid was filtered and solid was washed with 200.0 ml of isopropyl ether. Compound was dried under vacuum at 45-50° C. till obtaining constant weight. Dry weight of the compound weight: 243.0 g (yield 85.22%) Purity by HPLC: 99.6%, 3,5-Dimethyl content by HPLC is 0.13%

Spectral Data: FT-IR (K Br) (cm$^{-1}$): 3237, 3118, 3008, 2919, 2662, 1608, 1588, 1577, 1533, 1518, 1308, 1276, 1159, 1061, 684, cm-1.

400 MHz $^1$H NMR (DMSO-d$_6$): δ value (ppm): 2.20 s (2-CH3), 2.49 s (NH2), 6.58 s (Ar-Ha, Hb, Hc. 8.10 broad (NH), 10.09 broad (HCl).

$^{13}$C NMR δ value: 21.11 (2C), 112.33 (2C), 123.02 (1C), 137.98 (2C), 145.56 (1C).

Mass: 137.26 [M]+1, —HCl, 121.20 [M−NH2]

Example—7b

Preparation of 5-Amino-1-(3,5-dimethyl-phenyl)-1H-pyrazolo-4-carbonitrile

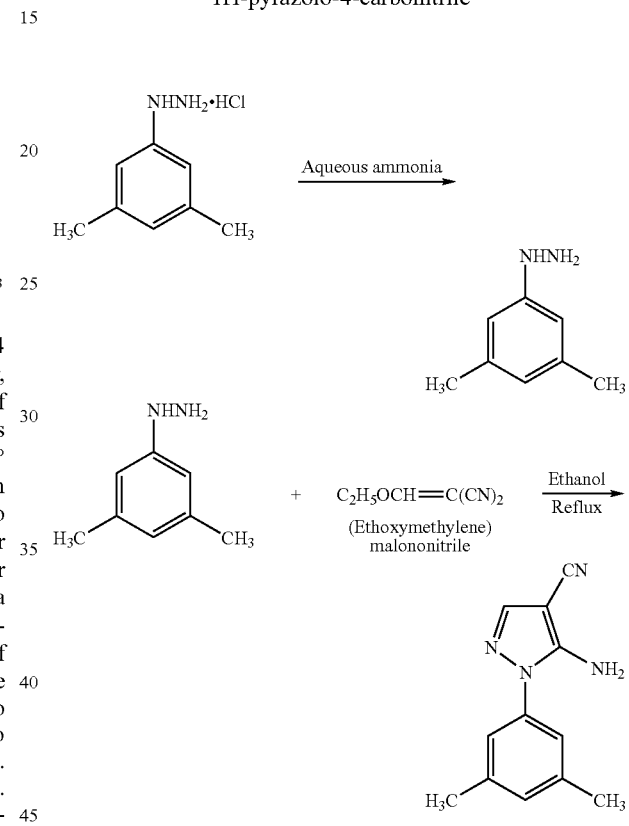

1000.0 ml of water was charged into a 5.0 L 4 necked round bottom flask connected to a mechanical stirrer, thermo meter socket, and condenser. 240.0 g (1.40 mol) 3,5-dimethyl phenyl hydrazine hydrochloride. Reaction mass pH was adjusted to 9.75±0.25 with aqueous ammonia at 25-30° C. Maintained the mass temperature at 25-30° C. for 30-45 min. Maintained the mass temperature at 25-30° C. for 45-60 min and compound was extracted with 3×500.0 ml of methylene chloride. Organic layer was dried with sodium sulphate upto obtaining moisture content is not more than 0.2% w/v. Sodium sulphate was filtered and sodium sulphate was washed with 250.0 ml of methylene chloride. Collected the filtrate into a flask, distilled off methylene chloride completely under vacuum at below 50° C. Finally applied high vacuum for removed the traces of methylene chloride completely at mass temperature not crossing 50° C. Cooled the mass temperature to 25-30° C. and released the vacuum. 150.0 ml of hexane was charged. Maintained the mass temperature at 25-30° C. for 45-60 min. Solid was filtered and solid was washed with 50:0 ml of hexane. Compound was dried under vacuum at 25-30° C. for 5-6 hours, weighed the dried compound. Dried weight of the compound: 121.0 g. 725 ml of ethanol (absolute) and 121.0 g (0.89 mol) of 3,5-Dimethyl phenylhydrazine into a 2.0 L 4 necked round bottom flask connect to a mechanical stirrer, thermo meter socket, and condenser under nitrogen atmosphere. 109.0 g (0.89 mol) of ethoxymethylenemalononitrile. Reaction mass temperature was raised to reflux. Maintained the mass temperature at reflux for 90-120 min. Reaction mass temperature was cooled to 10 to 15° C. Maintained the mass temperature at 10 to 15° C. for 90-120 min. Solid was filtered and solid was washed with 125 ml of isopropyl ether. Compound was dried under vacuum at 45-50° C. till constant weight obtained.

Dry weight of the compound: 161.5 g (yield: 54.83%).
Purity by HPLC is 99.91%.
Spectral Data:
FT-IR (K Br) (cm-$^1$): 3406, 3340, 3237, 3015, 2921, 2210, 1647, 1616, 1601, 1567, 1375, 650
400 MHz NMR (DMSO-$d_6$): δ value (ppm): 2.39 s (2CH3), 6.64 s (NH2), 7.04, 7.07 d (Ar-Ha, Hb, Hc), 7.74 s (Hd)
$^{13}$C NMR: δ value (ppm): 20.77 (2C), 73.26 (1C), 114.86 (1C), 121.65 (2C), 129.22 (1C), 137.25 (2C), 138.81 (1C), 141.39 (1C), 151.0 (1C)
MS: 213.26, 186.28

Example—7c

Preparation of 5-Amino-1-(3,5-dimethyl-phenyl)-1H-pyrazole-4-carboxylic acid amide (Compound No: 77)

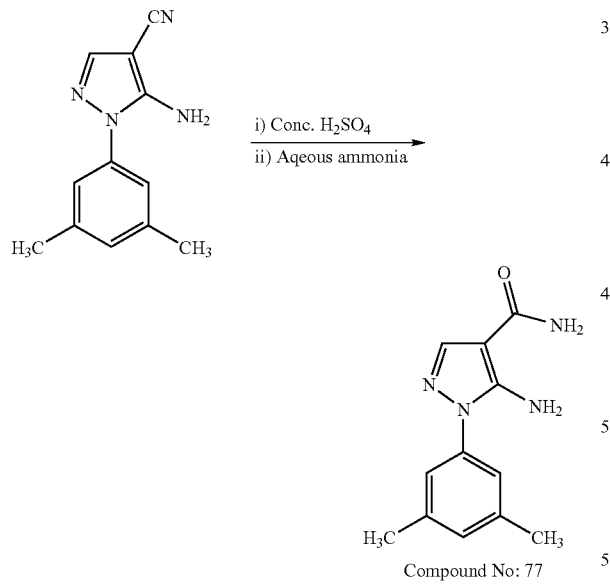

780.0 g of conc. sulphuric acid was charged into a 1.0 L 4 necked round bottom flask connected to a mechanical stirrer, thermo meter socket, and condenser under nitrogen atmosphere. Mass was cooled to 10-15° C. 92.0 g (0.44 mol) of 5-amino-1-(3,5-dimethyl-phenyl)-1H-pyrazolo-4-carbonitrile was added slowly lots wise at 10-15° C. for 120-150 min. Maintained the mass temperature at 10-15° C. for 30-45 min. Reaction mass temperature was raised to 25-30° C. and maintained the mass temperature at 25-30° C. for 90-120 min. 3.50 kg's of crushed ice was charged into a 10.0 L 4 necked round bottom flask connect to a mechanical stirrer, thermo meter socket, and condenser. Reaction mass solution was added slowly to crushed ice under stirring and mass temperature not crossing 10° C. Maintained the mass temperature at 5-10° C. for 60-90 min and adjusted the mass pH to 9.75±0.25 with aqueous ammonia at mass temperature not crossing 40° C. Maintained the mass temperature at 30-40° C. for 90-120 min. Solid was filtered and solid was washed with 100.0 ml of water. Compound was dried under vacuum at 55-60° C. Obtained dried weight of the compound: 95.0 g (yield 97.30%)

Purity by HPLC is 99.60%.
Spectral Data:
FT-IR (K Br) (cm-$^1$): 3425, 3339, 3257, 3190, 3112, 3010, 2918, 1654, 1605, 1555, 1465, 1333, 961, 889, 689, 632
400 MHz $_1$H NMR (DMSO-$d_6$): δ value (ppm): 2.32-2.49 s (2 CH3), 6.30 s ((NH2), 6.98 d [3H (Ar-Ha, Hb, He)], 7.14 broad (C=O—NH2), 7.85 d (1H)
$^{13}$C NMR: δ value (ppm): 20.87 (2C), 97.31 (1C), 120.71 (1C), 120.40 (2C), 138.09 (1C), 138.62 (2C), 138.75 (1C), 149.15 (1C), 166.21 (1C)
MS: 231.28 [M+1], 216.28 [M—NH2]

Example—7d

Preparation of 1-(3,5-Dimethyl-phenyl)-1,5-dihydro-pyrazolo[3,4-d]pyrimidine-4-one (Compound No: 78)

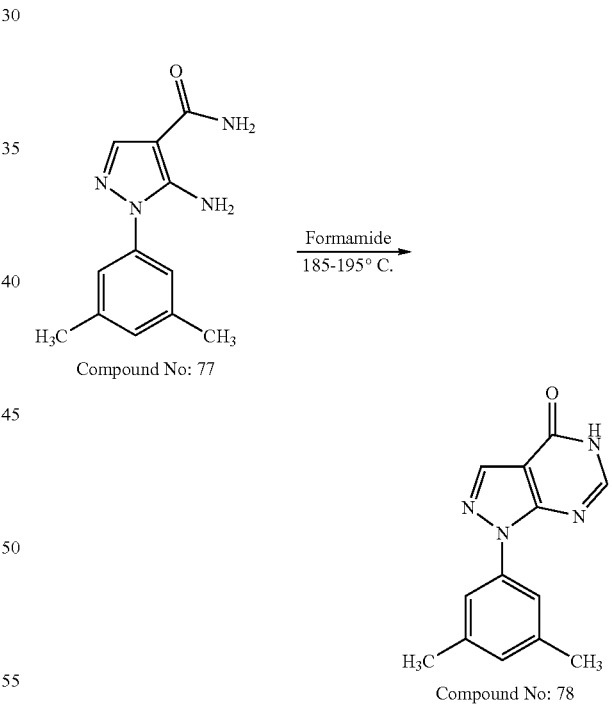

Charged 300.0 g of formamide into a 2.0 L 4 necked round bottom flask connected to a mechanical stirrer, thermo meter socket, and condenser under nitrogen atmosphere. 90.0 g (0.39 mol) of 5-Amino-1-(3,5-dimethyl-phenyl)-1H-pyrazole-4-carboxylic acid amide (Compound No. 77) was charged. Reaction mass temperature was raised to reflux (185-195° C.). Maintained the mass temperature at reflux for 60-90 min. Reaction mass temperature was cooled to 140-150° C. 900.0 ml of water was added slowly at maintaining the mass temperature 80-150° C. Maintained the mass temperature at 80-90° C. for 45-60 min. Reaction mass temperature was cooled to 25-30° C. Maintained the mass temperature at 25-30° C. for 90-120 min. Solid was filtered and solid was washed with 150.0 ml of water. 500.0 ml of DM Water and wet crude compound were charged into a 2.0 L 4 necked round bottom flask connected to a mechanical stirrer, thermo meter socket, and condenser. Mass temperature was raised to reflux. Maintained the mass temperature at reflux for 75-90 min and mass temperature was cooled to 25-30° C. Maintained the mass temperature at 25-30° C. for 90-120 min. Solid was filtered and solid was washed with 100.0 ml of water. Compound was dried under vacuum at 60-65° C. Dry weight of the compound: 65.0 g (yield 69.21%)

Purity by HPLC—99.47%.

Spectral Data:

FT-IR (K Br) (cm-$^1$): 3156, 3112, 3015, 2950, 2876, 1708, 1615, 1591, 1529, 1474, 1136, 1097, 839, 827, 780, 711, 679, 641, 627

400 MHz $_1$H NMR (DMSO-d$_6$) δ value (ppm): 2.34 s (CH3), 2.49 s (CH3), 7.03 s [Ar-Ha, Hb (2H)], 7.64 s [Ar—He (1H)] 8.19 s (1H), 8.29 s (1H), 12.20 broad (NH)

$^{13}$C NMR: δ value (ppm): 20.91 (2C), 107.46 (1C), 119.38 (2C), 128.40 (1C), 135.63 (2C), 138.32 (2C), 148.59 (1C), 151.69 (1C), 157.14 (1C)

MS: 241.26 [M+1]

Example—7e

Preparation of 4-chloro-1-(3,5-dimethyl-phenyl)-1H-pyrazolo[3,4-d]pyrimidine (Compound No: 79)

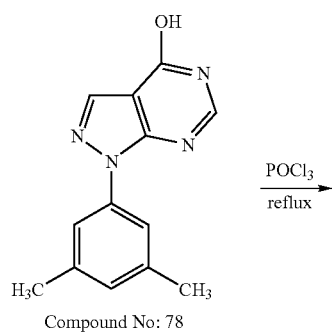

Compound No: 78

650.0 g of Phosphorus (V) oxychloride (POCl3) was charged into a 2.0 L 4 necked round bottom flask connected to a mechanical stirrer, thermo meter socket, and condenser under nitrogen atmosphere. 60.0 g (0.25 mol) of 1-(3,5-Dimethyl-phenyl)-1,5-dihydro-pyrazolo[3,4-d]pyrimidine-4-one (Compound No. 78) was charged. Reaction mass temperature was raised to reflux (105-108° C.). Maintained the mass temperature at reflux for 8-9 hour's. Reaction mass temperature was cooled to 25-30° C. and 600.0 ml of chloroform was charged. Maintained the mass temperature at 25-30° C. for 30-45 min. 2.0 kg's of crushed ice was charged into a 5.0 L 4 necked round bottom flask connect to a mechanical stirrer, thermo meter socket, and condenser. Reaction mass was added slowly at maintaining the mass temperature below 10° C. Maintained the mass temperature at 0-10° C. for 30-45 min. Mass temperature was raised to 25-30° C. 600.0 ml of Chloroform was charged. Maintained the mass temperature at 25-30° C. for 30-45 min and settled the mass for 20-30 min. Separated the bottom organic layer. Organic layer was dried with sodium sulphate upto obtaining the moisture content is not more than 0.20% w/v. 15.0 g of carbon was charged. Mass temperature was raised to 45-50° C. Maintained the mass temperature at 45-50° C. for 30-45 min. Carbon and sodium sulphate was filtered through hyflow bed and bed was washed with 300.0 ml of chloroform. Filtrate was collected into a flask. Chloroform was distilled completely under vacuum at mass temperature not crossing 60° C. Finally applied high vacuum to complete remove the traces of chloroform at mass temperature not crossing 60° C. Mass temperature was cooled to 25-30° C. and release the vacuum. 250.0 ml of isopropyl ether was charged. Maintained the mass temperature at 25-30° C. for 45-60 min. Solid was filtered and the solid was washed with 50.0 ml of isopropyl ether. Compound was dried under vacuum at 55-60° C. Dry weight of the compound: 56.0 g (yield 86.6%).

Product purity by HPLC—99.79%.

Spectral Data:

FT-IR (K Br) (cm-$^1$): 3096, 2952, 2913, 2854, 1614, 1605, 1589, 1546, 1481, 1426, 13791351, 1274, 1261, 1225, 848, 640,

400 MHz $_1$H NMR (DMSO-d$_6$): δ value (ppm): 2.36 s (CH3), 2.49 s (CH3), 7.05 s [Ar-Ha, Hb (2H)], 7.73 s [Ar-Hc (1H)], 8.69 s (1H), 8.95 s (1H)

$^{13}$C NMR: δ value (ppm): 20.97 (2C), 114.47 (1C), 118.62 (2C), 128.56 (1C), 133.52 (2C), 137.70 (1C), 138.56 (1C), 152.33 (1C), 154.0 (1C), 155.2 (1C)

MS: 259.26 [M+1], 223.28 [M−Cl]

Example—8

Preparation of 2,3-dihydro-benzo[1,4]dioxin-6-yl-methylamine hydrochloride

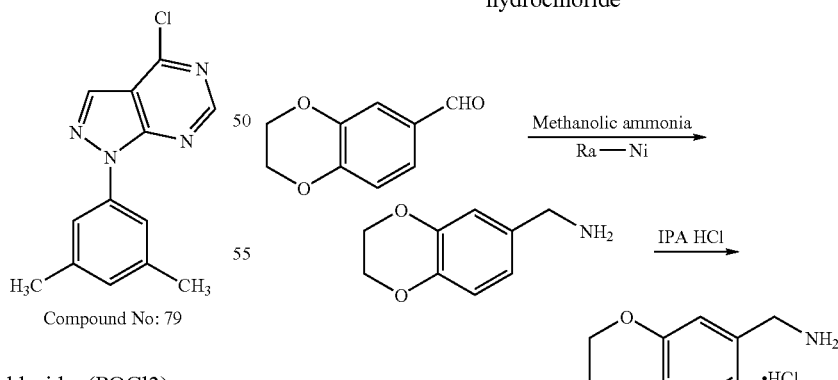

242.0 g of Methanolic ammonia [as 100% w/w by chemical assay] [Note: as chemical assay: 23.0% w/w, volume 1350.0 ml] and 30.0 g (0.183 mol) of 1,4-benzodioxan-6-carboxaldehyde were charged into a 2.0 L 4 necked round bottom flask, connect to a mechanical stirrer, thermo meter socket and condenser at 20-30° C. Stirred the mass for 20-30 min at 20-30° C. After dissolution is clear. Reaction mass was charged into a 2.0 L hydrogenator kettle at 20-30° C. 30.0 g of Raney Nickel (with Methanol dried) was charged under nitrogen atmosphere. Kettle was fitted to the hydrogenator. Nitrogen atmosphere was removed in Hydrogenator kettle with hydrogen gas by slowly flushing. Hydrogen gas was feeded upto 50-55 psi in hydrogenation kettle under oscillation. Maintained the hydrogen gas pressure (50-55 psi) till the hydrogen gas consumption is stopped. Reaction mass temperature was raised to 40-45° C. After hydrogen gas consumption is stooped at 45-50° C. Reaction mass temperature was cooled to 25-30° C. Maintained the hydrogen gas pressure at 50-55 psi for till the hydrogen gas consumption is stopped (about 90-120 min) Raney nickel was filtered through hyflow bed under nitrogen atmosphere. Raney Nickel was washed with 300.0 ml of methanol under nitrogen atmosphere. Filterate was collected into a flask. Methanol was distilled completely under vacuum at mass temperature not crossing 55° C. Mass temperature was cooled to 40-45° C. and release the vacuum. 50.0 ml of isopropyl alcohol was added. Reaction mass pH was adjusted to 0.5±0.25 with IPA HCl. Maintained the mass temperature at 25-30° C. for 60-90 min under stirring. Solid was filtered and solid was washed with 20.0 ml of isopropyl alcohol. Compound was dried under vacuum at 40±5° C. Dry compound weight: 31.0 g (yield: 84.1%).

Spectral Data:
FT-IR (K Br) (cm-$^1$): 3447.6, 2977.6, 2870.0, 1594.5, 1506.6, 1474.0, 1285.8, 1077.7, 1051. 735.2, 617.9, 472.0
MS: 202.6 [M+1]

Example—9

Preparation of benzene sulfonic acid 2-(2-methoxy-ethoxy)-ethyl ester (Compound No. 83)

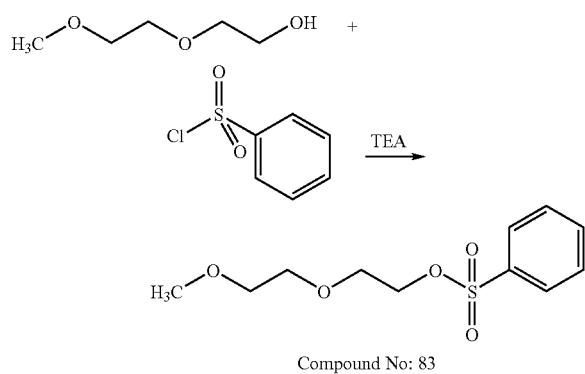

Compound No: 83

100 g (0.832 mol) of diethylene glycolmethylether and 600.0 ml of methylenechloride were charged into a 2.0 L 4 necked round bottom flask, connect to a mechanical stirrer, thermo meter socket, condenser and addition funnel. Reaction mass was cooled to −5 to 0° C. and then 210.0 g (2.07 mol) of triethylamine was charged. 147.0 g of benzenesulphonylchloride was added at maintaining the mass temperature at −5 to 0° C. Reaction mass temperature was raised to 25 to 30° C. and maintained for 2 hours. Reaction mass was diluted with 400.0 ml of methylenechloride and reaction mass was cooled to −5 to 0° C. 500.0 ml of water was added and reaction mass temperature was raised to 25 to 30° C. and maintained for 30 min. Organic layer was separated and organic layer was washed with 2×500.0 ml of 10% sodium bicarbonate solution. Organic layer was dried with sodium-sulphte and methylenechloride was completely distilled under vacuum. Obtained crude oil weight was 183.0 g (yield: 84.4%).

Spectral Data:
FT-IR (neat) (cm-$^1$): 3066.4, 2882.1, 2824.4, 1586.1, 1448.9, 1359.2, 1187.3, 923.7, 849.9, 793.0, 689.6
MS: 261.3 [M+1]

Example—10

Preparation of 2-(2-Methoxy-ethoxy)-ethyl amine (Compound No: 84)

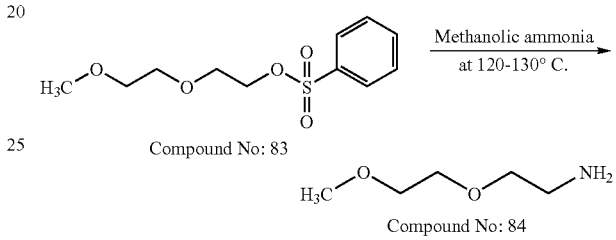

180.0 g (0.69 mol) of benzene sulfonic acid 2-(2-methoxy-ethoxy)-ethyl ester (Compound No. 79) and 600.0 ml of methanolic ammonia were charged into 1.0 L pressure sealed kettle. Reaction mass was heated to 120-130° C. under sealed conditions. Reaction mass temperature was maintained at 120-130° C. for 4 hours. Reaction mass temperature was cooled to 25-30° C. and methanol was completely distilled under vacuum. Remaining mass was diluted with 75.0 ml of water and mass pH was adjusted to 1 to 2 with 5.0 ml of conc. hydrochloric acid. Reaction mass was washed with 200.0 ml of methylene chloride. Again aqueous layer pH was adjusted to 9-10 with 130.0 ml of aqueous ammonia solution. Compound was extracted with 300.0 ml of methylene chloride and organic layer was dried with sodiumsuiphate. Methylenechloride was completely distilled and finally applied vacuum at below 50° C. Crude oil weight was 39.60 g (yield: 48.1%).

Spectral Data:
FT-IR (neat) (cm-$^1$): 3369.7, 2876.4, 1584.8, 1457.2, 1354.2, 1304.3, 1245.3, 1029.7, 849.3, 578.2
MS: 120.1 [M+1]

Example—11

Preparation of 4-methoxy-3-(3-morpholin-4-yl-propoxy benzyl amine (Compound No: 85)

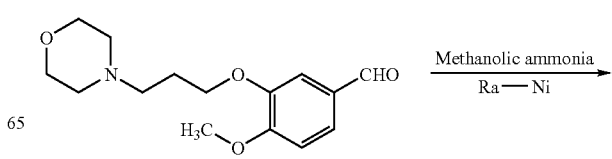

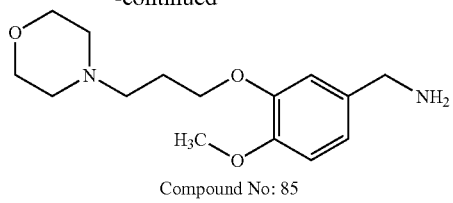

Compound No: 85

600.0 ml of methanolic ammonia [Note: as chemical assay: 25.0% w/w] and 33.0 g (0.118 mol) of 4-methoxy-3-(3-morpholin-4-yl-propoxy benzaldehyde were charged into a 2.0 L 4 necked round bottom flask, connect to a mechanical stirrer, thermo meter socket and condenser at 20-30° C. Stirred the mass for 20-30 min at 20-30° C. After dissolution is clear. Reaction mass was charged into a 2.0 L hydrogenator kettle at 20-30° C. 33.0 g of Raney Nickel (with Methanol dried) was charged under nitrogen atmosphere. Kettle was fitted to the hydrogenator. Nitrogen atmosphere was removed in Hydrogenator kettle with hydrogen gas by slowly flushing. Hydrogen gas was feeded upto 50-55 psi in hydrogenation kettle under oscillation. Maintained the hydrogen gas pressure (50-55 psi) till the hydrogen gas consumption is stopped. Reaction mass temperature was raised to 40-45° C. After hydrogen gas consumption is stooped at 45-50° C. Reaction mass temperature was cooled to 25-30° C. Maintained the hydrogen gas pressure at 50-55 psi for till the hydrogen gas consumption is stopped (about 90-120 min). Raney nickel was filtered through hyflow bed under nitrogen atmosphere. Raney Nickel was washed with 300.0 ml of methanol under nitrogen atmosphere. Filtrate was collected into a flask. Methanol was distilled completely under vacuum at mass temperature not crossing 55° C. Mass temperature was cooled to 30-35° C. and release the vacuum. Obtained oily mass weight 31.0 g (yield: 93.6% by theory).

Spectral Data:
FT-IR (neat) (cm-$^1$): 3356.1, 2954.9, 2857.2, 1606.7, 1591.2, 1515.0, 1444.1, 1426.4, 1260.5, 1235.7, 1137.9, 1116.7, 1068.5, 1028.5, 863.0, 808.7, 653.7, 589.5
MS: 281.2 [M+1]

Example—12

Preparation of 3,4-bis-(2-methoxy-ethoxy)-benzaldehyde

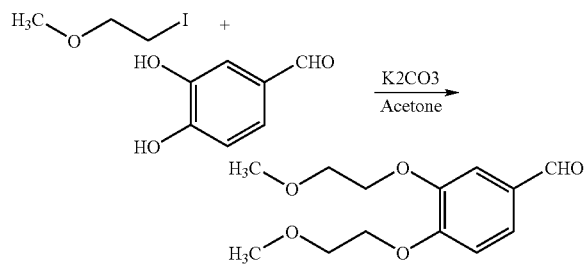

80.0 g (0.57 mol) of 3,4-dihydroxy benzaldehyde and 800.0 ml of acetone were charged into 2.0 L 4 necked round bottom flask, connect to a mechanical stirrer, thermo meter socket and condenser at 25-30° C. Reaction mass was stirred for 20 min. 324.0 g (1.74 mol) of 1-iodo-2-methoxy-ethane and 240.0 g (1.70 mol) of potassium carbonate were charged. Reaction mass was heated to reflux. Reaction mass temperature was maintained at reflux for 6 hours. Reaction mass temperature was cooled to 25-30° C. and inorganic solid was filtered. Acetone was completely distilled under vacuum at below 60° C. Remaining mass was diluted with 400.0 ml of DM water. Compound was extracted with 400.0 ml of ethyl acetate and organic layer was dried with sodiumsulphate. Ethyl acetate was completely distilled under vacuum and finally applied high vacuum at below 60° C. 69.20 g of crude product (Oil) was obtained (yield: 47.0% by theory).

Spectral Data:
FT-IR: 3448.5, 2932.7,
2889.4, 2825.0, 1685.8, 1586.2, 1508.8, 1437.7, 1276.1, 11988.9, 1125.6, 1050.2, 810.4, 743.4, 653.6, 588.1.
MS: 255.4 [M+1]

Example—13

Preparation of 3,4-bis-(2-methoxy-ethoxyl-benzyl amine (Compound No: 86)

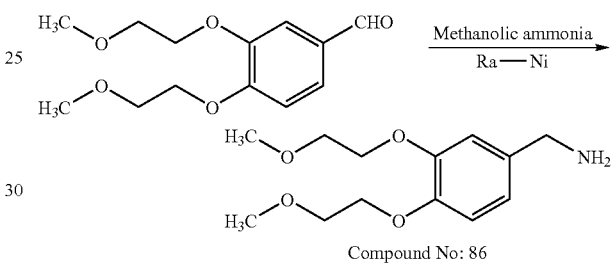

Compound No: 86

600.0 ml of methanolic ammonia [Note: as chemical assay: 25.0% w/w] and 60.0 g (0.236 mol) of 3,4-bis-(2-methoxy-ethoxy)-benzaldehyde were charged into a 2.0 L 4 necked round bottom flask, connect to a mechanical stirrer, thermo meter socket and condenser at 20-30° C. Stirred the mass for 20-30 min at 20-30° C. After dissolution is clear. Reaction mass was charged into a 2.0 L hydrogenator kettle at 20-30° C. 33.0 g of Raney Nickel (with Methanol dried) was charged under nitrogen atmosphere. Kettle was fitted to the hydrogenator. Nitrogen atmosphere was removed in Hydrogenator kettle with hydrogen gas by slowly flushing. Hydrogen gas was fed upto 50-55 psi in hydrogenation kettle under oscillation. Maintained the hydrogen gas pressure (50-55 psi) till the hydrogen gas consumption is stopped. Reaction mass temperature was raised to 40-45° C. After hydrogen gas consumption is stooped at 45-50° C. Reaction mass temperature was cooled to 25-30° C. Maintained the hydrogen gas pressure at 50-55 psi for till the hydrogen gas consumption is stopped (about 90-120 min). Raney nickel was filtered through hyflow bed under nitrogen atmosphere. Raney Nickel was washed with 300.0 ml of methanol under nitrogen atmosphere. Filtrate was collected into a flask. Methanol was distilled completely under vacuum at mass temperature not crossing 55° C. Mass temperature was cooled to 30-35° C. and release the vacuum. Obtained oily mass weight 52.0 g (yield: 86.3%).

Spectral Data:
Mass spectra: 256.3 [M+1]
The analogous compounds of 1-(3-ethynyl phenyl)-1H-pyrazolo[3,4-d]pyrimidine derivatives, compound numbers—1 to 12, have been prepared by following the procedure mentioned in example—1

| Compound Number | Molecular formula | Molecular weight | Mass peaks Peak-i | Mass peaks Peak-ii |
|---|---|---|---|---|
| 01 | $C_{22}H_{17}N_5O_2$ | 383.0 | 383.4 [M] | 382.4 [M − 1] |
| 02 | $C_{18}H_{19}N_5O_2$ | 337.0 | 337.3 [M] | 336.3 [M − 1] |
| 03 | $C_{28}H_{30}N_6O_3$ | 498.0 | 498.5 [M] | 497.5 [M − 1] |
| 04 | $C_{22}H_{19}N_5O_2$ | 385.0 | 385.4 [M] | 384.4 [M − 1] |
| 05 | $C_{26}H_{27}N_5O_4$ | 473.0 | 473.5 [M] | 472.5 [M − 1] |
| 06 | $C_{21}H_{15}N_5O_2$ | 369.0 | 368.3 [M] | 367.3 [M − 1] |
| 07 | $C_{15}H_{11}N_5O_2$ | 293.0 | 293.2 [M] | 292.2 [M − 1] |
| 08 | $C_{24}H_{23}N_5O_2$ | 413.0 | 413.4 [M] | 412.4 [M − 1] |
| 09 | $C_{23}H_{21}N_5O_3$ | 415.0 | 415.4 [M] | 414.4 [M − 1] |
| 10 | $C_{23}H_{21}N_5O_2$ | 399.0 | 399.4 [M] | 398.4 [M − 1] |
| 11 | $C_{21}H_{17}N_5O$ | 355.0 | 355.30 [M] | 354.30 [M − 1] |
| 12 | $C_{27}H_{28}N_6O_2$ | 468.0 | 468.5 [M] | 467.5 [M − 1] |

The analogous intermediate compounds of 1-(3-trimethyl silanylethynyl phenyl)-1H-pyrazolo[3,4-d]pyrimidine derivatives, compound numbers—13 to 24, have been prepared by following the procedure mentioned in example—1

| Compound Number | Molecular formula | Molecular weight | Mass peaks Peak-i | Mass peaks Peak-ii |
|---|---|---|---|---|
| 13 | $C_{25}H_{25}N_5O_2Si$ | 455.0 | 456.6 [M + 1] | 455.6 [M] |
| 14 | $C_{21}H_{27}N_5O_2Si$ | 409.0 | 410.5 [M + 1] | 409.5 [M] |
| 15 | $C_{31}H_{38}N_6O_3Si$ | 570.0 | 571.7 [M + 1] | 570.7 [M] |
| 16 | $C_{25}H_{27}N_5O_2Si$ | 457.0 | 458.3 [M + 1] | 457.3 [M] |
| 17 | $C_{29}H_{35}N_5O_4Si$ | 545.0 | 546.7 [M + 1] | 545.7 [M] |
| 18 | $C_{24}H_{23}N_5O_2Si$ | 441.0 | 442.5 [M + 1] | 441.5 [M] |
| 19 | $C_{18}H_{19}N_5O_2Si$ | 365.0 | 365.4 [M] | 364.4 [M − 1] |
| 20 | $C_{27}H_{31}N_5O_2Si$ | 485.0 | 486.6 [M + 1] | 485.6 [M] |
| 21 | $C_{26}H_{29}N_5O_3Si$ | 487.0 | 488.6 [M + 1] | 487.6 [M] |
| 22 | $C_{26}H_{29}N_5O_2Si$ | 471.0 | 472.6 [M + 1] | 471.6 [M] |
| 23 | $C_{24}H_{25}N_5OSi$ | 427.0 | 428.5 [M + 1] | 427.5 [M] |
| 24 | $C_{30}H_{36}N_6O_2Si$ | 540.0 | 541.7 [M + 1] | 540.7 [M] |

The analogous compounds of 3-iodophenyl-1H-pyrazolo[3,4-d]pyrimidine derivatives, compound numbers—25 to 36, have been prepared by following the procedure mentioned in example—2

| Compound Number | Molecular formula | Molecular weight | Mass peaks Peak-i | Mass peaks Peak-ii |
|---|---|---|---|---|
| 25 | $C_{20}H_{16}N_5O_2I$ | 485.0 | 486.3 [M + 1] | 485.3 [M] |
| 26 | $C_{16}H_{18}N_5O_2I$ | 439.0 | 440.2 [M + 1] | 439.2 [M] |
| 27 | $C_{26}H_{29}N_6O_3I$ | 600.0 | 601.4 [M + 1] | 600.4 [M] |
| 28 | $C_{20}H_{18}N_5O_2I$ | 487.0 | 488.3 [M + 1] | 487.3 [M] |
| 29 | $C_{24}H_{26}N_5O_4I$ | 575.0 | 576.4 [M + 1] | 575.4 [M] |
| 30 | $C_{19}H_{14}N_5O_2I$ | 471.0 | 472.2 [M + 1] | 471.2 [M] |
| 31 | $C_{13}H_{10}N_5O_2I$ | 395.0 | 395.1 [M] | 394.1 [M − 1] |
| 32 | $C_{22}H_{22}N_5O_2I$ | 515.0 | 516.3 [M + 1] | 515.3 [M] |
| 33 | $C_{21}H_{20}N_5O_3I$ | 517.0 | 518.3 [M + 1] | 517.3 [M] |
| 34 | $C_{21}H_{20}N_5O_2I$ | 501.0 | 502.3 [M + 1] | 501.3 [M] |
| 35 | $C_{19}H_{16}N_5OI$ | 457.0 | 458.2 [M + 1] | 457.2 [M] |
| 36 | $C_{25}H_{27}N_6O_2I$ | 570.0 | 571.4 [M + 1] | 570.4 [M] |

The analogous compounds of 3-cyanophenyl, -1H-pyrazolo[3,4-d]pyrimidine derivatives compound numbers—37 to 48, have been prepared by following the procedure mentioned in example—3

| Compound Number | Molecular formula | Molecular weight | Mass peaks Peak-i | Mass peaks Peak-ii |
|---|---|---|---|---|
| 37 | $C_{21}H_{16}N_6O_2$ | 384.0 | 385.40 [M + 1] | 384.40 [M] |
| 38 | $C_{17}H_{18}N_6O_2$ | 338.0 | 339.3 [M + 1] | 338.3 [M] |
| 39 | $C_{27}H_{29}N_7O_3$ | 499.0 | 500.5 [M + 1] | 499.5 [M] |
| 40 | $C_{21}H_{18}N_6O_2$ | 386.0 | 387.4 [M + 1] | 386.4 [M] |
| 41 | $C_{25}H_{26}N_6O_4$ | 474.0 | 475.5 [M + 1] | 474.5 [M] |
| 42 | $C_{20}H_{14}N_6O_2$ | 370.0 | 371.3 [M + 1] | 370.3 [M] |
| 43 | $C_{14}H_{10}N_6O_2$ | 294.0 | 294.2 [M] | 293.2 [M − 1] |
| 44 | $C_{23}H_{22}N_6O_2$ | 414.0 | 415.4 [M + 1] | 414.4 [M] |
| 45 | $C_{22}H_{20}N_6O_3$ | 416.0 | 417.4 [M + 1] | 416.4 [M] |
| 46 | $C_{22}H_{20}N_6O_2$ | 400.0 | 401.4 [M + 1] | 400.4 [M] |
| 47 | $C_{20}H_{16}N_6O$ | 356.0 | 357.3 [M + 1] | 356.3 [M] |
| 48 | $C_{26}H_{27}N_7O_2$ | 469.0 | 470.5 [M + 1] | 469.5 [M] |

The analogous compounds of 3,5-dimethyl pyrazolo[3,4-d]pyrimidine derivatives, compound numbers—49 to 60, have been prepared by similar way as mentioned in examples—4, 5 & 6

| Compound Number | Molecular formula | Molecular weight | Mass peaks Peak-i | Mass peaks Peak-ii |
|---|---|---|---|---|
| 49 | $C_{22}H_{21}N_5O_2$ | 387.0 | 388.4 [M + 1] | 387.4 [M] |
| 50 | $C_{21}H_{19}N_5O_2$ | 373.0 | 374.3 [M + 1] | 373.3 [M] |
| 51 | $C_{18}H_{23}N_5O_2$ | 341.0 | 342.3 [M + 1] | 341.3 [M] |
| 52 | $C_{28}H_{34}N_6O_3$ | 502.0 | 503.6 [M + 1] | 502.6 [M] |
| 53 | $C_{22}H_{23}N_5O_2$ | 389.0 | 390.4 [M + 1] | 389.4 [M] |
| 54 | $C_{26}H_{31}N_5O_4$ | 477.0 | 478.5 [M + 1] | 477.5 [M] |
| 55 | $C_{15}H_{15}N_5O_2$ | 297.0 | 297.3 [M] | 296.3 [M − 1] |
| 56 | $C_{24}H_{27}N_5O_2$ | 417.0 | 418.0 [M + 1] | 417.5 [M] |
| 57 | $C_{23}H_{25}N_5O_3$ | 419.0 | 420.4 [M + 1] | 419.4 [M] |
| 58 | $C_{23}H_{25}N_5O_2$ | 403.0 | 404.4 [M + 1] | 403.4 [M] |
| 59 | $C_{21}H_{21}N_5O$ | 359.0 | 360.4 [M + 1] | 359.4 [M] |
| 60 | $C_{27}H_{32}N_6O_2$ | 472.0 | 473.6 [M + 1] | 472.6 [M] |

The analogous compounds of m-tolyl-1H-pyrazolo[3,4-d]pyrimidine derivatives, compound numbers—61 to 71, have been prepared by similar way as mentioned in examples—4, 5 & 6

| Compound Number | Molecular formula | Molecular weight | Mass peaks Peak-i | Mass peaks Peak-ii |
|---|---|---|---|---|
| 61 | $C_{21}H_{19}N_5O_2$ | 373.0 | 374.4 [M + 1] | 373.4 [M] |
| 62 | $C_{17}H_{21}N_5O_2$ | 327.0 | 328.3 [M + 1] | 327.3 [M] |
| 63 | $C_{27}H_{32}N_6O_3$ | 488.0 | 489.5 [M + 1] | 488.5 [M] |
| 64 | $C_{21}H_{21}N_5O_2$ | 375.0 | 376.4 [M + 1] | 375.4 [M] |
| 65 | $C_{25}H_{29}N_5O_4$ | 463.0 | 464.2 [M + 1] | 463.2 [M] |
| 66 | $C_{14}H_{13}N_5O_2$ | 283.0 | 283.3 [M] | 282.3 [M − 1] |
| 67 | $C_{23}H_{25}N_5O_2$ | 403.0 | 404.4 [M + 1] | 403.4 [M] |
| 68 | $C_{22}H_{23}N_5O_3$ | 405.0 | 406.4 [M + 1] | 405.4 [M] |
| 69 | $C_{22}H_{23}N_5O_2$ | 389.0 | 390.2 [M + 1] | 389.2 [M] |
| 70 | $C_{20}H_{20}N_5O$ | 345.0 | 346.4 [M + 1] | 345.4 [M] |
| 71 | $C_{26}H_{30}N_6O_2$ | 458.0 | 459.5 [M + 1] | 458.5 [M] |

The intermediate compounds of 1-(3-iodophenyl)-pyrazolo[3,4-d]pyrimidine, compound numbers—72 to 76, have been prepared by similar way as mentioned in examples—7a-7e

| Compound Number | Molecular formula | Molecular weight | Mass peaks Peak-i | Mass peaks Peak-ii |
|---|---|---|---|---|
| 72 | $C_6H_8N_2ICl$ | 270.5 | 271.6 [M + 1] | 270.6 [M] |
| 73 | $C_{10}H_7N_4I$ | 310.0 | 311.1 [M + 1] | 310.1 [M] |
| 74 | $C_{10}H_9N_4OI$ | 328.0 | 329.1 [M + 1] | 328.1 [M] |
| 75 | $C_{11}H_7N_4OI$ | 338.0 | 339.2 [M + 1] | 338.2 [M] |
| 76 | $C_{11}H_6N_4ICl$ | 356.5 | 357.6 [M + 1] | 356.6 [M] |

The intermediate compounds of 3,5-dimethyl pyrazolo[3,4-d]pyrimidine, compound numbers—77 to 79, have been prepared by similar way as mentioned in examples—7a-7e

| Compound Number | Molecular formula | Molecular weight | Mass peaks Peak-i | Mass peaks Peak-ii |
|---|---|---|---|---|
| 77 | $C_{12}H_{14}N_4O$ | 230.0 | 231.2 [M + 1] | 230.2 [M] |
| 78 | $C_{13}H_{12}N_4O$ | 240.0 | 241.2 [M + 1] | 240.2 [M] |
| 79 | $C_{13}H_{11}N_4Cl$ | 258.5 | 259.7 [M + 1] | 258.7 [M] |

The intermediate compounds of (1-m-tolyl)-pyrazolo[3,4-d]pyrimidine, compound numbers—80 to 82, have been prepared by similar way as mentioned in examples—7a-7e

| Compound Number | Molecular formula | Molecular weight | Mass peaks Peak-i | Mass peaks Peak-ii |
|---|---|---|---|---|
| 80 | $C_{11}H_{12}N_4O$ | 216.0 | 217.2 [M + 1] | 216.2 [M] |
| 81 | $C_{12}H_{10}N_4O$ | 226.0 | 227.2 [M + 1] | 226.2 [M] |
| 82 | $C_{12}H_9N_4Cl$ | 244.5 | 245.7 [M + 1] | 244.7 [M] |

We claim:

1. A compound of formula-I,

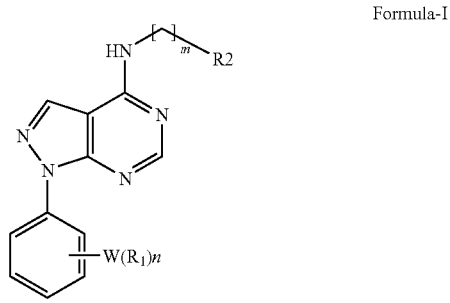

Formula-I or a pharmaceutically acceptable salt thereof,
where in m is 1, 2, or 3;
W is single bond;
$R_1$ is $C_2$-$C_6$ alkyl, when n=1; $C_1$-$C_6$ alkyl, when n=2 or 3; or $C_1$-$C_6$ alkenyl, alkynyl, NH, S, SO, SO2, O, C=O or an amide group, when n=1, 2 and 3;
or each $R_1$ is independently selected from halo, hydroxy, amino, hydroxyamino, carboxy, nitro, guanidino, ureido, carbamoyl, cyano, trifluoromethyl;
or each $R_1$ is independently selected from the group consisting of $C_2$-$C_6$ alkyl, when n=1; $C_1$-$C_6$ alkyl, when n=2 or 3; and $C_3$-$C_6$ cycloalkyl, $C_1$-$C_6$ alkoxy, $C_3$-$C_6$ cycloalkoxy; ($C_1$-$C_6$) alkoxycarbonyl, aryloxy, heteroaryloxy, $C_1$-$C_6$ thioalkoxy, $C_3$-$C_6$ thiocycloalkoxy, thioaryloxy, thioheteroaryloxy, nitro, amino, N-mono ($C_1$-$C_6$) alkylamino, N,N-di($C_1$-$C_6$) alkylamino, formamido, amido, acetamido, hydroxylamino, $C_1$-$C_6$ alkoxyamino, hydrazino, trifluoromethyl, trifluoromethoxy, $C_2$-$C_6$ alkenyl, $C_2$-$C_6$ alkynyl, aryl, heterocyclyl, fused aryl, fused heteroaryl and fused heterocyclyl, when n=1, 2 and 3;
or each $R_1$ is independently selected from $R_3$-sulfonylamino, phthalimido-($C_1$-$C_4$)-alkylsulfonylamino, benzamido, benzenesulfonylamino, 3-phenylureido, 2-oxopyrrolidin-1-yl, 2,5-dioxopyrrolidin-1-yl, and $C_2$-$C_4$ alkanoylamino and wherein said benzenesulfonylamino or phenyl or phenoxy or anilino or phenylsulfanyl substituent in $R^1$ may optionally bear one or two halogens, ($C_1$-$C_4$) alkyl, cyano, methansulfonyl or ($C_1$-$C_4$) alkoxy substituents; or any two $R_1$ taken together with the carbons to which they are attached comprise a 5-8 membered ring comprising at least one or two heteroatoms selected from oxygen, sulfur or nitrogen; and wherein the alkyl groups and alkyl portions of the alkoxy or alkylamino groups may be straight chained or if comprising at least three carbons may be branched or cyclic; where $R_3$ is selected from $C_1$-$C_6$-alkyl, $C_3$-$C_6$ cycloalkyl when n=1, 2 and 3;
$R_2$ is selected from the group consisting of hydrogen, $C_1$-$C_6$ alkyl, $C_3$-$C_6$ cycloalkyl, $C_1$-$C_6$ alkoxycarbonyl, aryl, heteroaryl, $C_1$-$C_6$ thioalkyl, trifluoromethyl, trifluoromethoxy, heterocyclyl, fused aryl, fused heteroaryl and fused heterocyclyl; or
$R_2$ is selected from the group consisting of phenyl or benzyl and substituted with 1, 2, 3 or 4 groups and the substituents are independently selected from R4,
where R4 is selected from hydrogen, halo, hydroxy, amino, hydroxyamino, carboxy, nitro, guanidino, ureido, carbamoyl, cyano, trifluoromethyl, $C^1$-$C^6$-alkyl, $C_3$-$C_6$ cycloalkyl, hydroxy, $C_1$-$C_6$ alkoxy, $C_3$-$C_6$ cycloalkoxy, $C_1$-$C_6$ alkoxycarbonyl, aryloxy, heteroaryloxy, $C_1$-$C_6$ thioalkoxy, $C_3$-$C_6$ thiocycloalkoxy, thioaryloxy, thioheteroaryloxy, nitro, amino, N-mono ($C_1$-$C_6$) alkylamino, N,N-di($C_1$-$C_6$) alkylamino, formamido, amido, acetamido, hydroxylamino, $C_1$-$C_6$ alkoxyamino, hydrazino, trifluoromethyl, trifluoromethoxy, alkenyl, alkynyl, aryl, heterocyclyl, fused aryl, fused heteroaryl and fused heterocyclyl.

2. The compound of claim 1, wherein the compound is:
N-((2,3-dihydrobenzo[b][1,4]dioxin-6-yl)methyl)-[1-(3-ethynyl-phenyl)-1H-pyrazolo[3,4-d]pyrimidin-4-yl-amine,
[2-(2 methoxy-ethoxy)-ethyl]-[1-(3-ethynyl-phenyl)-1H-pyrazolo[3,4-d]pyrimidin-4-yl)-amine,
[2-(2 methoxy-ethoxy)-ethyl]-[1-(3-ethynyl-phenyl)-1H-pyrazolo[3,4-d]pyrimidin-4-yl)-amine,
(3,4-Dimethoxy-benzyl)-[1-(3-ethynyl-phenyl)1H-pyrazolo[3,4-d]pyrimidine-4yl)-amine,
[3,4-Bis-(2-methoxy-ethoxy)-benzyl[1-(3-ethynyl-phenyl)-1H-pyrazolo[3,4-d]pyrimidine-4-yl)-amine,
Benzo[1,3]dioxol-5-yl methyl-[1-(3-ethynyl-phenyl)-1-H-pyrazolo[3,4-d]pyrimidine-4-yl]-amine,
[1-(3-ethynyl-phenyl)-1H-pyrazolo[3,4-d]pyrimidine-4ylamino)-acetic acid
3,4-Diethoxy-benzyl-[1-(3-ethynyl-phenyl)-1H-pyrazolo [3,4-d]pyrimidine-4yl)-amine,
[1-(3 ethynyl-phenyl)-1H-pyrazolo[3,4-d]pyrimidine-4yl)-(3,4,5-trimethoxy-benzyl)-amine,

[4-(2 methoxy-ethoxy)-benzyl)-[1-(3-ethynyl-phenyl)-1H-pyrazolo[3,4-d]pyrimidine-4yl)-amine,
(4-methoxy-benzyl-[1-(3-ethynyl-phenyl) 1H-pyrazolo[3,4-d]pyrimidine-4yl)-amine,
[4 (3-morpholin-4-yl-propoxy)-benzyl]-[1-(3-ethynyl-phenyl)-1H-pyrazolo[3,4-d]pyrimidine-4yl)-amine;
N-((2,3-dihydrobenzo[b][1,4]dioxin-6-yl)methyl)-[1-(3-trimethylsilanyl ethynyl-phenyl)-1H-pyrazolo[3,4-d]pyrimidin-4yl-amine,
[2-(2 methoxy-ethoxy)-ethyl]-[1-(3-trimethylsilanyl ethynyl-phenyl)-1H-pyrazolo[3,4-d]pyrimidin-4yl)-amine,
[4-Methoxy-3-(3-morpholine-4-yl-propoxy)-benzyl)-[1-(3-trimethylsilanyl ethynyl-phenyl)1H-pyrazolo[3,4-d]pyrimidine-4yl)-amine,
(3,4-Dimethoxy-benzyl)-[1-(3-trimethylsilanyl ethynyl-phenyl)-1H-pyrazolo[3,4-d]pyrimidine-4yl)-amine,
[3,4-Bis-(2-methoxy-ethoxy)-benzyl[1-(3-trimethylsilanyl ethynyl-phenyl)-1H-pyrazolo[3,4-d]pyrimidine-4yl)-amine,
Benzo[1,3]dioxol-5-yl methyl-[1-(3-trimethylsilany ethynyl-phenyl)-1-H-pyrazolo[3,4-d]pyrimidine-4-yl]-amine,
[1-(3 trimethylsilanyl ethynyl-phenyl)-1H-pyrazolo[3,4-d]pyrimidine-4ylamino)-acetic acid,
3,4-Diethoxy-benzyl-[1-(3-trimethylsilanyl ethynyl-phenyl)-1H-pyrazolo[3,4-d]pyrimidine-4yl)-amine,
[1-(3 trimethylsilanyl ethynyl-phenyl)-1H-pyrazolo[3,4-d]pyrimidine-4yl)-(3,4,5-trimethoxy-benzyl)-amine,
[4-(2 methoxy-ethoxy)-benzyl)-[1-(3-trimethylsilanyl ethynyl-phenyl)-1H-pyrazolo[3,4-d]pyrimidine-4yl)-amine,
(4-methoxy-benzyl-[1-(3-trimethylsilanyl ethynyl-phenyl)-1H-pyrazolo[3,4-d]pyrimidine-4yl)-amine, or
[4-(3 morpholin-4-yl-propoxy)-benzyl]-[1-(3-trimethylsilanyl ethynyl-phenyl)-1H-pyrazolo[3,4-d]pyrimidine-4yl)-amine;
N-((2,3-dihydrobenzo[b][1,4]dioxin-6-yl)methyl)-[1-(3-iodo-phenyl)-1H-pyrazolo[3,4-d]pyrimidin-4yl-amine,
[2-(2 methoxy-ethoxy)-ethyl]-[1-(3-iodo-phenyl)-1H-pyrazolo[3,4-d]pyrimidin-4yl)-amine,
[4-Methoxy-3-(3-morpholine-4-yl-propoxy)-benzyl)-[1-(3-iodo-phenyl)-1H-pyrazolo[3,4-d]pyrimidine-4yl)-amine,
(3,4-Dimethoxy-benzyl)-[1-(3-iodo-phenyl) 1H-pyrazolo[3,4-d]pyrimidine-4yl)-amine,
[3,4-Bis-(2-methoxy-ethoxy)-benzyl]-[1-(3-iodo-phenyl)-1H-pyrazolo[3,4-d]pyrimidine-4yl)-amine,
Benzo[1,3]dioxol-5-yl methyl-[1-(3-iodo-phenyl)-1-H-pyrazolo[3,4-d]pyrimidine-4-yl]-amine,
[1-(3-iodo-phenyl)-1H-pyrazolo[3,4-d]pyrimidine-4ylamino)-acetic acid,
3,4-Diethoxy-benzyl)-)-[1-(3-iodo-phenyl)-1H-pyrazolo[3,4-d]pyrimidine-4yl)-amine,
[1-(3 iodo-phenyl)-1H-pyrazolo[3,4-d]pyrimidine-4yl)-(3,4,5-trimethoxy-benzyl)-amine,
[4-(2 methoxy-ethoxy)-benzyl)-[1-(3-iodo-phenyl)-1H-pyrazolo[3,4-d]pyrimidine-4yl)-amine,
(4-methoxy-benzyl-[1-(3-iodo-phenyl) 1H-pyrazolo[3,4-d]pyrimidine-4yl)-amine, or
[4-(3-morpholin-4-yl-propoxy)-benzyl]-[1-(3-iodo-phenyl)-1H-pyrazolo[3,4-d]pyrimidine-4yl)-amine.

3. The compound of claim 1, wherein the compound is:
a) 3-{4-[(2,3-Dihydro-benzo[1,4]dioxin-6-ylmethyl)-amino]-pyrazolo[3,4-d]pyrimidin-1-yl}-benzonitrile,
b) 3-{4-[2-(2-methoxy-ethoxy)-ethylamino-pyrazolo[3,4-d]-1-yl}-benzonitrile,
c) 3-{4-[4-methoxy-3-(3-morpholin-4-yl-propoxy)-benzyl amino]-pyrazolo[3,4-d]pyrimidin-1yl-}-benzonitrile,
d) 3-[4-(3,4-dimethoxy-benzyl amino]-pyrazolo[3,4-d]pyrimidin-1yl-}-benzonitrile,
e) 3-{4-[3,4-bis-(2-methoxy-ethoxy)-benzyl amino]-pyrazolo[3,4-d]pyrimidin-1yl-}-benzonitrile,
f) 3-{4-[(Benzo[1,3]dioxol-5-yl methyl)-amino-pyrazolo[3,4-d]pyrimidin-1yl-}-benzonitrile,
g) [1-(3-cyano-phenyl)-1H-pyrazolo[3,4-d]pyrimidin-4-ylamino]-acetic acid,
h) 3-[4-(3,4-Diethoxy-benzyl amino)-pyrazolo[3,4-d]pyrimidin-1-yl]-benzonitrile,
i) 3-[4-(3,4,5-trimethoxy-benzylamino)-pyrazolo[3,4-d]pyrimidin-1-yl]-benzonitrile,
j) 3-{4-[4-(2-mehoxy-ethoxy)-benzyl amino]-pyrazolo[3,4-d]pyrimidin-1-yl}-benzonitrile,
k) 3-[4-(4-methoxy-benzylamino)-pyrazolo[3,4-d]pyrimidin-1yl]-benzonitrile, or
l) 3-{4-[4-(3-morpholin-4-yl-propoxy)benzyl amino]-pyrazolo[3,4-d]pyrimidin-1-yl}-benzonitrle.

4. The compound of claim 1, wherein the compound is:
N-((2,3-dihydrobenzo[b][1,4]dioxin-6-yl)methyl)-1-(3,5-dimethylphenyl)-1H-pyrazolo[3,4-d]pyrimidin-4-amine,
N-(benzo[d][1,3]dioxol-5-ylmethyl)-1-(3,5-dimethylphenyl)-1H-pyrazolo[3,4-d]pyrimidin-4-amine,
1-(3,5-dimethylphenyl)-N-(2-(2-methoxyethoxy)ethyl)-1H-pyrazolo[3,4-d]pyrimidin-4-amine,
[1(3,5-dimethyl-phenyl)-1H-pyrazolo[3,4-d]pyrimidine-4-yl]-[4-methoxy-3-(3-morpholin-4-yl-propoxy)-benzyl]-amine,
(3,4-dimethoxy-benzyl)-[1-(3,5-dimethyl-phenyl)-1H-pyrazolo[3,4-d]pyrimidine-4-yl]-amine,
[3,4-bis-(2-methoxy-ethoxy)-benzyl]-[1-(3,5-dimethyl-phenyl)-1H-pyazolo[3,4-d]pyrimidin-4-yl]-amine,
[1(3,5-dimethyl-phenyl)-1H-pyrazolo[3,4-d]pyrimidine-4-ylamino]acetic acid,
3,4-diethoxy-benzyl)-[1-(3,5-dimethyl-phenyl)-1H-pyrazolo[3,4-d]pyrimidine-4-yl]-amine,
[1(3,5-dimethyl-phenyl)-1H-pyrazolo[3,4-d]pyrimidine-4-yl]-(3,4,5-trimethoxy-benzyl)-amine,
[1(3,5-dimethyl-phenyl)-1H-pyrazolo[3,4-d]pyrimidine-4-yl]-[4-(2-methoxy-ethoxy)benzyl amine,
[1(3,5-dimethyl-phenyl)-1H-pyrazolo[3,4-d]pyrimidine-4-yl]-[4-(methoxy)benzyl amine, or
[1(3,5-dimethyl-phenyl)-1H-pyrazolo[3,4-d]pyrimidine-4-yl]-[4-(3-morpholine-4-yl-propoxy)benzyl amine.

5. The compound of claim 1, wherein the compound is:
a) N-((2,3-dihydrobenzo[b][1,4]dioxin-6-yl)methyl)-1-m-tolyl-1H-pyrazolo[3,4-d]pyrimidin-4-amine,
b) [2-(2-methoxy-ethoxy)-ethyl]-(1-m-tolyl-1H-pyrazolo[3,4-d]pyrimidine-4yl)-amine,
c) [4-Methoxy-3-(3-morpholine-4-yl-propoxy)-benzyl]-(1-m-tolyl-1H-pyrazolo[3,4-d]pyrimidine-4yl)-amine,
d) (3,4-Dimethoxy-benzyl)-(1-m-tolyl-1H-pyrazolo[3,4-d]pyrimidine-4yl)-amine,
e) [3,4-Bis-(2-methoxy-ethoxy)-benzyl]-(1-m-tolyl-1H-pyrazolo[3,4-d]pyrimidine-4yl)-amine,
f) (1-m-tolyl-1H-pyrazolo[3,4-d]pyrimidine-4ylamino)-acetic acid,
g) 3,4-Diethoxy-benzyl)-(1-m-tolyl-1H-pyrazolo[3,4-d]pyrimidine-4yl)-amine,
h) (1-m-tolyl-1H-pyrazolo[3,4-d]pyrimidine-4yl)-(3,4,5-trimethoxy-benzyl)-amine,
i) [4-(2-methoxy-ethoxy)-benzyl]-(1-m-tolyl-1H-pyrazolo[3,4-d]pyrimidine-4yl)-amine,
j) (4-methoxy-benzyl)-(1-m-tolyl-1H-pyrazolo[3,4-d]pyrimidine-4yl)-amine, or
k) [4-(3-morpholin-4-yl-propoxy)-benzyl]-(1-m-tolyl-1H-pyrazolo[3,4-d]pyrimidine-4yl)-amine.

6. A process for the preparation of a compound of Formula-I with an ethynyl substitution on the N-phenyl ring or a pharmaceutically acceptable salt thereof,

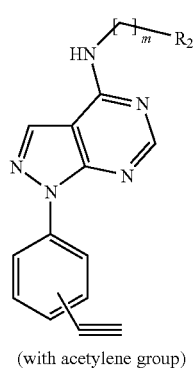

(with acetylene group)

the process comprising:

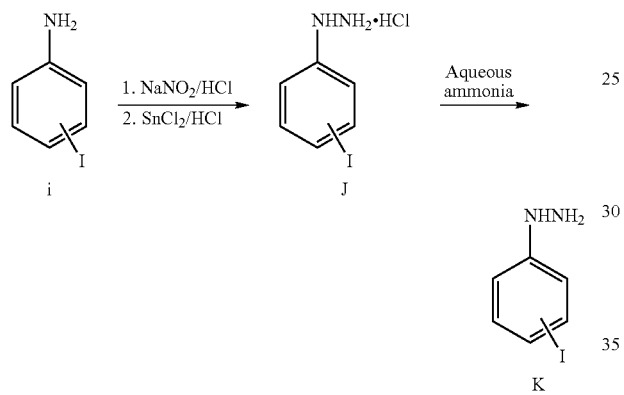

diazotising a compound of formula i with mineral acid and sodium nitrite at −10° C. to 5° C. to obtain iodo substituted phenyl hydrazine hydrochloride solid of formula-J;

neutralizing the compound of formula-J with a base to get an iodo substituted phenyl hydrazine of formula-K;

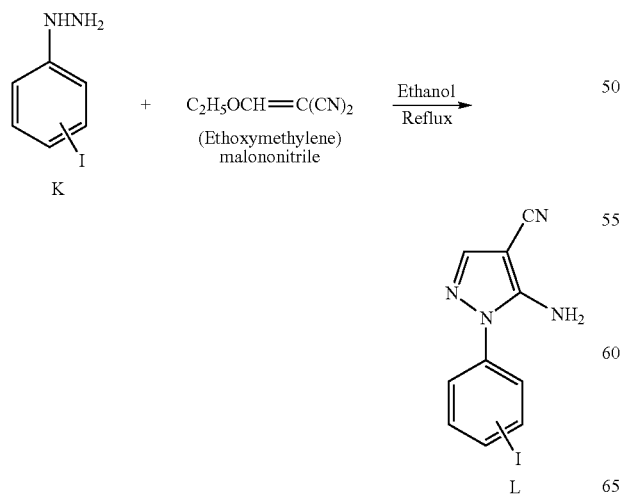

reacting the compound of formula K with ethoxymethelenemalononitrile in a protic solvent to obtain an N-(iodo substituted) phenyl-5-amino-1H-pyrazole-4-carbonitrile of formula-L;

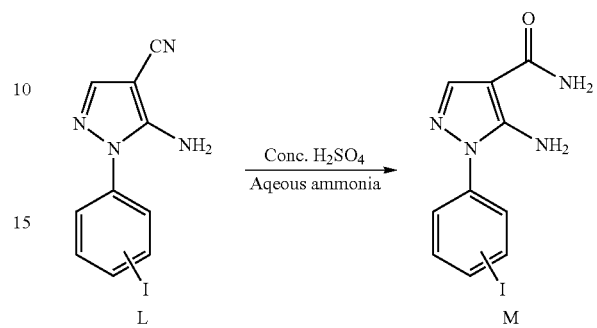

hydrolyzing the nitrile group of the compound of formula L with a mineral acid in aqueous medium; followed by basification with a base at 10° C. to 40° C. to obtain an N-(iodo substituted) phenyl-5-amino-1H-pyrazole-4-carboxamides of formula-M;

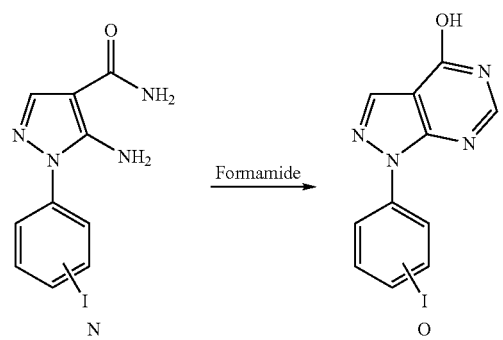

reacting the compound of formula-N with formamide to obtain an N-(iodo substituted) phenyl-5-amino-1H-pyrazole-4-carboxamide of formula-O;

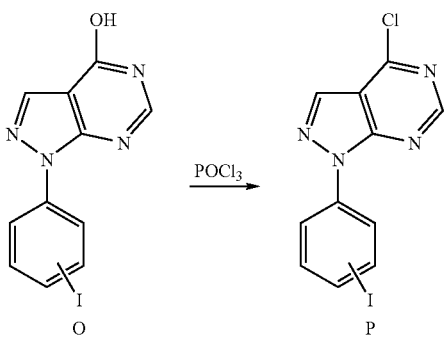

reacting the compound of formula O with phosphorus oxychloride, thionyl chloride, phosphorous trichloride or phosphorous pentachloride to obtain an N-(iodo substituted) 4-chloro-pyrazolo[3,4-d]pyrimidine of formula-P;

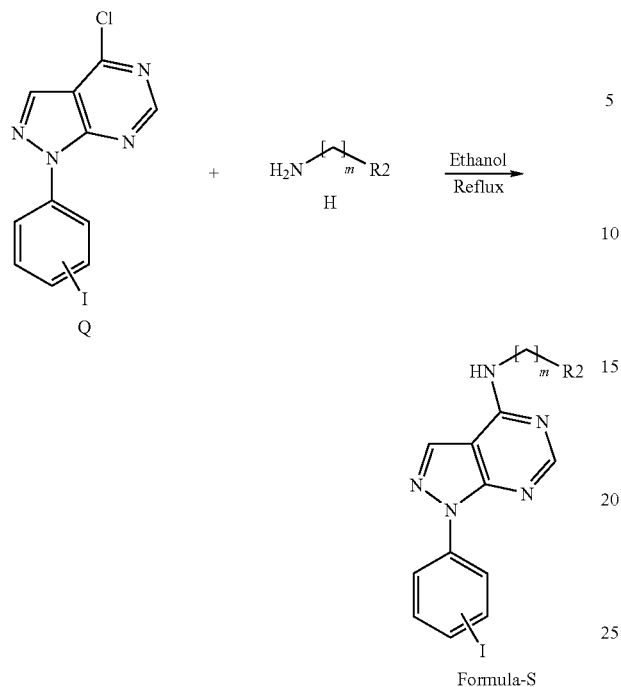

Formula-S refluxing the compound of formula Q with substituted alkyl amine of formula-H in protic solvent to obtain an 1-(iodo substituted) substituted 4-amino substituted-pyrazolo[3,4-d]pyrimidine of formula-S;

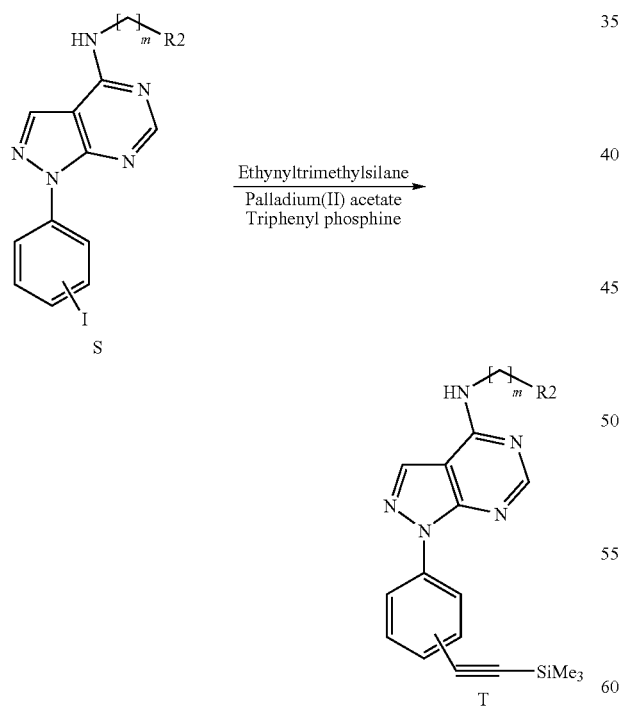

refluxing the compound of formula S with substituted trimethyl silyl acetylene in protic solvent to obtain an N-(trimethyl silyl protected ethynyl substituted) phenyl-4-amino substituted-pyrazolo[3,4-d]pyrimidine of formula-T;

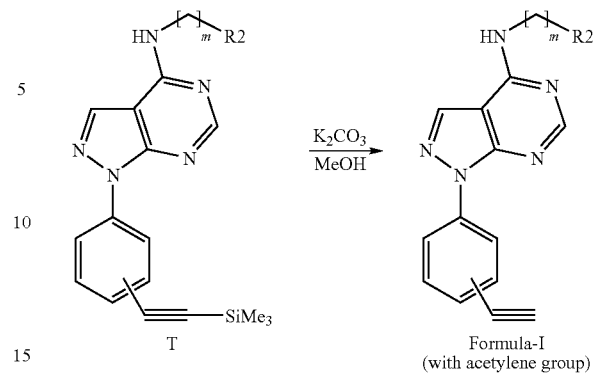

deprotecting the compound of formula T with a base to get the acetylene substituted compounds of formula-I.

7. A process for the preparation of N-((2,3-dihydrobenzo[b][1,4]dioxin-6-yl)methyl)-1-(3,5-dimethylphenyl)-1H-pyrazolo[3,4-d]pyrimidin-4-amine

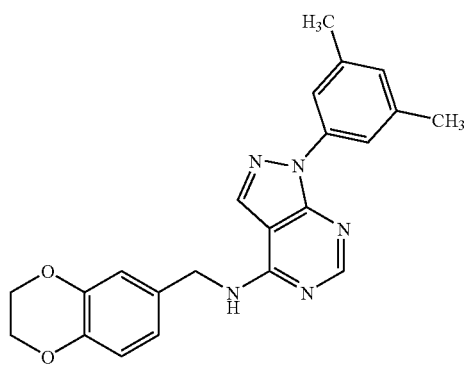 [SMILES: Cc1cc(C)cc(-n2ncc3c(NCc4ccc5c(c4)OCCO5)ncnc32)c1]

or salt thereof, the process comprising:

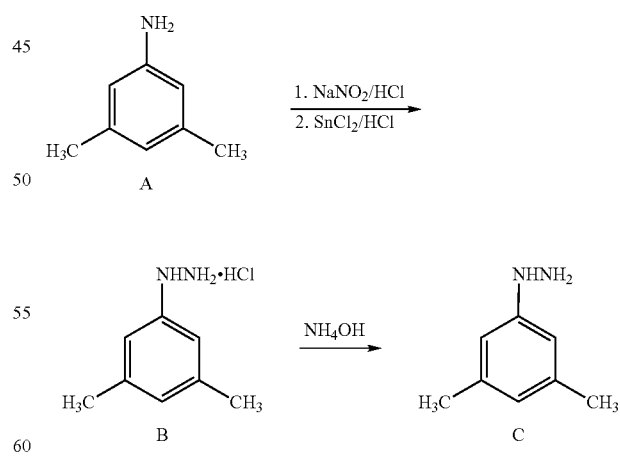

diazotising a compound of formula A with mineral acid and sodium nitrite at −10° C. to 5° C. to obtain a substituted phenyl hydrazine hydrochloride of formula-B;

neutralizing the compound of formula-B with a base to get a novel substituted phenylhydrazine of formula-C;

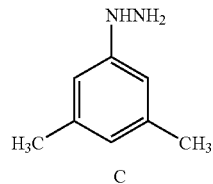

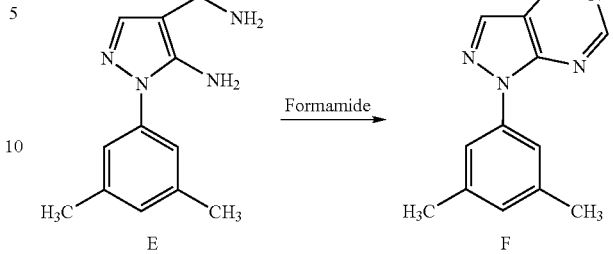

reacting the compound of formula E with formamide to obtain an N-substituted phenyl-5-amino-1H-pyrazole-4-carboxamide of formula F;

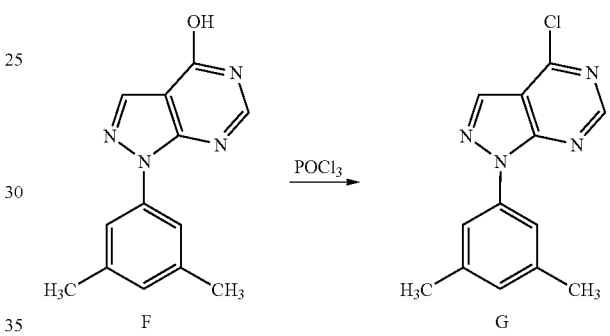

reacting the compound of formula C ethoxymethelenemalononitrile in protic solvent to obtain an N-substituted phenyl-5-amino-1H-pyrazole-4-carbonitrile of formula-D;

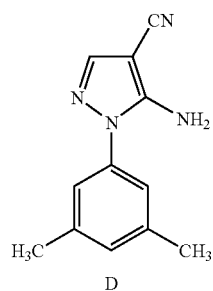

reacting the compound of formula F with phosphorus oxychloride, thionyl chloride, phosphorous trichloride or phosphorous pentachloride to obtain an N-substituted 4-chloro-pyrazolo[3,4-d]pyrimidine of formula-G;

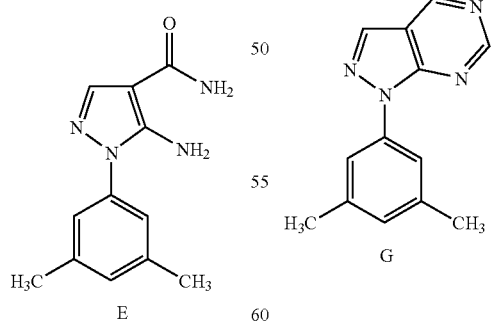

hydrolyzing the nitrile group of compound of formula D with a mineral acid in aqueous medium; followed by basification with a base at 10° C. to 40° C. to obtain an N-substituted phenyl-5-amino-1H-pyrazole-4-carboxamides of formula-E;

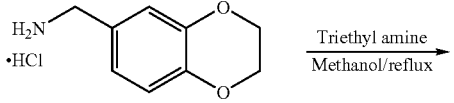

-continued

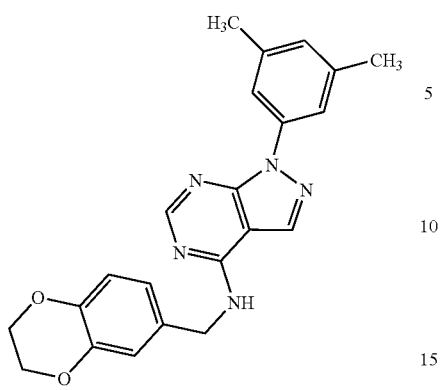

refluxing the compound of formula G with 2,3-dihydrobenzo[1,4]dioxin-6-yl-methylamine hydrochloride in a protic solvent to obtain the N-((2,3-dihydrobenzo[b][1,4]dioxin-6-yl)methyl)-1-(3,5-dimethylphenyl)-1H-pyrazolo[3,4-d]pyrimidin-4-amine.

8. The process of claim 7, further comprising treating the N-((2,3-dihydrobenzo[b][1,4]dioxin-6-yl)methyl)-1-(3,5-dimethylphenyl)-1H-pyrazolo[3,4-d]pyrimidin-4-amine with hydrochloric acid in a solvent to produce

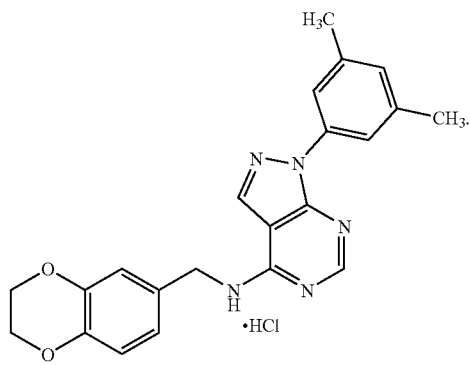 [SMILES: Cc1cc(C)cc(-n2ncc3c(NCc4ccc5c(c4)OCCO5)ncnc32)c1 ; Cl]

9. A process for the preparation of a compound of Formula-I with a cyano substitution on the N-phenyl ring or a pharmaceutically acceptable salt thereof, the process comprising:

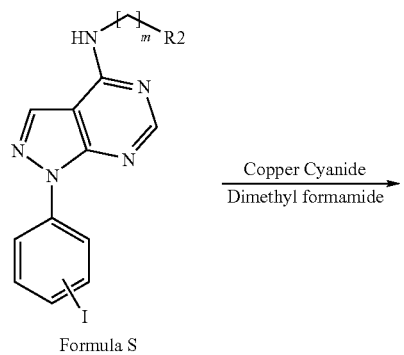

-continued

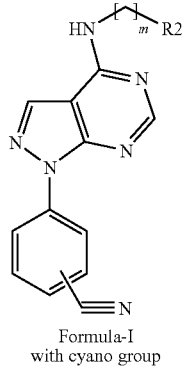
Formula-I
with cyano group heating a compound of formula S with copper cyanide and copper iodide in dimethyl formamide or dimethyl sulfoxide at temperatures ranging from 120° C. to 145° C. to obtain an N-(cyano substituted) phenyl-4-amino substituted-pyrazolo[3,4-d]pyrimidine.

10. A pharmaceutical composition comprising, a pharmaceutically acceptable excipient and a therapeutically effective amount of a compound of claim 2.

11. The process of claim 8, wherein the solvent comprises water, methanol, ethanol, isopropyl alcohol, ethyl acetate, acetonitrile, methylene chloride, acetone, or a mixture thereof.

12. The method of claim 6, wherein the acid:
for diazotising a compound of formula i comprises hydrochloric acid or sulfuric acid;
for hydrolyzing the nitrile group of the compound of formula L comprises sulphuric acid in aqueous medium;
or combination thereof.

13. The method of claim 6, wherein the mineral acid for diazotising a compound of formula i comprises hydrochloric acid.

14. The method of claim 6, wherein the base:
for neutralizing the compound of formula-J comprises sodium hydroxide, potassium hydroxide, sodium carbonate, potassium carbonate, ammonium carbonate, or a bicarbonate of an alkali metal;
for basification comprises ammonia, a bicarbonate of an alkali metal, a carbonate of an alkali metal, or a hydroxide of an alkali metal;
for deprotecting the compound of formula T comprises ammonia, a monoalkylamine, a dialkylamine, a trialkylamine, sodium hydroxide, potassium hydroxide, sodium carbonate, potassium carbonate, ammonium carbonate, or a bicarbonate of an alkali metal;
or combination thereof.

15. The method of claim 6, wherein the protic solvent:
for reacting the compound of formula K comprises methanol, ethanol, isopropanol, n-butanol, dimethyl formamide, or a mixture thereof;
for refluxing the compound of formula Q comprises methanol, ethanol, isopropyl alcohol, or a mixture thereof;
for refluxing the compound of formula S comprises methanol, ethanol, isopropyl alcohol, or a mixture thereof;
or combination thereof.

16. The method of claim 6, further comprising preparing ethoxymethylenemalononitrile in situ by reacting triethyl orthoformate and malononitrile; optionally, at 40° C. to 100° C.

17. The method of claim 6, wherein reacting with formamide is conducted in solvent, and the solvent comprises sulfolane, optionally, at 150° C. to 220° C.

18. The method of claim 6, comprising reacting the compound of formula O with phosphorus oxychloride.

19. The method of claim 18, wherein reacting is at reflux in solvent comprising methylene chloride, ethylene chloride, chloroform, or a mixture thereof.

20. The method of claim 6, comprising reacting the compound of formula O with thionyl chloride, phosphorous trichloride, or phosphorous pentachloride.

21. The method of claim 20, wherein reacting is at 25° C. in solvent comprising methylene chloride, ethylene chloride, chloroform, or a mixture thereof.

22. The method of claim 7, wherein the acid:
for diazotising a compound of formula A comprises hydrochloric acid or sulfuric acid;
for hydrolyzing the nitrile group of the compound of formula D comprises sulphuric acid in aqueous medium;
or combination thereof.

23. The method of claim 7, wherein the mineral acid for diazotising a compound of formula A comprises hydrochloric acid.

24. The method of claim 6, wherein the base:
for neutralizing the compound of formula B comprises ammonia, a monoalkylamine, a dialkylamine, a trialkylamine, sodium hydroxide, potassium hydroxide, sodium carbonate, potassium carbonate, ammonium carbonate, or a bicarbonate of an alkali metal;
for basification comprises ammonia, a bicarbonate of an alkali metal, a carbonate of an alkali metal, or a hydroxide of an alkali metal; or
combination thereof.

25. The method of claim 6, wherein the protic solvent:
for reacting the compound of formula C comprises methanol, ethanol, isopropanol, n-butanol, dimethyl formamide, or a mixture thereof;
for refluxing the compound of formula G comprises methanol, ethanol, isopropyl alcohol, or a mixture thereof; or combination thereof.

26. The method of claim 7, further comprising preparing ethoxymethylenemalononitrile in situ by reacting triethyl orthoformate and malononitrile; optionally, at 40° C. to 100° C.

27. The method of claim 6, wherein reacting with formamide is conducted in solvent, and the solvent comprises sulfolane, optionally, at 150° C. to 220° C.

28. The method of claim 7, comprising reacting the compound of formula F with phosphorus oxychloride.

29. The method of claim 28, wherein reacting is at reflux in solvent comprising methylene chloride, ethylene chloride, chloroform, or a mixture thereof.

30. The method of claim 7, comprising reacting the compound of formula F with thionyl chloride, phosphorous trichloride, or phosphorous pentachloride.

31. The method of claim 30, wherein reacting is at 25° C. in solvent comprising methylene chloride, ethylene chloride, chloroform, or a mixture thereof.

32. The compound of claim 1, wherein $R_2$ is 1,3-benzodioxol or 1,4-benzodioxin.

33. The compound of claim 1, wherein $R_1$ is alkyl, alkynyl, halogen, or cyano when n=1 and $R_1$ is alkyl when n=2.

* * * * *